US008738396B2

(12) United States Patent
Green, III et al.

(10) Patent No.: US 8,738,396 B2
(45) Date of Patent: *May 27, 2014

(54) INTEGRATED MEDICAL SOFTWARE SYSTEM WITH EMBEDDED TRANSCRIPTION FUNCTIONALITY

(75) Inventors: W. Thomas Green, III, Carrollton, GA (US); W. Thomas Green, Jr., Carrollton, GA (US); James T. Ingram, Carrollton, GA (US); Antonio Gerena, Villa Rica, GA (US); Jared Emerson Howerton, Carrollton, GA (US); Cecil Carter, Carrollton, GA (US); Johnathan Samples, Woodland, AL (US); Gregory H. Schulenburg, Carrollton, GA (US)

(73) Assignee: Greenway Medical Technologies, Inc., Carrollton, GA (US)

( * ) Notice: Subject to any disclaimer, the term of this patent is extended or adjusted under 35 U.S.C. 154(b) by 283 days.

This patent is subject to a terminal disclaimer.

(21) Appl. No.: 13/036,973

(22) Filed: Feb. 28, 2011

(65) Prior Publication Data

US 2011/0202370 A1 Aug. 18, 2011

Related U.S. Application Data

(63) Continuation-in-part of application No. 12/392,998, filed on Feb. 25, 2009, now Pat. No. 8,606,593, and a continuation-in-part of application No. 10/202,627, filed on Jul. 25, 2002.

(60) Provisional application No. 60/373,662, filed on Apr. 19, 2002.

(51) Int. Cl.
*G06Q 50/00* (2012.01)
*G06Q 10/00* (2012.01)

(52) U.S. Cl.
USPC .................................. 705/2; 705/3

(58) Field of Classification Search
USPC .......................................................... 705/2
See application file for complete search history.

(56) References Cited

U.S. PATENT DOCUMENTS 3,597,742 A 8/1971 Philipps et al.
4,491,725 A 1/1985 Pritchard
(Continued)

FOREIGN PATENT DOCUMENTS

EP 0808882 A2 11/1997
EP 1086997 A2 3/2001
(Continued)

OTHER PUBLICATIONS

McDonald, The Regenstrief Medical Record System: a quarter century experience, Jun. 1999, International Journal of Medical Informatics, vol. 54, Issue 3, pp. 225-253.*

(Continued)

*Primary Examiner* — Tran Nguyen
(74) *Attorney, Agent, or Firm* — Blank Rome LLP

(57) ABSTRACT

An integrated medical software system with embedded transcription functionality, and a method of using that system, is disclosed. The system includes a clinical software module that is configured to be executed by a processor to create an electronic document and to capture clinical data for a patient in the electronic document during an encounter with the patient. The system also includes a transcription software application that is configured to be executed by the processor to select predefined clinical data that will appear within the electronic document in response to speech commands and to automatically transcribe dictated clinical data that will appear within the electronic document in response to dictation, wherein the predefined clinical data being previously linked to at least one of a diagnosis code and a procedure code and the dictated clinical data being automatically linked to at least one of a diagnosis code and a procedure code as it is transcribed. And the system includes an account management software module that is configured to be executed by the processor to automatically generate at least one of a bill, a claim, or a statement for the patient using the at least one of a diagnosis code and a procedure code linked to at least one of the predefined clinical data and the dictated clinical data.

18 Claims, 45 Drawing Sheets

(56) References Cited

U.S. PATENT DOCUMENTS

| | | |
|---|---|---|
| 4,766,542 A | 8/1988 | Pilarczyk |
| 4,987,538 A | 1/1991 | Johnson et al. |
| 5,065,315 A | 11/1991 | Garcia |
| 5,070,452 A | 12/1991 | Doyle, Jr. et al. |
| 5,205,861 A | 4/1993 | Matrick |
| 5,267,155 A | 11/1993 | Buchanan et al. |
| 5,359,509 A | 10/1994 | Little et al. |
| 5,361,202 A | 11/1994 | Doue |
| 5,572,422 A | 11/1996 | Nematbakhsh et al. |
| 5,583,758 A | 12/1996 | McIlroy et al. |
| 5,644,778 A | 7/1997 | Burks et al. |
| 5,659,741 A | 8/1997 | Eberhardt |
| 5,664,207 A | 9/1997 | Crumpler et al. |
| 5,704,044 A | 12/1997 | Tarter et al. |
| 5,737,539 A | 4/1998 | Edelson et al. |
| 5,748,907 A | 5/1998 | Crane |
| 5,758,095 A | 5/1998 | Albaum et al. |
| 5,772,585 A | 6/1998 | Lavin et al. |
| 5,823,948 A | 10/1998 | Ross, Jr. et al. |
| 5,826,237 A | 10/1998 | Macrae et al. |
| 5,827,180 A | 10/1998 | Goodman |
| 5,832,488 A | 11/1998 | Eberhardt |
| 5,845,253 A | 12/1998 | Rensimer et al. |
| 5,857,967 A | 1/1999 | Frid et al. |
| 5,899,998 A | 5/1999 | McGauley et al. |
| 5,903,889 A | 5/1999 | de la Huerga et al. |
| 5,911,687 A | 6/1999 | Sato et al. |
| 5,915,241 A | 6/1999 | Giannini |
| 5,924,074 A | 7/1999 | Evans |
| 5,933,809 A | 8/1999 | Hunt et al. |
| 5,940,802 A | 8/1999 | Hildebrand et al. |
| 5,946,659 A | 8/1999 | Lancelot et al. |
| 5,950,630 A | 9/1999 | Portwood et al. |
| 5,956,690 A | 9/1999 | Haggerson et al. |
| 5,970,466 A * | 10/1999 | Detjen et al. ............ 705/7.19 |
| 5,991,729 A | 11/1999 | Barry et al. |
| 5,991,730 A | 11/1999 | Lubin et al. |
| 5,995,937 A | 11/1999 | DeBusk et al. |
| 5,995,939 A | 11/1999 | Berman et al. |
| 6,004,276 A | 12/1999 | Wright et al. |
| 6,018,713 A | 1/2000 | Coli et al. |
| 6,024,699 A | 2/2000 | Surwit et al. |
| 6,047,259 A | 4/2000 | Campbell et al. |
| 6,054,505 A | 4/2000 | Gundlach et al. |
| 6,106,513 A | 8/2000 | McMillen et al. |
| 6,283,761 B1 | 9/2001 | Joao |
| 6,289,316 B1 | 9/2001 | Aghili et al. |
| 6,314,556 B1 | 11/2001 | DeBusk et al. |
| 6,347,329 B1 | 2/2002 | Evans |
| 6,374,229 B1 | 4/2002 | Lowrey et al. |
| 6,408,303 B1 | 6/2002 | Richards |
| 6,603,464 B1 * | 8/2003 | Rabin ....................... 345/179 |
| 7,461,079 B2 | 12/2008 | Walker et al. |
| 2001/0023419 A1 | 9/2001 | LaPointe et al. |
| 2001/0041991 A1 | 11/2001 | Segal et al. |
| 2002/0007311 A1 | 1/2002 | Iseki et al. |
| 2002/0010679 A1 | 1/2002 | Felsher |
| 2002/0073111 A1 | 6/2002 | Heyliger |
| 2002/0103811 A1 | 8/2002 | Fankhauser et al. |
| 2002/0138524 A1 * | 9/2002 | Ingle et al. ................ 707/530 |
| 2003/0033169 A1 | 2/2003 | Dew |
| 2004/0010425 A1 | 1/2004 | Wilkes et al. |
| 2004/0128323 A1 | 7/2004 | Walker et al. |
| 2006/0106641 A1 | 5/2006 | Bartsch et al. |
| 2008/0040151 A1 | 2/2008 | Moore |
| 2008/0046292 A1 | 2/2008 | Myers et al. |
| 2008/0243546 A1 | 10/2008 | Ashford et al. |
| 2009/0080408 A1 | 3/2009 | Natoli et al. |

FOREIGN PATENT DOCUMENTS

| | | |
|---|---|---|
| EP | 1114851 A1 | 7/2001 |
| EP | 1122286 A1 | 8/2001 |
| EP | 1158030 A2 | 11/2001 |
| EP | 1167471 A2 | 1/2002 |
| WO | WO-95/12857 | 5/1995 |
| WO | 0110963 A1 | 2/2001 |
| WO | 0125340 A1 | 4/2001 |
| WO | 0194476 A2 | 12/2001 |

OTHER PUBLICATIONS

Anonymous. Charting eases onto the information highway. Medical Economics. Oradell: Jul. 25, 1994, vol. 71, Isssue 14; p. 82.
Canadian Datasystems. A cure for the paper plague, May 1991, vol. 23, Issue 14; p. D13.
PR Newswire. Homestead.com helps people jump startg their web sites with customizable templates and site building resources, New York: Feb. 7, 2000; p. 1.
Gilnert, Susan, By design adds tools and clip art. Computer Shopper, Jun. 1994, vol. 14, No. 6, p. 494.
Retrieve Form for Data Capture (RFD); power point document http://ww.ihe.net/Participation/upload/iti11_ihewkshp07_rfd_details_cole.pdf.
Brown et al. "VistaA—U.S. Dept. of Veterans Affairs national-scale HIS"; International Journal of Medical Informatics; 2003; pp. 135-156.
Bellazzi, Web-based telemedicine systems for home-care; technical issues and experiences, Computer Methods and Programs in Biomedicine, vol. 64, Issue 3, Mar. 1, 2001, pp. 175-187.
http://www.ihe.net/Technical_Framework/upload/IHE_ITI_TF_Suppl_RFD_TI_2006_09_25.pdf.
Poirier, Billing third party payers for pharmaceutical care services, J AM Pharm Assoc. 1999; 39:50-64.

* cited by examiner

| | | |
|---|---|---|
| A/R Management Chart Registration Schedule System Dictation | | Thursday, June 21, 2001  logout |

TEMPLATE BUILDER

Info | Search

Options:

Create Template
Edit Template
Delete Template
Delete Folder
Export Template
Import Template
Chief Complaint Admin
HPI Admin
Review of Systems Admin
Physical Exam Admin
Assessment/Plan Admin Folder: Root                                                                   Add ☐

| Name | Description | Last Modified |
|---|---|---|
| ☐ Hernia | Folder | 05/16/2001 10:05:00 AM |
| ☐ Everyday Use Templates xx | Folder | |
| ☐ aGallstones2 | Cholithiasis: Consultation, initial | 03/22/2001 02:21:00 PM |
| ☐ asdffffff | | 05/08/2001 10:14:00 AM |
| ☐ Base 1 | | 06/01/2001 02:17:00 PM |
| ☐ Base 2 | | |
| ☐ Breast Cancer | Breast Cancer: Initial Consultation | 05/09/2001 11:27:00 AM |
| ☐ Breast problems | breast lumps | 04/23/2001 11:15:00 AM |
| ☐ cervicle cryosurgery | cervicle cryosurgery | 05/09/2001 11:48:00 AM |
| ☐ cervicle cryosurgery 2 | cervicle cryosurgery | 04/23/2001 05:08:00 |

HENT
☑ ⊞ earache

Cardiovascular
☑ ⊞ cardiac murmur in ventrical right
☐ ⊞ mild chest pain in chest wall right midsternal; functional worsens with ambulation ⎫
☐☐ deep pain                                                                              ⎬ 1800
☐☐ chronic cough                                                                          ⎭

Respiratory
☐☐ shortness of breath

| | | Thursday, April 18, 2002 |
|---|---|---|
| A/R Management  Chart  Registration  Schedule  System  Dictation | ✉ ⓘ | peterw |
| | | Doe, John(1003) |

TEMPLATE BUILDER

| Info | Search | | | | | | | |
|---|---|---|---|---|---|---|---|---|
| Start | CC | HPI | ROS | PE | A/P | Preview | Save | |

Plan

Use the tools below to create your group-level and diagnosis-specific plans.

Common Plan

⊕ Orders
  Labs
  ☐ Arthritis panel (80072)      Delete
  ☑ Renal function panel (80069)  Delete
  ☐ Alpha-fetoprotein, serum (82105)  Delete ⊕ Medications
⊕ Instructions

Acute Myocarditis 422.90

⊕ Orders
⊕ Medications
⊕ Instructions

| Info | Search | | | | | | | | | Thursday, September 11, 2001 |
|---|---|---|---|---|---|---|---|---|---|---|
| | | A/R Management | Chart | Registration | Schedule | System | | | | logout |
| | | TEMPLATE BUILDER | | | | Dictation | | | | |
| | Start | CC | HPI | ROS | PE | A/P | Preview | | Save | |

Template
CABG Pre-surgical
O...  ← 2402

Chief Complaint
☐ I am tired.
☐ My chest hurts.
☐ I am short of breath.
☐ I am having surgery for chest pain.
☐ I am going to have bypass grafting.

History of Present Illness
CABG Pre-surgical Office Visit
Patient describes symptom [severe]. This patient complains of symptom of the last [NUMBER][DURATION]. Admits symptom for the last # hours.

Review of Systems ⊕

Cardiovascular
☐ chest pain     ☐ palpitations     ☐ peripheral edema     ☐ generalized edema Respiratory
☐ shortness of breath

Physical Exam ⊕ ← 2404

TEMPLATE BUILDER

A/R Management  Chart  Registration  Schedule  System  Dictation

Thursday, September 13, 2001  logout

Start  CC  HPI  ROS  PE  A/P  Save

Template

CHF Template

Failure
☑ Congestive Heart Failure  428.0

Orders
☐ CARDIOVASCULAR STRESS TEST W/ECG MONITOR; W/ PHYSICIAN SUPERVISION, INTERPRETATION & REPORT  93015
☐ MYOCARDIAL PERFUSION IMAGING; PLANAR, MULTIPLE STUDIES, REST &/OR STRESS & REDISTRIBUTION  75461
☐ RADIOLOGIC EXAM, CHEST, 2 VIEWS, FRONTAL & LATERAL  71020

Medications

Instructions/Education
☐ Bedrest.
☐ No heavy lifting.
☐ Walk 100 ft. twice daily, stopping if SOB.
☐ Low salt diet.
☐ Low fat diet.

A/R Management  Chart  Registration  Schedule  System  Dictation

Thursday, September 12, 2001
Chandler, Anna(2958)  logout

Facesheet ○ Documents | Progress Note | Close Chart

Info  Search

Visit: 9/12/2001

Create Note
Physician Templates
Nursing Templates

Viewing Options
Index View
Document View

Document Options

Print Document

Document History
Version: 2
9/12/2001 SLC
Version: 1
9/12/2001 SLC

Progress Note

Patient:     Anna Chandler        Patient ID: 2958        Sex: Female
Birthdate:   January 11, 1933

Chief Complaint

- I am tired.
- My chest hurts.
- I am short of breath.
- I am having surgery for chest pain.
- I am going to have bypass grafting.

History of Present Illness

Patient describes symptom chronic. This patient complains of symptom for the last 2 months. Admits symptom for the last # hours.

Review of Systems

- Cardiovascular: + chest pain - palpitations + peripheral edema - generalized edema
- Respiratory: + shortness of breath

Physical Examination

Chandler, A.

FIG. 33

Thursday, September 12, 2001
Chandler, Anna(2958)

A/R Management | Chart | Registration | Schedule | System | Dictation

Close Chart

Visit: 9/12/2001

Info | Search

Create Note
Physician Templates
Nursing Templates

Viewing Options
Index View
Document View

Document Options

Print Document

Document History
Version 2
9/12/2001 SLC
Version 1
9/12/2001 SLC

Facesheet ○ Documents | Progress Note

- Chest:
  ○ Respiratory Effort: (+)inspiratory dyspnea (+)inspiratory rales (-)expiratory rales
  ○ Auscultation: (+)inspiratory wheezing (-)rhonchi

- Cardiovascular:
  ○ Auscultation: (-)early diastolic murmur (-)presystolic murmur
  ○ Carotid arteries: (+)injury of external carotid artery
  ○ Pedal pulses: (+)pedal pulse Assessment ○ Cardiac Arrest 427.5

Plan

- Orders
  ○ TRANSPORTATION OF PORTABLE EKG TO FACILITY OR LOCATION, PER PATIENT R0076
  ○ TRANSPORTATION OF PORTABLE X-RAY EQUIPMENT AND PERSONNEL TO HOME OR NURSING HOME, PER TRIP TO FACILITY OR LOCATION, ONE PATIENT SEEN R0070

- Patient Instructions:
  ○ Complete Bedrest
  ○ Sublingual Nitroglycerin for episode of chest pain.
  ○ Repeat EKG tomorrow, this office Chandler, A.

FIG. 34

| A/R Management | Chart | Registration | Schedule | System | Dictation | | | |
|---|---|---|---|---|---|---|---|---|
| | | | | | | | | Thursday, September 12, 2001 |
| | | | | | | | | Chandler, Anna(2958) |
| | | | | | | | | Close Chart |

Info | Search
Visit: 9/12/2001

Facesheet ○ Documents | Progress Note

Chart Documentation

Create Note
Physician Templates
Nursing Templates

Progress Notes     Sort: VisitDate

Viewing Options
Index View
Document View
Show Category

| | Visit Date | Document Type | Created By | Created/Last Modified | Status |
|---|---|---|---|---|---|
| | No Visit Associated | Progress Note | schandler | 9/12/2001 6:58:49 AM | In Progress |
| | No Visit Associated | Progress Note | schandler | 9/7/2001 10:01:46 AM | Authenticated |
| | No Visit Associated | Progress Note | schandler | 9/4/2001 6:48:35 AM | Authenticated |
| | No Visit Associated | | | 8/23/2001 12:46:27 PM | In Progress |

Chandler, A. | Schulenburg, G. | Chandler, S. | Felt, S. | Chandler, I. | Test, S.

INTEGRATED MEDICAL SOFTWARE SYSTEM WITH EMBEDDED TRANSCRIPTION FUNCTIONALITY

CROSS-REFERENCE TO RELATED APPLICATIONS

This application is a continuation-in-part of co-pending U.S. patent application Ser. No. 12/392,998, filed Feb. 25, 2009, and co-pending U.S. patent application Ser. No. 10/202,627, filed Jul. 25, 2002, which claims priority to U.S. Provisional Application Ser. No. 60/373,662, filed Apr. 19, 2002, the entire contents of which are incorporated herein by reference.

FIELD OF THE INVENTION

The present invention relates to a medical software system that integrates all aspects of practice management, managed care, and medical research. More particularly, the present invention relates to an integrated medical software system with embedded transcription functionality for increasing the efficiency of data capture and flow within that system.

BACKGROUND OF THE INVENTION

Traditionally, healthcare providers have kept all of their patients' information in paper filing systems. That patient information includes, but is not limited to, patients' demographic information (e.g., age, weight, gender, race, income, and geographic location), financial information (e.g., outstanding balances, insurance claims currently being processed, and other account information), and clinical information (e.g., clinician documentation of observations, thoughts and actions, treatments administered, patient history, medication and allergy lists, vaccine administration lists, laboratory reports, X-rays, charts, progress notes, consultation reports, procedure notes, hospital reports, correspondence, and test results). The healthcare providers, or clinicians, that maintain that patient information include, but are not limited to, physicians (Doctors of Medicine (MDs) and Doctors of Osteopathic Medicine (DOs)), dentists, chiropractors, podiatrists, therapists, psychologists, physician assistants, nurses, medical assistants, and technicians.

The manual, paper-based practice of keeping a patient's information, however, is a very inefficient, labor-intensive process that requires many checks and balances to ensure accurate processing of the information and, therefore, takes up a significant amount of clinician's time that could otherwise be spent with patients. Accordingly, electronic medical records (EMRs), Electronic Health Records (EHRs), and Personal Health Records (PHRs) have been developed to provide many of the functionalities and features of paper filing systems in an electronic, paperless format.

An EMR is an electronic record of patient information that can be created, gathered, managed, and consulted by the authorized clinicians and other staff at the healthcare practice where the record is created. An EHR is an electronic record of patient information that conforms to nationally recognized interoperability standards and that can be created, managed, and consulted by authorized clinicians and staff, both at the healthcare practice that creates the record and at other healthcare practice sites. And, a PHR is an electronic record of patient information that conforms to nationally recognized interoperability standards and that can be drawn from multiple sources while being managed, shared, and controlled by the patient to whom it belongs. Accordingly, EMRs are aimed primarily at the efficient management of multiple records in a single healthcare provider's practice, while EHRs and PHRs are aimed primarily at integrating multiple data sources into each electronic record.

The nationally recognized interoperability standards for EHRs are currently endorsed by the Healthcare Information Technology Standards Panel (HTISP) and certified by the Certification Commission for Healthcare Information Technology (CCHIT). Those standards require EHRs to have the ability to communicate and exchange data accurately, effectively, securely, and consistently with different information technology systems, software applications, and networks in various settings such that the clinical or operational purpose and meaning of the data are preserved and unaltered as that data is exchanged. Thus, while an EMR is generally characterized as an electronic version of a physician's paper record, an EHR is characterized as a more comprehensive record containing additional data integrated to and from other sources. EHRs are further characterized as being either "basic" or "fully functional." A basic EHR includes patient demographics, problem lists, clinical notes, orders for prescription, and viewing laboratory and imaging results. A fully functional EHR includes patient demographics, problem lists, clinical notes, medical history and follow-up, orders for prescriptions, orders for tests, prescription orders sent electronically, laboratory and imaging results, warnings of drug interactions or contraindications, out-of-range test levels, and reminders for guideline-based interventions.

At their core, EMR and EHR systems include large-capacity databases that contain patient information stored in structured, relational tables of searchable data. Unfortunately, many of the vendors of EMR and EHR systems have resisted making their software capable of exporting and importing patient information using uniform electronic messaging, document, and form management standards (e.g., the Health Level Seven (HL7) messaging standard, the Continuity of Care Document (CCD) document standard, and the Retrieve Form for Data Capture (RFD) form management standard). And, when data is not captured and stored using uniform, standardized medical vocabularies, and when it is not transmitted using uniform messaging, document, and form management standards, that data of little use outside of the system in which it is captured and stored. Instead, custom interfaces must be designed to allow the import and export of data between systems so that data can be shared between those systems. The process of developing different interfaces between the disparate formats used by different vendors is expensive and difficult. Moreover, such interfaces are also costly and labor-intensive to maintain.

The problem of interfacing different EMR and EHR systems is exacerbated by the fact that, in the present health care industry, most patient visits are to small, self-contained practices that often treasure their autonomy and are unwilling and/or unable to acquire EMR and EHR systems unless each of those systems is individually tailored to the narrow objectives of each specific self-contained practice. Accordingly, most EMR and EHR vendors have been forced to provide healthcare practices with individually customized systems that employ stand-alone features and functions on the basis of what a specific practice group wants and needs, which means that similar practice groups in adjacent counties may have very different system features and functions based on their different priorities. Thus, the various existing EMR and EHR systems are not well suited for interaction and data exchange with each other, or for maintaining information that would be useful to other systems. The data collected by the different practice groups using EMR and EHR systems is therefore severely fragmented.

In addition, most of the commercially available EMR and EHR systems have not been well received by healthcare providers. In fact, according to a 2008 survey conducted by the National Center for Health Services (NCHS), a division of the Centers for Disease Control and Prevention (CDC), while about 40% of U.S. office-based physicians reported using EMR systems, only 17% reported using basic EHR systems, and only 4% reported using fully functional EHR systems. Healthcare providers tend to resist such systems because those systems are unable to keep up with the workflow demands of clinicians during the various tasks they perform throughout the day. Traditional EMR and EHR systems are generally technology-driven, as opposed to being user-driven. Accordingly, healthcare providers find them difficult to use, especially those healthcare providers that have difficulty with computer technology, and especially when it involves adopting new software with which the healthcare provider is not already familiar. Many healthcare providers would rather focus solely on patient care than be bothered with learning how to operate the latest computer technology.

In an attempt to gain wider acceptance of EMR and EHR systems, some health information technology (HIT) engineers have developed user interfaces to help ease healthcare providers' transition into the electronic record-keeping medium. For example, because healthcare is a dictation-intensive field, some HIT engineers have adopted a speech recognition approach for interfacing with EMR and EHR systems. That approach allows healthcare providers to dictate information as they traditionally have done, except that the information is captured in a computer-readable medium (e.g., an XML file) that can be input directly into EMR and EHR systems. Two different types of speech recognition technology have been developed to help ease healthcare providers' transition into the electronic record-keeping medium and improve turnaround time in generating electronic patient records—back-end speech recognition and front-end speech recognition.

Back-end speech recognition generates an electronic text document in the background as a healthcare provider dictates without the healthcare provider being able to see or edit, and oftentimes without the healthcare provider even being aware of, what is being transcribed in the electronic text document. The resulting electronic text document, along with the corresponding voice file, is then sent to a medical transcription/editing service that reads the electronic text document, listens to the voice file, and corrects any mistakes (recognition and/or dictation) in the electronic text document. The medical transcription/editing service then returns the corrected electronic text document to the healthcare practice for entry into an EMR or EHR system. The medical transcription/editing service may also enter the appropriate information into the EMR or EHR system themselves. And, if the information captured by back-end speech recognition is used to generate documentation that requires the healthcare provider's signature (e.g., progress notes, consultation reports, procedure notes, hospital reports, etc.), that documentation will also need to be provided to the healthcare provider for review and signature. The turnaround time required for a medical transcription/editing service to review and correct the electronic text document is unpredictable and inconvenient. Using such services also creates an additional expense for healthcare providers, who already suffer from large overhead costs.

Front-end speech recognition provides faster turnaround times and eliminates the need for medical transcription/editing services by allowing the healthcare provider to view and edit the electronic text document as it is generated. Thus, instead of using medical transcription/editing services to review and edit the electronic text document, the healthcare provider can immediately see and correct any mistakes (recognition and/or dictation) in the electronic text document Like traditional EMR and EHR systems, however, traditional front-end speech recognition is often provided as separate software that must be interfaced with the EMR or EHR system with which it is being used. Thus, unlike back-end speech recognition running in the background, healthcare providers must familiarize themselves with, and ultimately accept, that new software platform for it to be of any beneficial use.

Although back-end speech recognition does not require healthcare providers to familiarize themselves with and accept new software, neither the software used to provide traditional back-end speech recognition nor the software used to provide traditional front-end speech recognition incorporates uniform electronic messaging, document, and form management standards to import and export the information captured therewith. Instead, the information captured by that software is typically only used to complete the specific clinical documentation for which it was captured (e.g., progress notes, consultation reports, procedure notes, hospital reports, etc.) rather than being provided in a format that can be used for other purposes, such as data collection and analysis for practice management and medical research. And, as discussed above, when data is not captured and stored using uniform, standardized medical vocabularies, and when it is not transmitted using uniform messaging, document, and form management standards, that data is of little use outside of the system in which it was captured unless custom interfaces are designed to connect that system to other systems. Much less, it is of little use outside of the document for which it was captured.

Another shortcoming of conventional speech recognition technology is that such technology requires a significant amount of voice recognition training by a user for the speech recognition to be accurate. For example, a user will be required to dictate several passages into a computer to "train" the voice recognition software on that computer to recognize that user's voice and mannerisms. A "voice profile" is created for that specific user based on that training. The user must either save that voice profile to a portable electronic storage medium (e.g., a CD-ROM or zip disk) or perform the training again whenever that user uses a different computer, or accesses the computer remotely, to dictate speech. Accordingly, management of a user's voice profile can become problematic and burdensome when a user frequently uses different systems to dictate speech.

Because most EMR and EHR systems, and the speech recognition software with which they are interfaced, are not capable of exporting and importing patient information in a standardized format, and because they do not utilize functions and features suited for interaction and data exchange with other systems, the fragmented pools of data collected using those systems cannot easily be combined. Accordingly, an individual healthcare practice cannot share data between its individually customized systems in a way that streamlines management of that healthcare practice, but instead must capture, store, and manage duplicate sets of data between its disparate, stand-alone systems. Moreover, researchers cannot easily collect data from multiple healthcare practices for performing medical research, maintaining disease registries, tracking patient care for quality and safety initiatives, and performing composite clinical and financial analytics. Instead, those processes remain time-consuming and expensive. For example, a clinical research organization (CRO) tasked with identifying patients that satisfy specific criteria for participating in a clinical trial must still sort through voluminous libraries of paper medical records and unstructured data, spending large amounts of time and money searching for candidates.

Those problems are compounded by the regulations of the Health Insurance Portability and Accountability Act (HIPAA). The implementation of the regulations of HIPAA has increased the overall amount of paperwork and the overall costs required for healthcare providers to operate. And the complex legal implications associated with those regulations have caused concerns with compliance among healthcare providers. With regard to researchers, the HIPAA regulations have hindered their ability to perform retrospective, chart-based research as well as their ability to prospectively evaluate patients by contacting them for follow-up surveys. The HIPAA regulations have also led to significant decreases in patient accrual for research, increases in time spent recruiting patients for research, and increases in mean recruitment costs. And by requiring that informed consent forms for research studies include extensive detail on how the participant's protected information will be kept private, those already complex documents have become even less user-friendly.

Accordingly, there is a need for a medical software system that seamlessly integrates the systems required to manage the different activities performed at a healthcare practice (i.e., an EMR or EHR system, a patient registration system, a scheduling system, an account management system, a billing system, etc.) so that duplicate and/or inconsistent data is not captured, stored, and managed by disparate, stand-alone systems. There is also a need for that integrated medical software system to include embedded speech understanding functionality for capturing data in a cost-effective and user-friendly manner. And there is a need for a plurality of such systems for systematically analyzing, collecting, and tracking patient data across a vast patient population (e.g., a community, region, state, nation, etc.) while complying with HIPAA regulations.

SUMMARY OF THE INVENTION

To solve at least the above problems and disadvantages, and to provide at least the advantages discussed below, a non-limiting object of the present invention is to provide an integrated medical software system with embedded transcription functionality and a method of using that system. The system includes a clinical software module that is configured to be executed by a processor to create an electronic document and to capture clinical data for a patient in the electronic document during an encounter with the patient. The system also includes a transcription software application that is configured to be executed by the processor to select predefined clinical data that will appear within the electronic document in response to speech commands and to automatically transcribe dictated clinical data that will appear within the electronic document in response to dictation, wherein the predefined clinical data being previously linked to at least one of a diagnosis code and a procedure code and the dictated clinical data being automatically linked to at least one of a diagnosis code and a procedure code as it is transcribed. And the system includes an account management software module that is configured to be executed by the processor to automatically generate at least one of a bill, a claim, or a statement for the patient using the at least one of a diagnosis code and a procedure code linked to at least one of the predefined clinical data and the dictated clinical data. Those and other objects of the invention, as well as many of the intended advantages thereof, will become more readily apparent when reference is made to the following description, taken in conjunction with the accompanying drawings.

BRIEF DESCRIPTION OF THE DRAWINGS

The following drawings are part of the specification and represent preferred embodiments of the present invention. The components in the drawings are not necessarily to scale, emphasis instead being placed upon illustrating the principles of the present invention. And, in the drawings, like reference numerals designate corresponding parts throughout the several views.

FIG. 5 illustrates a desktop screen and internal messaging supported by the framework module of the integrated ambulatory suite illustrated in FIG. 4;

FIGS. 6A and 6B illustrate an example of a visit information check-in screen and a patient registration information screen supported by the framework module of the integrated ambulatory suite illustrated in FIG. 4;

FIGS. 8-10 illustrate an example of a charges screen, a contracts/fee schedule screen, and an account information screen, respectively, supported by the A/R module illustrated in FIG. 7;

FIG. 13 illustrates an example of a main template builder screen supported by the clinical module illustrated in FIG. 11;

FIGS. 15 and 16 illustrate an example of a template builder screen for a history of present illness section supported by the clinical module illustrated in FIG. 11;

FIGS. 17 and 18 illustrate an example of a template builder screen for a review of systems section supported by the clinical module illustrated in FIG. 11;

FIG. 19 illustrates an example of a template builder screen for a physical exam section supported by the clinical module illustrated in FIG. 11;

FIGS. 20-23 illustrate an example of a template builder screen for an assessment/plan section supported by the clinical module illustrated in FIG. 11;

FIG. 24 illustrates an example of a preview screen for a chief complaint section, a history of present illness section, and review of systems section supported by the clinical module illustrated in FIG. 11;

FIG. 25 illustrates an example of a preview screen for a review of systems section and a physical exam section supported by the clinical module illustrated in FIG. 11;

FIG. 26 illustrates an example of a preview screen for a physical exam section and an assessment/plan section supported by the clinical module illustrated in FIG. 11;

FIG. 27 illustrates an example of a preview screen for an assessment/plan section supported by the clinical module illustrated in FIG. 11;

FIGS. 29-32 illustrate examples of a progress note being completed by a clinician using the EHR component of the clinical module illustrated in FIG. 11;

FIGS. 33 and 34 illustrate an example of a completed progress note generated with the clinical module illustrated in FIG. 11;

FIG. 35 illustrates a list of documents in a patient's chart screen supported by the clinical module illustrated in FIG. 11;

FIG. 37 illustrates an example of a facesheet screen supported by the clinical module illustrated in FIG. 11;

FIG. 38 illustrates an example of an appointment scheduling screen supported by the scheduling module of the integrated ambulatory suite illustrated in FIG. 4;

FIG. 40 illustrates a dictation a dictation toolbar being displayed in a document in which a clinician is working according to a non-limiting embodiment of the present invention;

DETAILED DESCRIPTION OF THE EXEMPLARY EMBODIMENTS

Figure 1:
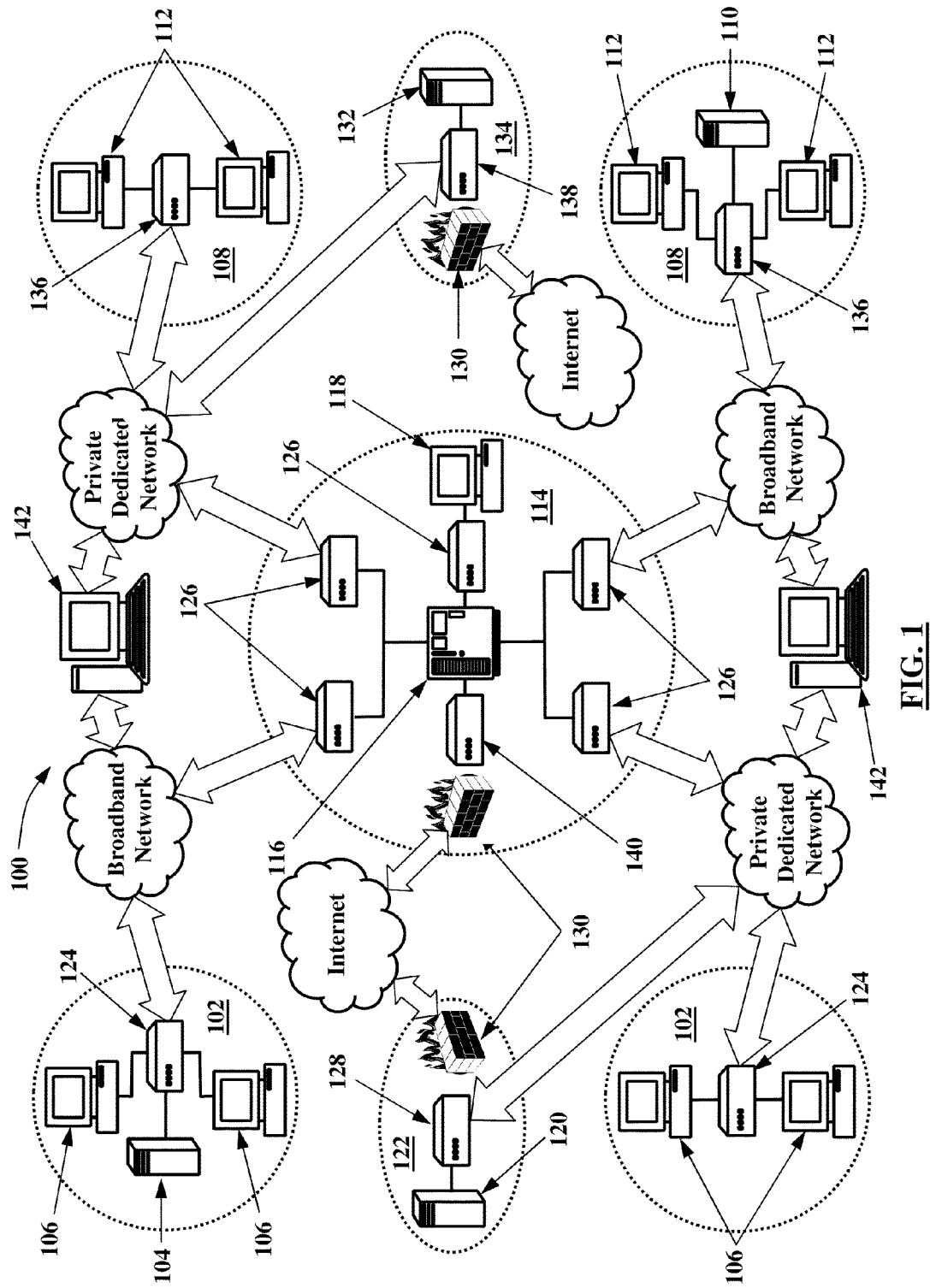
FIG. 1 illustrates the infrastructure of an integrated physician's network according to a non-limiting embodiment of the present invention.

Non-limiting embodiments of the present invention will now be disclosed in detail, by way of example, with reference to the drawings. In describing those embodiments, specific terminology will be resorted to for the sake of clarity. However, the invention is not intended to be limited to the specific terms so selected, and it is to be understood that each specific term includes all technical equivalents that operate in similar manner to accomplish a similar purpose.

The present invention provides a medical software system that integrates each the systems required to manage the different activities performed at a healthcare practice (e.g., an EMR or EHR system, a patient registration system, a scheduling system, an account management system, a billing system, etc.) on a single technology platform so that duplicate and/or inconsistent data is not captured, stored, and managed by disparate, stand-alone systems. Such a system is hereinafter referred to as an "integrated ambulatory suite." Each of the systems integrated into the integrated ambulatory suite are built on the same architecture and are designed to share information seamlessly based on integration rather than interfacing. Integration provides a single-vendor solution for addressing all of a healthcare practice's needs. It also allows for single-vendor support and the sharing of all data across all system components through a single database, which avoids errors, duplication of data entry, and inconsistency of information.

In addition to eliminating duplicate and/or inconsistent data across multiple systems, providing a single, integrated medical software system for all of the activities of a healthcare practice allows better patient tracking, cost accounting analysis, data security, and audit trails. It also allows administration of the various functions of the integrated ambulatory suite to be managed through a single system administration feature. And it allows the entire integrated ambulatory suite to be updated with a single data push from the vendor whenever new or updated system software is released, with consideration for all of the various functionalities that may be affected within the integrated ambulatory suite. Thus, providing a single-source solution also minimizes the cost of ongoing system maintenance.

The integrated ambulatory suite of the present invention includes embedded speech recognition functionality for capturing data in a cost-effective and user-friendly manner. That speech understanding functionality is integrated with each of the different modules and components of the integrated ambulatory suite so it can be used to capture data while performing substantially any activity at a healthcare practice (e.g., messaging, scheduling, account management, generating correspondence, and generating clinical documentation). And because that functionality can be used with each of the different modules and components of the integrated ambulatory suite, data captured using that functionality can flow throughout the integrated ambulatory suite to assist in completing substantially any type of electronic record for a patient (e.g., a schedule, a bill, a prescription, etc.). For example, a healthcare provider can dictate a diagnosis into a progress note, which will be used not only to complete the progress note, but also to complete a bill, a claim, or a statement for the patient.

In addition, the present invention may be implemented as a plurality of integrated ambulatory suites at different healthcare practices that are networked together. By allowing the creation of such an integrated physician's infrastructure (IPI), the present invention provides functionality for analyzing, collecting, and tracking data across a vast patient population. Moreover, it provides infrastructure and functionality for utilizing that data to more effectively and efficiently perform medical research, to maintain disease registries, to track patient care for quality and safety initiatives, and to perform composite clinical and financial analytics. The same benefits of a single-vendor solution and seamless data sharing discussed above with respect to the integrated ambulatory suite are also present in the IPI.

By integrating the infrastructure and architecture of the various systems of the integrated ambulatory suite and of the IPI, the present invention provides a scalable solution that allows the various systems of the integrated ambulatory suite and the IPI to be expanded or contracted as required to suit a particular healthcare practice or healthcare community. It also allows data to be actively analyzed, collected, and tracked across a vast patient population in real time based on triggering events rather than requiring that queries be run on passive, "stale" data housed in a data repository. And by standardizing the format in which the data is captured and stored as well as the format by which it is exchanged across all of the modules and components of the integrated ambulatory suite and the IPI, the need for "middleware" type architecture to interface those various systems is eliminated. Thus, errors, duplication, and inconsistencies in data are further eliminated.

I. System Architecture

Turning to the drawings, FIG. 1 illustrates an exemplary non-limiting embodiment of the infrastructure of an IPI 100 according to the present invention. The IPI 100 is a network of computer systems comprising a plurality of EHR systems, a plurality of research systems, and at least one IPI provider system that are interconnected via a plurality of secured connections. Each EHR system is provided at a healthcare provider's site 102 (i.e., at a healthcare practice) and includes at least one client server 104 and at least one client workstation 106. Each research system may be provided at a researcher's site 108 and includes at least one partner server 110 and at least one partner workstation 112. And, each IPI provider system may be provided at the IPI provider's site 114 and includes at least one enhanced services server 116 and at least one administrator workstation 118. The EHR systems, research systems, and IPI provider system are all built on the same architecture so that the various systems of the IPI 100 and the functionality of each of their applications may be seamlessly integrated across the entire IPI 100.

A. EHR Systems

The client server 104 of each EHR system contains the integrated ambulatory suite of the present invention and controls the operation of the integrated ambulatory suite. The client server 104 also controls communications with the other systems within the IPI 100 and locally stores data collected using the integrated ambulatory suite. The client server 104 is at the center of the EHR system and may be located at a central location at a healthcare provider's site 102 for local communication with each of the client workstations 106. In the alternative, as opposed to being hosted at the healthcare provider's site 102, all of the applications, controls, and data for the integrated ambulatory suite may be remotely hosted at a client server 120 located at a client data center 122. The applications, controls, and data for the integrated ambulatory suite hosted by the client server 120 may also be utilized by different healthcare providers utilizing other EHR systems.

The client workstations 106 provide a point of communication between healthcare providers and the client server 104 of the EHR system so that users can access and utilize the various functionalities of the integrated ambulatory suite, such as via "cloud" computing. The client workstations 106 of each EHR system may be provided at various locations, remote from the client server 104, throughout the healthcare provider's site 102 (e.g., in different physicians' offices). When the client server 104 is also located at the healthcare provider's site 102, the client workstations 106 communicate with the client server 104 and with each other over a Local Area Network (LAN) via a client router 124. The client server 104 and client workstations 106 of each EHR system also communicate with the enhanced services server 116 and administrator workstation 118 of the IPI provider system via a provider router 126 provided at the IPI provider's site 114, which preferably communicates with the client router 124 via a broadband network, such as Digital Subscriber Line (DSL), cable modem, or other high-speed connection.

When the client server 120 is provided at the client data center 122, the client workstations 106 communicate with that client server 120 via a client data center router 128 at the client data center 122 that preferably communicates with the client router 124 via a private dedicated network, such as a frame relay network. In that configuration, the client server 120 at the client data center 122 and the client workstations 106 at the healthcare provider's site 102 may also communicate with the enhanced services server 116 and administrator workstation 118 of the IPI provider system via the provider router 126 provided at the IPI provider's site 114, which communicates both with the client router 124 and the client data center router 128 via the private dedicated network. The client data center router 128 is located behind a firewall 130 to provide security from unauthorized internet access. And use of a private dedicated network to facilitate the transmission of data when the client server 120 is provided at a location remote from the location of the client workstations 106 causes those components to perform like a private dedicated network and provides additional security to that network. Although the exemplary embodiment illustrated in FIG. 1 utilizes a broadband network when the client server 104 is provided at the healthcare provider's site 102 and a private dedicated network when the client server 120 is provided at the client data center 122, either a broadband network or a private dedicated network may be utilized in either configuration.

B. Research Systems

The partner server 110 of each research system contains all of the system applications and controls the operation of the research system. The partner server 110 also controls communications with the other components of the IPI 100 and locally stores data collected using the research system. The partner server 110 is at the center of the research system and may be located at a central location at a researcher's site 108 for communication with each of the partner workstations 112. In the alternative, as opposed to being hosted at the researcher's site 108, all of the applications, controls, and data for the research system may be remotely hosted at a partner server 132 located at a partner data center 134. A partner server 132 located at a partner data center 134 may also host the applications, controls, and data for other research systems utilized by different healthcare providers.

The partner workstations 112 provide a point of communication between researchers and the partner server 110 of the research system. The partner workstations 112 of each research system may be provided at various locations, remote from the partner server 110, throughout the researcher's site 108 (e.g., in different researchers' offices). When the partner server 110 is also located at the researcher's site 108, the partner workstations 112 communicate with the partner server 110 and with each other over a LAN via a partner router 136. The partner server 110 and partner workstations 112 of each research system also communicate with the enhanced services server 116 and administrator workstation 118 of the IPI provider system via the provider router 126 provided at the IPI provider's site 114, which preferably communicates with the partner router 136 via a broadband network.

When the partner server 132 is provided at the partner data center 134, the partner workstations 112 communicate with that partner server 132 via a partner data center router 138 at the partner data center 134 that preferably communicates with the partner router 136 via a private dedicated network. In that configuration, the partner server 132 at the partner data center 134 and the partner workstations 112 at the researcher's site 108 may also communicate with the enhanced services server 116 and administrator workstation 118 of the IPI provider system via the provider router 126 provided at the IPI provider's site 114, which communicates both with the partner router 136 and the partner data center router 138 via the private dedicated network. The partner data center router 138 is located behind a firewall 130 to provide security from unauthorized internet access. And, as discussed above, use of a private dedicated network to facilitate the transmission of data when the partner server 132 is provided at a location remote from the location of the partner workstations 112 causes those components to perform like a private dedicated network and provides additional security to that network. Although the exemplary embodiment illustrated in FIG. 1 utilizes a broadband network when the partner server 110 is provided at the researcher's site 108 and a private dedicated network when the partner server 132 is provided at the partner data center 134, either a broadband network or a private dedicated network may be utilized in either configuration.

C. IPI Provider System

The enhanced services server 116 of the IPI provider system contains all of the system applications used by the IPI provider to control and maintain the operation of the various systems of the IPI 100. The enhanced services server 116 also controls communications with systems outside of the IPI 100 and stores data aggregated from the various systems of the IPI 100. The enhanced services server 116 is provided at the center of the IPI 100 and can therefore serve as a centralized data repository (e.g., central database 410 of FIG. 4) for the data aggregated from the various systems of the IPI 100. Access to that repository of data is controlled by the enhanced services server 116.

The administrator workstation 118 provides a point of communication between IPI administrators and the enhanced services server 116 and other systems within the IPI 100. The administrator workstation 118 may be provided at a location remote from the enhanced services server 116 at the IPI provider's site 114. The administrator workstation 118 communicates with the enhanced services server 116 over a LAN via a provider router 126. The enhanced services server 116 and administrator workstation 118 also communicate with the client servers 104 and client workstations 106 of the EHR systems and the partner servers 110 and partner workstations 112 of the research systems via the provider routers 126 provided at the IPI provider's site 114. As discussed above, the provider routers 126 communicate with the client routers 124, the client data center routers 128, the partner routers 136, and the partner data center routers 138 of the EHR systems and research systems, respectively, via a broadband network and/or a private dedicated network. The enhanced services server 116 can control at least one internet router 140 that is used to provide the various systems of the IPI 100 access to the internet when the client server 104 or partner server 110 do not provide such access. The internet router 140 is located behind a firewall 130 to provide security from unauthorized internet access. Administrative functionality for the applications of each system in the IPI 100 can be handled through the administrator workstation 118.

D. Integration

The functionality provided at each workstation 106, 112, and 118 is implemented via a single technology platform, such as web technologies that include markup languages, programming interfaces and languages, and standards for document identification and display (e.g., HyperText Markup Language (HTML), Visual Basic Script (VBScript), Extensible Markup Language (XML), Scalable Vector Graphics (SVG), JAVASCRIPT brand language, Cascading Style Sheets (CSS), Document Object Model (DOM), Virtual Reality Modeling Language (VRML), UNIX brand language, etc.). Those web technologies are utilized to provide users of the systems of the IPI 100 with web-browser-type user interfaces for communicating with the systems of the IPI 100. Accordingly, those web technologies may be used to facilitate remote access to all of the applications and data maintained by the various servers 104, 110, and 116 of the IPI 100 within a highly secured environment and enable communication between clients, partners, and administrators. Thus, substantially any device capable of employing those web technologies can be utilized as a workstation 106, 112, and 118 (e.g., a personal computer (PC), a laptop, a tablet computing device, a handheld multimedia device, a Personal Digital Assistant (PDA), a Secure Mobile Environment Portable Electronic Device (SME PED), a smart phone, etc.).

The functionality of each server 104, 110, 116, 120, and 132 of the IPI 100 is implemented via a central processor that manages the launching of script files and controls the operation of each server. Each central processor utilizes a central service utility that runs in the background and automates tasks within each system and across all of the systems of the IPI 100. Thus, the central service utility includes two types of utilities, one that runs on the individual servers 104, 110, 116, 120, and 132 of the respective systems and one that runs across all of the servers 104, 110, 116, 120, and 132 of the IPI 100.

The central service utility utilizes an event-driven design to perform tasks by monitoring a set of directories on the various servers 104, 110, 116, 120, and 132 of the IPI 100 and identifying the presence of an event or flag file before initiating, or triggering, an associated script or application. Multiple scripts and flags can be used together to complete tasks, and each task may consist of multiple scripts and/or third party programs. An event may include an empty file, a file comprising a single line of data, or a complete data file; and a flag file contains data that indicates what task is to be performed based on the event.

The central service utility supports tasks performed by standard internet-based services (e.g., Internet Information Services (IIS) and Active Server Page Network (ASP.NET) services) and standard software-framework-based services (e.g., Component Object Model Plus (COM+) and .NET services). The internet-based services provide functionality for the robust, interactive data exchange processes of the present invention, and provide functionality for presenting data to users of the various systems of the IPI 100 in a web-browser-type format. The software-framework-based services provide functionality for centrally managing all of the business logic and routines utilized by the present invention.

Each of the servers 104, 110, 116, 120, and 132 of the IPI 100 also includes functionality for managing a relational database. Each database utilizes relational technology (e.g., a Relational Database Management System (RDBMS)) to manage all discrete data centrally, which facilitates the seamless sharing of information across all applications within each system of the IPI 100. And, by using standardized medical vocabularies to normalize data within each system of the IPI 100, information can also be shared seamlessly across the various systems of the IPI 100. That functionality reduces the potential for redundant data entry and data storage at the client server 104, 120 and partner server 110, 132 as that data is captured, and at the provider server 116 as that data is aggregated from the other servers. In addition, by storing data in relational databases, that data can be more efficiently queried to produce de-identified data sets.

To further facilitate the efficient querying of data, each database also utilizes standardized database languages designed for the retrieval and management of data in relational database, such as the Structured Query Language (SQL) and XML-Related Specifications (e.g., SQL/XML). Those standardized database languages are used to assign normalized extensions to particular types of data so that data can be more easily located within a database. And, in addition to standard extensions provided as part of those languages, those languages can also be used to define proprietary extensions unique to the system in which they are employed. Accordingly, the present invention provides functionality for storing data in a meaningful way that provides fast, easy access by any system in the IPI 100, which further enhances the data querying capabilities of the present invention.

Figure 2:
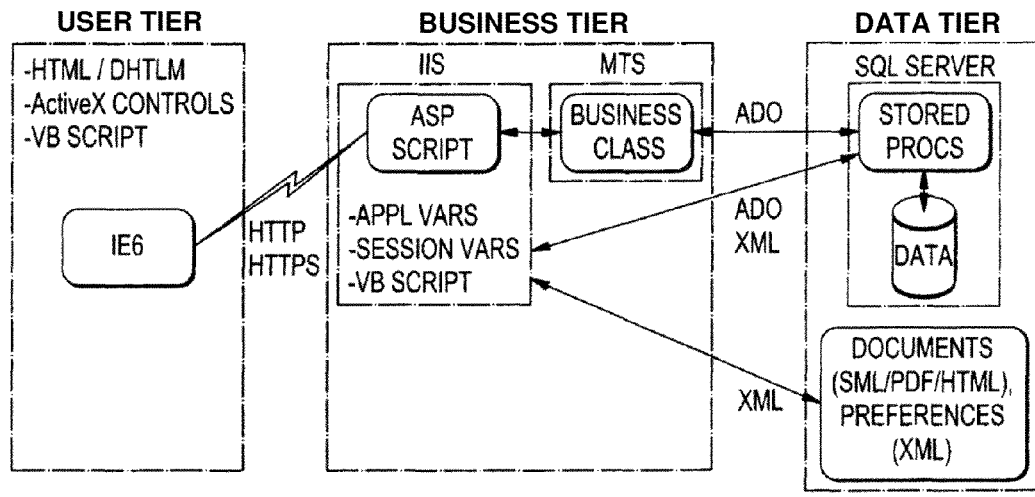
FIG. 2 illustrates the tiered architecture of the servers and workstations in the integrated physician's network illustrated in FIG. 1.

As illustrated in FIG. 2, the functionality provided at each workstation 106, 112, and 118 and each server 104, 110, 116, 120, and 132 of the IPI 100 is implemented using a tiered architecture. For example, the functionality of the workstations 106, 112, and 118 may be implemented in a user tier; the functionality of the central service utility of the servers 104, 110, 116, 120, and 132 may be implemented in a business tier; and the functionality of the databases of the servers 104, 110, 116, 120, and 132 may be implemented in a data tier. Accordingly, both a data tier and a business tier are located on each server 104, 110, 116, 120, and 132, while a client tier is located on each workstation 106, 112, and 118. In that configuration, the business tier is the middle tier and utilizes its standard internet-based services and standard software-framework-based services to analyze, collect, and track the data in the data tier and present it to a user of the IPI 100 at the user tier (i.e., at a workstation 106, 112, or 118). The business tier may access the data in the data tier using a set of computer software components provided as part of the software-framework-based services (e.g., ADO.NET), and may transmit that data to the client tier using application-level protocol for the internet-based services (e.g., Hypertext Transfer Protocol Secure (HTTPS)).

That architecture may be based on Microsoft Corporation's Distributed Internet Applications (DNA) architecture, which uses .NET objects and Web Services for business rules and COM+ for resilient database storage and retrieval. Using the DNA architecture, the user tier would utilize Microsoft Corporation's Smart Client software as the client platform; the business tier would be implemented on Microsoft Corporation's WINDOWS 2008 brand server using IIS, ASP.NET, Microsoft Corporation's Component Service, and .NET middle-tier objects; and the data tier would implement Microsoft Corporation's SQL*Server. Such a standard n-tier design model provides separation of the detailed business rules from the data storage functionality at the data tier and data presentation functionality at the user tier. That model may also make use of Microsoft Corporation's XML-based Internet architecture designs to provide a more interactive client experience through the integration of those business rules with web-browser-type data presentation. In the present invention, such architecture also provides for tighter integration of the functionality within the integrated ambulatory suited and within each system of the IPI 100.

Figure 3:
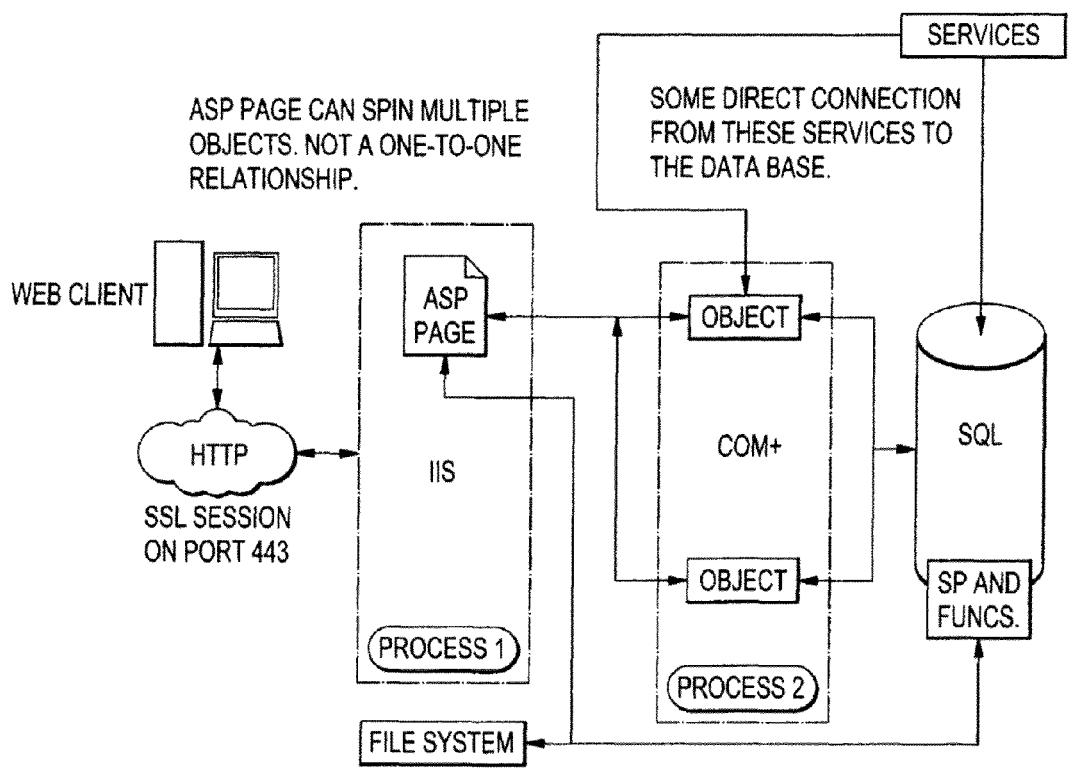
FIG. 3 illustrates the system architecture, from an applications standpoint, of a server in the integrated physician's network illustrated in FIG. 1.

FIG. 3 illustrates the system architecture from an applications standpoint. In particular, FIG. 3 illustrates the inner working of each server 104, 110, 116, 120, and 132. The "services" represent a series of service programs (e.g., Microsoft Corporation's WINDOWS 2008 brand service programs) that support and enhance the functionality of the business tier and provide operating system capabilities to the integrated ambulatory suite as well as the other systems of the IPI 100. Stored procedures and functions are two different ways of storing source code in the data tier. As illustrated, processes may be supported at either an IIS server or a COM+ server.

E. Data Standardization

To further facilitate the seamless exchange of data, each of the various systems of the IPI 100 may utilize a controlled medical vocabulary, such as the Systematized Nomenclature of Medicine, Clinical Terms (SNOMED CT). SNOMED CT is a scientifically validated collection of well-formed, machine-readable, and multi-lingual healthcare terminology that provides a standardized nomenclature for use in capturing, indexing, sharing, and aggregating healthcare data across specialties and sites of care. Because the common language employed by SNOMED CT reduces the variability in the way data is captured, encoded, and used, it is particularly suited for use in electronic medical records, ICU monitoring, clinical decision support, medical research studies, clinical trials, computerized physician order entry, disease surveillance, image indexing, and consumer health information services. SNOMED CT is currently maintained by the International Health Terminology Standards Development Organization (IHTSDO).

The present invention also utilizes other standardized medical terminologies and classification systems, such as the International Classification of Diseases (ICD), RxNorm, Logical Observation Identifiers Names and Codes (LOINC), Current Procedural Terminology (CPT), evaluation and management (E&M) codes, and Healthcare Common Procedure Coding System (HCPCS). ICD is a coded classification system for identifying the signs, symptoms, abnormal findings, complaints, social circumstances, and external causes of various injuries and diseases, and it is currently maintained jointly by the National Center for Health Statistics (NCHS) and the Centers for Medicare & Medicaid Services (CMS). RxNorm is a coded classification system for identifying clinical drugs and doses administered to patients, and it is currently maintained by the National Library of Medicine (NLM). LOINC is a coded classification system for identifying laboratory and clinical observations, and it is currently maintained by the Regenstrief Institute, Inc. CPT is a coded classification system for describing medical, surgical, and diagnostic procedures, and it is currently maintained by the American Medical Association (AMA). E&M codes are a subset of CPT codes that correspond to the non-procedural portion of services furnished during an encounter with a patient. And the HCPCS is a coded classification system that includes the CPT code set as well as a set for medical services not included in the CPT code set (e.g., codes for ambulance services, durable medical equipment, prosthetics, orthotics, and supplies), and it is maintained by CMS.

By using those standardized nomenclatures, the present invention facilitates enhanced health reporting, billing, and statistical analysis. And by mapping each of those standardized nomenclatures to the SNOMED CT vocabulary, duplicate data capture is avoided while providing a framework for managing different language dialects, clinically relevant subsets, qualifiers and extensions, as well as concepts and terms unique to particular organizations or localities. Moreover, because the integrated ambulatory suite 400 is provided on an integrated technology platform as a single-vendor solution, those codes can be quickly and easily updated throughout the integrated ambulatory suite 400 with a single data push whenever those codes are modified and/or updated by the entities that maintain them.

The present invention maintains each of those standardized nomenclatures across all of the systems of the IPI 100 in an extensive "back-end" repository so that they can not only be mapped to data captured by those systems, but can also be mapped to other widely accepted coded classification systems to further improve the functionality of the present invention. For example, ICD codes can be mapped to associated CPT codes for billing and claims processing, CPT codes can be mapped to result codes from various laboratories to facilitate lab interactions, and RxNorm codes can be mapped to First DataBank, Inc.'s NATIONAL DRUG DATA FILE PLUS (NDDF PLUS) brand coded classification system to facilitate pharmacy management and drug interaction analysis. In addition to normalizing data throughout the IPI 100 to eliminate duplicate data capture and to streamline the sharing of data, the use of all of the standardized nomenclatures discussed herein also allows the various systems of the IPI 100 to more easily mediate inbound and outbound data communications with external information systems 142 outside of the IPI 100. External information systems 142 include, but are not limited to, claims clearinghouse systems, electronic medical transcription systems, external EHR systems, external research systems, disease registry systems, public health organization systems, and safety/quality organization systems.

F. Interfacing with External Systems

When the integrated ambulatory suite 400 or any of the other systems of the IPI 100 need to interface with external information systems 142 to facilitate the exchange of data in real time, the present invention includes an interoperability engine to facilitate integration with such external information systems 142. The interoperability engine supports various standardized formats as well as various vendor-specific delimited files and fixed width files. Thus, instead of relying on distributed interfaces to various applications, the present invention provides a single platform maintained on the secure, managed network infrastructure of the IPI 100, thereby extending the seamless exchange of data across the various systems of the IPI 100 to include external information systems 142.

For example, the interoperability engine supports a uniform messaging standard, such as the Health Level Seven (HL7) messaging standard, for identifying triggering events and the associated data that is to be exchanged based on the triggering event. In the present invention, a triggering event includes an event at a client's site 102 or a partner's site 108 that creates the need for data to flow among systems, such as registering a new patient at a client's site 102 or submitting available clinical trials at a partner's site 108. Among the external information systems 142 that can be interfaced in real time using the HL7 messaging standard are EHR systems that include diagnostic equipment for capturing data at the point of care. Accordingly, the systems of the IPI 100 can exchange information such as patient demographics, processing pre-certifications, orders, results, labs, and prescriptions with external information systems 142 in real time based on triggering events. The HL7 messaging standard is utilized by most healthcare information systems, such as the hospital information systems provided by McKesson HBOC Inc., Meditech Inc., and Cerner Corp. The contents of the HL7 messaging standard are hereby incorporated by reference.

In addition to supporting a uniform messaging standard for the real-time exchange of data with external information systems 142, the interoperability engine of the present invention also supports a uniform clinical document standard, such as the Continuity of Care Document (CCD) standard, for specifying the structure and semantics of electronic documents in which data is captured. The CCD standard is a structured Extensible Markup Language (XML) standard developed by HL7 and the American Society for Testing and Materials (ASTM) to harmonize the data format between HL7's Clinical Document Architecture (CDA) standard and ASTM's Continuity of Care Record (CCR) standard. The CDA standard provides an exchange model for clinical documents (e.g., discharge summaries and progress notes) that uses various coded vocabularies (i.e., the coded vocabularies discussed above, such as ICD, etc.) to assign both computer-readable structured components and human-readable textual components to electronic documents so those documents can be easily parsed and processed electronically and retrieved, read, and understood by the people who use them. And, the CCR standard provides patient health summary model for clinical documents by identifying the most relevant and timely core health-related information about a patient so that information can be sent electronically from one healthcare provider to another. Thus, the CCD adds content to the exchange model of the CDA by using the summary model of the CCR to identify the various sections of the clinical document that collectively represent a "snapshot" of a patient's information, such as the patient's demographics, insurance information, diagnosis, problem list, medications, allergies, and care plan. Accordingly, the CCD standard supports more streamlined exchanges with and between EHR systems than supported by the CDA and CCR standards alone. The contents of the CCD standard are hereby incorporated by reference.

G. Form Management

Supported by the CCD document standard, the interoperability engine of the present invention also supports a uniform form management standard, such as the Retrieve Form for Data Capture (RFD) form management standard, to facilitate the retrieval, completion, and submission of forms between the systems of the IPI 100 and with external information systems 142. The RFD standard was developed through a joint effort between the Integrating the Healthcare Enterprise (IHE) and Clinical Data Interchange Standards Consortium (CDISC) organizations to advance public health by providing a standardized means for retrieving and submitting forms data between researchers and healthcare providers and electronic data capture systems and other data collection agencies. The RFD standard makes medical research and healthcare more efficient by providing a method for capturing data within a user's current application in a manner that meets the requirements of an external system. The RFD standard supports the retrieval of forms from a Form Manager, display and completion of a form by a Form Filler, and return of instance data from the display application to a Form Receiver and a Form Archiver.

A Form Manager is responsible for providing the desired form, such as the Food and Drug Administration (FDA). A Form Filler is responsible for inputting data into the form, such as the user of an EHR system. A Form Receiver is responsible for receiving the primary data input by the Form Filler for processing purposes. And, a Form Archiver is responsible for receiving the data input from the Form Filler for archival purposes. The Form Receiver and Form Archiver may or may not be the same entity as each other, the Form Manager, or the Form Filler. The contents of the RFD standard are hereby incorporated by reference.

In addition to facilitating integration with external information systems 142, the CCD document standard and RFD form management standard can also be utilized within each integrated ambulatory suite and within each system of the IPI 100 to facilitate the seamless exchange of data between those internal systems. Thus, the present invention provides a computer-based production environment that utilizes the CCD document standard and RFD form management standard to collect patient information in real time at the point of care using a plurality of EHR systems, both those that are part of the IPI 100 and those that are external to the IPI 100. Moreover, by facilitating the integration of external information systems 142 with the systems of the IPI 100 using the standardized formats supported by the interoperability engine, the present invention provides functionality for a researcher to collect medical data across an even larger patient population than that covered by various systems of the IPI 100.

In addition, utilizing those standardized medical terminologies and classification systems facilitates both systematic and data-level integration across each of the systems of the IPI 100 such that the research functionality of the research systems is seamlessly integrated into the workflows of the EHR systems, which eliminates duplicate data entries between the EHR systems and the electronic source documentation of the research systems. And, because the IPI 100 of the present invention includes a network of EHR systems that are built on the same architecture as the research systems, that research functionality can be employed seamlessly across the entire IPI 100 to simultaneously collect data from all of the EHR systems and electronically transfer the collected data to the research systems, which benefits all stakeholders by decreasing the input time and increasing the accuracy of data. Moreover, by providing an interoperability engine that integrates those systems with external information systems 142, the research functionality of the present invention can also be employed seamlessly across external research systems 142 to exchange data with external EHR systems and external research systems. Accordingly, that data can easily be exchanged with data from other clinicians, research institutes, universities, and pharmaceutical companies for broad-based ongoing research and can be used by researchers, scientists, and physicians to better understand and combat health issues and diseases.

H. Security

Each system of the IPI 100, as well as the integrated ambulatory suite itself, also includes features that address all of the security, privacy, and transactional regulations of the Health Insurance Portability and Accountability Act (HIPAA). To address HIPAA's security regulations, each system of the IPI 100 may include biometric login; restricted access based on login authorization (e.g., restricting access to only individual charts or chart sections); routine and event-based audits to identify potential security violations (e.g., identify who looked at what section of a chart and when); and restricted ability to copy, print, fax, e-mail, and export information based on login authority. To address HIPAA's privacy regulations, each system of the IPI 100 may include functionality for consent tracking and disclosure logging, functionality for de-identifying data, and functionality for automatically populating consent forms with the extensive details required by HIPAA explaining how a participant's protected information will be kept private. And, to address HIPAA's transactional regulations, each system of the IPI 100 may utilize Electronic Data Interchange (EDI) standards to structure the electronic transfer of claim billing information between the systems of the IPI 100 and external information systems 142, such as a claims processing system. For example, claims may be generated in the CMS-1500 or UB-04 (formerly UB-92) format using the ANSI X12N 837 transaction set when transferring claims data in an EDI environment. The contents of HIPAA and ANSI X12N 837 are hereby incorporated by reference.

By providing automated compliance with many of the requirements of HIPAA, the integrated ambulatory suite and the IPI of present invention help resolve many of the intricacies of HIPAA, which alleviates much of the concern healthcare providers have had with the complex legalities and potentially stiff penalties associated with HIPAA. In addition, by providing a system that streamlines and automates the electronic capture and flow of data between healthcare providers in a secured manner, the present invention also eliminates much of the additional paperwork and labor associated with HIPAA, which reduces the amount of cost, time, and physical space required of healthcare providers to comply with HIPAA. And, by providing a single-vendor IPI 100 comprising a large number of EHR systems that utilize an integrated ambulatory suites, the research systems of the present invention can access data for a vast patient population that can be used in clinical trials, disease registries, evidence-based medical and pharmaceutical research, and clinical and financial statistical analysis. Accordingly, the present invention makes it easier for researchers to recruit patients for research by reducing the time and costs associated with recruiting those patients, which not only overcomes many of the research related problems associated with existing paper-based processes and the regulations of HIPAA, but also provides a mechanism for healthcare providers to increase revenue and foster the ongoing improvement in quality of care for patients through their participation in the research facilitated by the present invention.

II. Integrated Ambulatory Suite

Turning to FIG. 3, an integrated ambulatory suite 400 according to a non-limiting embodiment of the present invention is illustrated. That integrated ambulatory suite 400 includes a framework module 402, an accounts receivable (A/R) management module 404, a clinical module 406, a scheduling module 408, and a central database 410. The integrated ambulatory suite 400 also includes reference databases 412 and is capable of receiving patient demographic and financial information from a legacy system database 414 by way of migration utilities that import that demographic and financial information into the central database 410. The integrated ambulatory suite 400 also is configured to communicate with a claims clearinghouse system 416 for electronically processing healthcare claims.

Each of the modules illustrated in FIG. 3 supports a different activity in a healthcare practice, including scheduling, registration, charting, account management, and reporting. The integrated ambulatory suite 400 automates each of the processes associated with a healthcare practice, from patient scheduling, to the clinical encounter, though the process of filing out, filing, and receiving payments for claims. Data captured within one area of the integrated ambulatory suite 400 flows together to facilitate a workflow process at another area of the integrated ambulatory suite 400. For example, scheduling and registration data flows to billing; registration data flows to the patient's chart; and coding, scheduling, and prescription data flow from the patient's chart to billing, to scheduling, and to the pharmacy, respectively. Thus, the integrated ambulatory suite 400 reduces the administrative burden of managing a healthcare practice and allows clinicians more time to spend with patients. It also streamlines the claims process and improves coding and the financial accuracy associated with the billing process, which ultimately maximizes a healthcare practice's profitability.

For financial activities, the integrated ambulatory suite 400 integrates coding and billing, fee schedule management, patient statements, account management, collections, electronic remittance advice, and reporting. Account management includes, for example, generating electronic charge tickets, balance tracking, charges, payments and adjustments, claims processing, claims maintenance, electronic remittance, contracts and fee schedules, insurance plans, and statements. Coding and billing includes, for example, automating coding and documentation compliance as well as fee contract analysis. That functionality assists healthcare practice managers to maximize profits and reduce coding liability by eliminating the occurrence of undercoding, reducing the risks associated with potential overcoding, and identifying instances of under-payment.

For clinical activities, the integrated ambulatory suite 400 integrates point-of-care charting, discrete data storage, administrative and clinical flags/reminders, automated lab order and prescription management, automated documentation compliance, document management, point-and-click document generation, coding assistance, summary lists, automated results management, and flowsheets.

And for administrative activities, the integrated ambulatory suite 400 integrates patient scheduling, patient reminders and alerts, a desktop interface, registration, insurance eligibility, visit check-in and check-out, reporting, audit logging, security, system setup, user preferences, and messaging.

Although the A/R module 404, the clinical module 406, and the scheduling module 408 are separate and distinct modules, they are fully integrated through the use of shared functionality in the framework module 402, such as desktop, registration, reports, audit logging, security, system setup, user preferences, alerts and reminders, and messaging functionality. To facilitate all of that integrated functionality, each of the modules and components of the integrated ambulatory suite 400 is built on the same technology platform and has pieces of code that implement the client, business, and data tiers. As discussed above, the integrated ambulatory suite 400, and therefore each of its modules and components, is centrally processed, stored, and managed by a client server 104. The client server 104 provides seamless integration between the framework module 402, the A/R module 404, the clinical module 406, the scheduling module 408, and the various components of those modules. The client server 104 also provides seamless integration between those modules and other ancillary components, including a central website portal, centralized messaging, email, and protected Internet access. A majority of a user's interaction with the integrated ambulatory suite 400 is done through robust client-side interaction via the client workstations 106, but is centrally processed, stored, and managed by the main server 10.

A. Framework Module

The framework module 402 includes various components, such as a desktop component 418, a registration component 420, a reports component 422, a messaging component 424, a visit information component 426, a system administration component 428, a communication component 430, and a help component 432. The framework module 402 supports data transmission between the various components, the A/R module 404, the clinical module 406, the scheduling module 408, the central database 410, the reference databases 412, and the legacy system database 414.

i. Desktop Component

Figure 5:
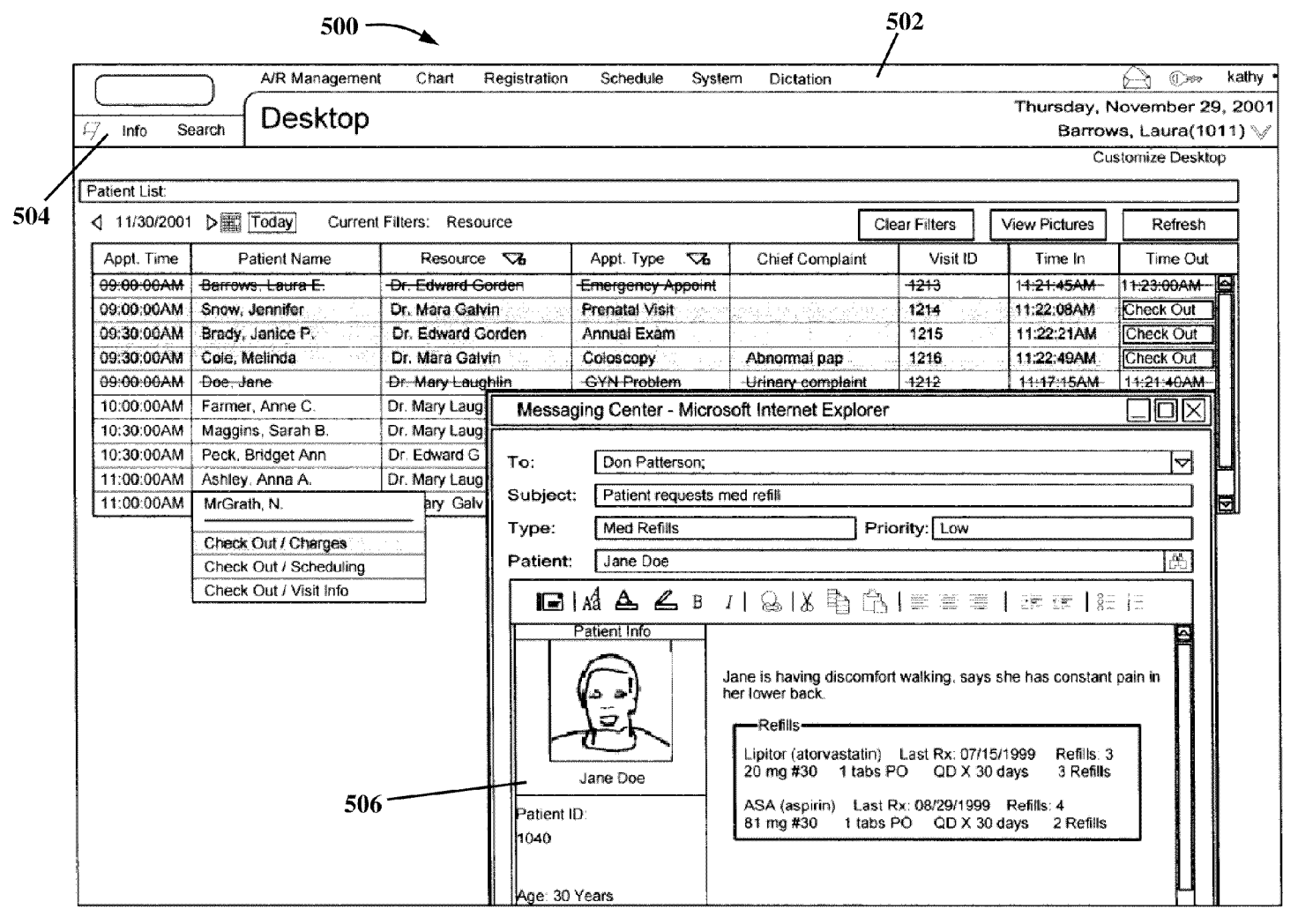

Turning to FIG. 5, a desktop 500 is shown that is supported by the desktop component 418 of the framework module 402. The desktop 500 is the main user interface that allows centralized access to each module and component within the integrated ambulatory suite 400. The desktop 500 is presented to the user at the client workstation 106 or at any other suitable user input device, such as a wireless pentop computer or personal computer that is in communication with the client workstation 106. The desktop 500 is configurable to the individual user's needs and preferences to help the user organize daily workflow and tasks. The user can view and filter scheduled patients and walk-in patients and have access to internal messaging and external applications, such as stock quotes, web access, and educational resources.

A menu bar 502 is located at the top of the desktop 500 and provides the selectable options of "A/R Management", "Chart", "Registration", "Schedule", "System", and "Dictation". The menu bar 502 also includes a messaging option in the form of an envelope icon at the top right of the desktop 500 and a security option in the form of a key icon beside the envelope icon at the top right of the desktop 500. By selecting the different options in the menu bar 502, the user is presented with a pull-down menu of additional options that allow the user to select the type of operations to be performed within the different options.

Within the "A/R Management" option, the user can check a patient's account information, charges, or e-charge ticket. The user can check a patient's payments and adjustments, such as patient transactions and insurance transactions, or check a patient's claims, such as claim maintenance, claim processing, and claim status. The user can also check the setup of the account management functionality of the integrated ambulatory suite 400, such as accounts receivable configurations, lookup tables, contracts/fee schedules, e-charge ticket configurations, insurance plans, procedures, and statements. The "A/R Management" option is supported by the A/R module 404.

Within the "Chart" option, the user can access the template administration component 1100, the template builder component 1102, and the document builder component 1104 to access, create, and edit various clinical documents. Those clinical documents are subsequently used to capture clinical information for a patient during an encounter with the patient. As used herein, clinical information, or data, generally refers symptom, observation, treatment, assessment, diagnostic, and therapeutic information. The user can also access the EHR component 1106 via the "Chart" option to capture clinical data and complete those and other clinical documents during an encounter with a patient. The user can access and complete patient charts and other clinical information, such as history of present illness (HPI), diagnosis plans, family medical histories, genetic screenings, past medical histories, past surgical histories, physical examinations, review of systems (ROS), and social histories. The "Chart" option is supported by the clinical module 406.

Within the "Registration" option, the user can access patient information, visit information, and delivery information. The user can also initiate the registration or visit check-in process for a patient. The "Registration" option is supported by the registration module 420 of the framework module 402.

Within the "Schedule" option, the user can access appointment scheduling and schedule information. Within appointment scheduling, the user can schedule patients, physicians, staff, equipment, and other resources within a healthcare practice. The "Schedule" option is supported by the scheduling module 408.

Within the "System" option, the user can access custom report functionality and security information, such as group and user administration and group rights. The user can also access setup information for the integrated ambulatory suite 400, such as care providers, communications, employers, locations, system configurations, system defaults, and visit types. The "System" option is supported by the system administration component 428, the reports component 422, and the communication component 430 of the framework module 402.

Figure 40:
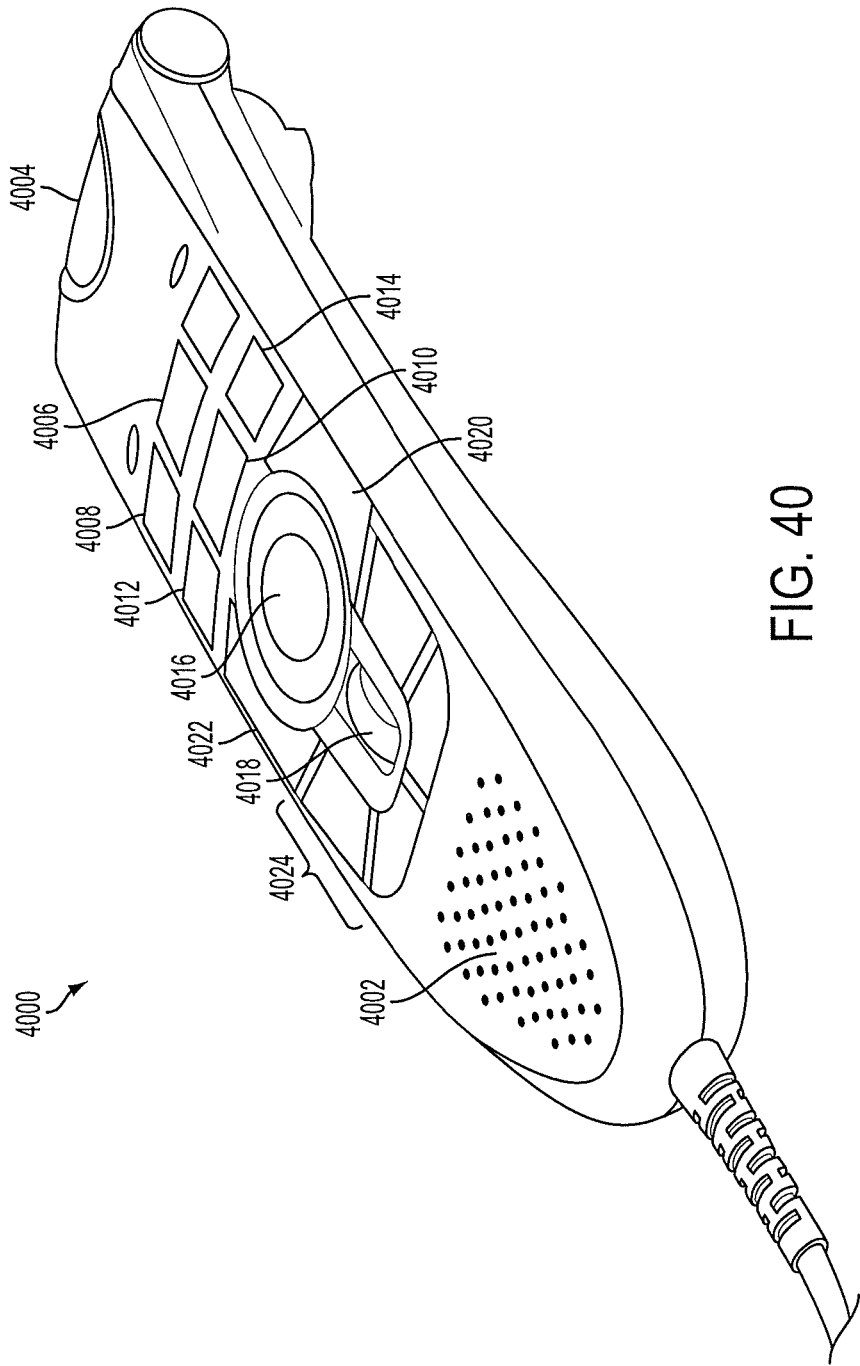
FIG. 40 illustrates a dictation microphone according to a non-limiting embodiment of the present invention.

Within the "Dictation" option, the user can use the speech understanding functionality of the present invention to dictate text into various clinical documents or into research forms. The user can also perform various tasks associated with dictating text, such as calibrating the dictation microphone 4000 (FIG. 40). The "Dictation" option is supported by each module within the integrated ambulatory suite 400 via speech understanding software embedded in the integrated ambulatory suite 400.

Within the messaging option, the user can access the messaging center. If the icon shows a piece of mail in the envelope of the envelope icon, as illustrated in the example of FIG. 5, the user has a new message. Clicking on the envelope icon takes the user to the message center. The messaging option is supported by the messaging component 424 of the framework module 402.

Within the security option, a user can change the user password. The name of the user that is logged in is displayed to the right of the key icon, which is "Kathy" in the example illustrated in FIG. 5. Clicking on the user's name allows the user to log out. The security option is supported by the system administration component 428 of the framework module 402.

A title bar 504 is displayed beneath the menu bar 502. The title bar 504 includes a flag icon, an information ("Info") button, and a "Search" button. The present day and date are displayed on the right-hand side of the title bar 504. When the user selects a patient from the "Patient List", the flag icon will appear in the title bar 504 if the selected patient has any flags checked in the patient flags modal. Then, if the flag is clicked, the patient flags modal is displayed, which indicates whether the patient has been flagged for special attention.

The patient flag modal includes both administrative flags and clinical flags that can be associated with a patient. Fields listed in the flags modal that correspond to administrative flags include: "In Collections"; "No Insurance"; "Needs Wheelchair"; "Violent"; "Excess Balance"; "Expired Insurance"; "Canceled Appointments"; "Missed Appointments"; "Statement ## Days Past Due"; "Sensitive Chart"; "Do Not Call Home"; "Do Not Release Name"; "Do Not Mail to Home"; "Need Medicare Waiver Signature"; "Restricted Chart"; "Must Select From Services Allowed"; and "See Notes", etc. And fields in the flags modal that correspond to clinical flags include: "Patient Overdue for Lab Test"; "Patient Needs Screening Colonoscopy"; "Screen Patient for High Blood Pressure"; "Patient Needs Lipid Panel"; "Patient Needs Prenatal Visits"; "Warning: Dangerous Drug/Drug Interaction"; "LDL Cholesterol Above Goal of 100 mg/dL"; "Weight More Than One Year Old"; etc. The user can select to add or remove flags for a patient, and the system can automatically create a flag, such as when the patient has an outstanding balance on their account. The use of administrative flags is discussed in more detail below with respect to the scheduling module 408. And the use of clinical flags is discussed in more detail below with respect to order management.

If the user clicks on the "Info" button, a screen is displayed with information about the selected patient, including demographic, administrative, and financial data for that patient, which is retrieved from the registration component 420 and system administration component 428 of the framework module 402. If the user updates any of the patient information, the updated information is updated at the registration component 420. The "Search" button allows the user to search for patients by name, ID number, and/or other patient-specific information.

In the example of FIG. 5, the user has configured the desktop 500 to include a listing of scheduled patients (background). In the listing of scheduled patients, each patient's check-in and check-out status is displayed (e.g., listing "11:23:00 AM" in the "Time Out" column for "Laura Barrows"). Unscheduled patients may also be displayed, depending on the search criteria by which the list was generated. The system displays the present day schedule, as well as open visits from prior days. If the user selects another date, the visits and scheduled appointments for that selected date are displayed.

The listing of scheduled patient appointments can be configured by the user, but generally includes the time of the appointment, the patient name, any scheduled resources, the type of appointment, and the chief complaint. The user can also sort the listing of scheduled appointments according to the information listed therein. In the example of FIG. 5, the listing of scheduled patients is sorted by resource.

If the user wants to access more detailed patient information, the user selects a patient, which results in the patient name being displayed at the top right-hand side of the menu bar 502. In the example of FIG. 5, that patient is "Laura Barrows". That patient's chart can then be launched from the listing of scheduled patient appointments. If the user selects the check mark to the right of the selected patient, a pull-down menu is displayed that lists recently-selected patients. If the user selects a patient from that list, the newly selected patient will be the current patient in the buffer. The user can also select patients by selecting the "Search" button from the title bar 504 to search for the patient's name.

Also in the example of FIG. 5, the user is creating a message (foreground) regarding medication refills using the messaging component 424 of the framework module 302, which is discussed in more detail below. After the user selects the patient name from the patient list, the message is automatically pre-populated with demographic information for the patient that is retrieved from the registration component 420 of the framework module 402. The message can also be pre-populated with the patient's chief complaint and current medication information from the registration component 420 and/or the clinical module 406.

The integrated ambulatory suite 400 defines different types of users, such as clinical, research, and administrative, that each have different user rights. Accordingly, the desktop 500 only displays the functions and information that are available for that particular user. For example, the desktop 500 would guide a clinical user into the "Chart" portion of the system and would guide an administrative user into the "A/R Management" portion of the system.

ii. Registration Component

The information captured by the registration component 420 can be used by any other component of the framework module 402, as well as by the A/R module 404, the clinical module 406, the scheduling module 408, and their respective components. For example, a patient's insurance coverage can be used by the A/R module 404 to generate an insurance claim and the patient's name, age, and sex can be used by the clinical module 406 to pre-populate sections in a progress note. Likewise, the information captured by the other components of the framework module 402 and by the A/R module 404, the clinical module 406, the scheduling module 408, and their respective components can be used by the registration component 420. Because each of the components and modules of the integrated ambulatory suite 400 stores data in a central database 410 in a standard format, data is replaced with updated data as it is captured so that all of the components and modules are using the most current data. That functionality also eliminates redundant data entries. Accordingly, the integrated ambulatory suite 400 can use that single source of data system-wide so that users need not enter information that has been previously captured by one component or module when working in another component or module. Instead, existing data will flow into other components and modules as required to pre-populate data entry fields so a user does not have to re-enter that data.

The registration component 420 includes visit check-in functionality to capture demographic information (e.g., name, address, date of birth, sex, digital photograph, social security number, patient ID, payor ID, insurance coverage, and credit type), financial information (e.g., financial responsibility, outstanding balances, insurance claims currently being processed, and other account information), and administrative information (e.g., scheduling information, reminders and alerts, visit check-in and check-out, and system preferences) for each patient. That information can be entered by the healthcare practice's staff, such as an office assistant, via a client workstation 106. That information can also be entered by the patient through a secure Internet link, or at a waiting room kiosk, via an interface with the client server 104. Required fields, administrative and clinical flags, and checklist procedures ensure thorough information collection for new patients, prompting the user to input specific data at each stage of the visit check-in process to ensure that the existing patient information is complete and current.

The registration component 420 also supports patient registration, including the entry of new patient information and/or importing existing patient information from the legacy system database 414. Patient-specific information, such as financial responsibility and third party insurance coverage, is also captured during the registration process. The registration component 420 stores any information obtained for new patients and information modified for existing patients in the central database 410. Registration usually takes place after the patient has scheduled an appointment, but the system will allow registration without a scheduled appointment, which is useful for healthcare practices that accept walk-in patients.

The registration component 420 allows users to associate one or more insurance plan with an employer. Users may set up information about local employers for association with patients and persons. That functionality greatly speeds up the process of entering insurance information for a specific patient. For example, a user can quickly capture a patient's insurance information by associating a patient with a specific employer insurance plan that has already been entered into the system instead of entering detailed insurance information for every patient associated with an employer's insurance plan. Insurance plan maintenance, and the addition of new plans, can be performed for a patient while accessing that patient's registration information. Thus, an insurance plan associated with an employer can be added or maintained for each patient associated with that plan by adding and or updating that plan for only one of those patients.

The user may also input pre-certification information from the insurance company or from the patient at check-in, if that information has not been previously obtained and entered into the scheduling module 408, or if that information has changed since the patient scheduled the appointment. The user also obtains information from the patient regarding the purpose for the visit (e.g., the chief complaint), if that information has not been previously obtained and entered into the scheduling module 408. The visit information, however, is not used to update the scheduling module 408, but rather any changes to the appointment information are retained for historical/tracking purposes.

Figure 6A:
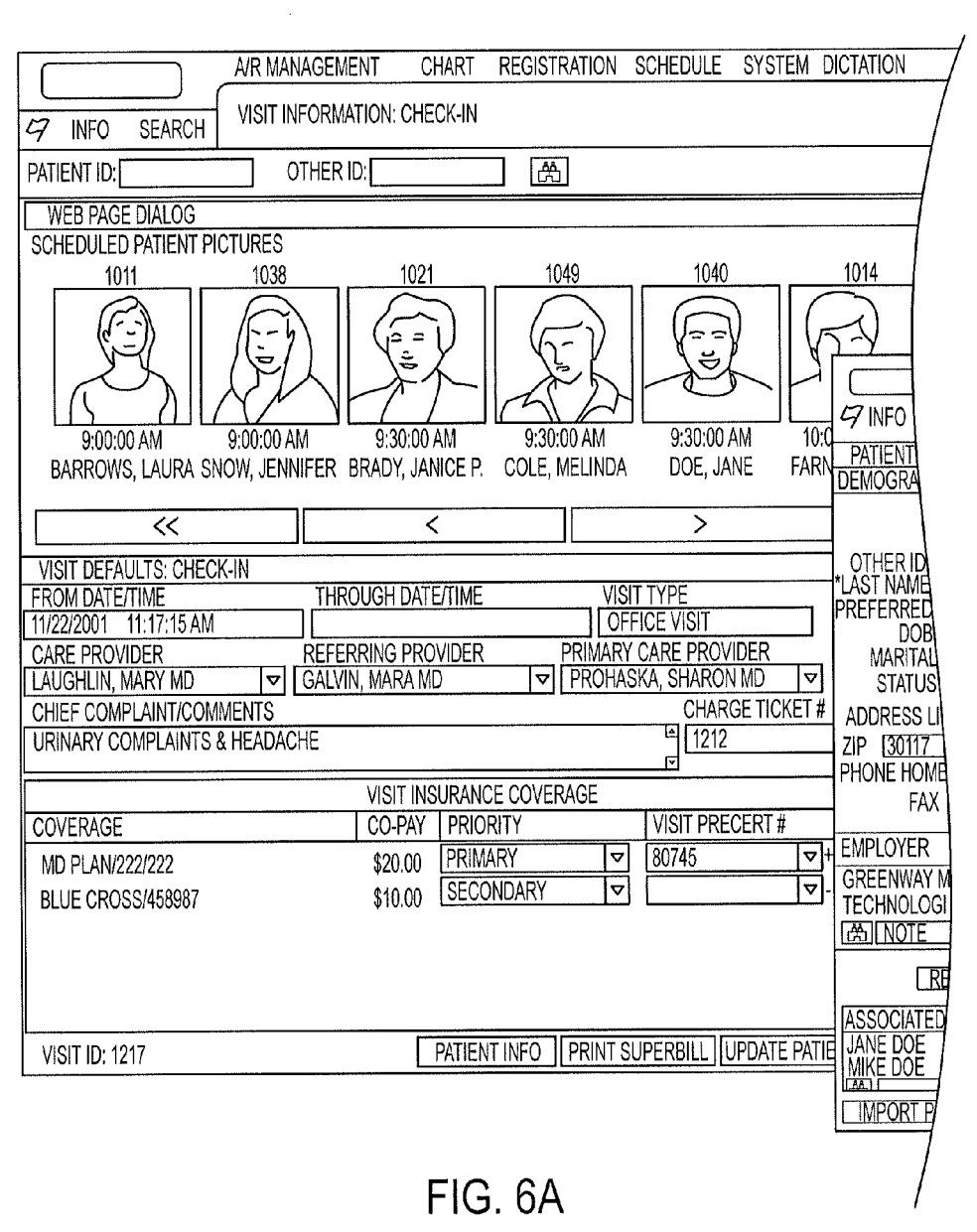
Figure 6B:
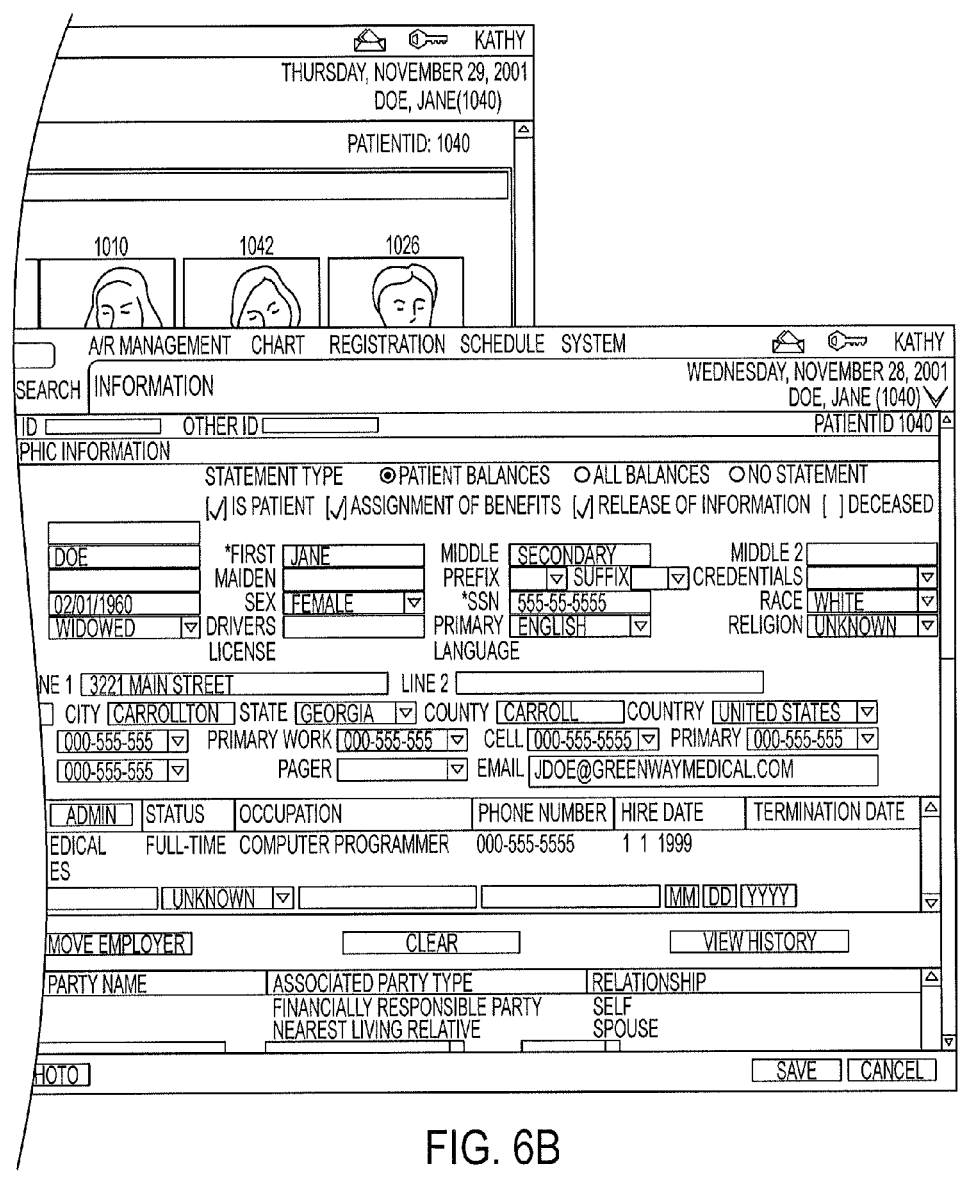

In the example of FIGS. 6A and 6B, the user has entered all of a patient's demographic and insurance coverage information into that patients information screen (foreground), including all of the CMS (Centers for Medicare & Medicaid Services—formerly the Health Care Financing Administration (HCFA)) required data as well as other useful information, such as the patient's e-mail address and digital photo. Accordingly, the registration component 420 includes patient identification and record retrieval by digital photo, which allows personal treatment of the patient as well as positive identification to prevent insurance fraud. After the patient's information is entered, the user is ready to check the patient in. And, from the visit check-in screen (background), the user can easily see important information about the patient, such as referral management information, payment collections notices, and co-pay arrangements. The system automates prior approval for referrals, admissions, orders, procedures, special medications, and other items requiring prior approval using that information.

iii. Reports Component

The reports component 422 of the framework module 402 supports the creation of all reports. The system has a standard set of reports to meet user needs that users can display, filter, and sort. Multiple filter and sort options can be saved as configured reports for future use and reference. That standard report set allows users to report on almost any combination of data within the system database via customizing options, including patients' administrative, clinical, and financial data. The user selects the sort and filter criteria for the report, such as insurance company, insurance plan, and/or billable provider, and the report is generated and displayed.

In addition to those standard reports, a report writer allows the user to modify and save existing standard reports as custom reports. A user-defined reporting tool is provided that includes a number of pre-defined datasets from which the user can choose any number of fields to create a custom report. Such custom reports can be run immediately, or in the background, sending a notice to the user via the messaging component 424 when the report is ready to view.

The user can set up the reports component 422 to generate reports as needed as well as automatically at pre-defined times, such as daily, weekly, monthly, or annually. Reports can be for any specific date or date range and can be sorted by using many different parameters, such as provider, practice, insurance plan, and patient. After a report is generated, it can be printed and exported to a variety of other file formats, such as Microsoft Company's WORD brand electronic word processor format (i.e., a .DOC file) or Microsoft Company's EXCEL brand electronic spreadsheet format (i.e., an .XLS file), for incorporation into other electronic documents.

Examples of the standard reports include: Patient Financial, such as Account Information Report; Demographic Information, such as Patient Information Sheet; Provider Productivity Analysis, such as Summary By Provider, Procedure Code Analysis Report, and Adjustment Analysis Report; Practice Statistics, such as Procedure Code Analysis Report; Referral Information, such as Referring Provider Analysis Report; Scheduling Status, such as Appointment History Report, and Daily Scheduling Report; Delinquent Accounts, such as Collection Balance Report, and Aging Account Summary Report; Insurance Claims Reporting, such as Claims Analysis Report; Audit Report, such as Audit Log Report (HIPAA Security Requirement), and Disclosure Log Report (HIPAA Privacy Requirement); Managed Care Reporting; Contract Analysis; Delinquent Accounts; Insurance Claims Reporting; and Accounting Reports, such as Account Information Report, A/R Balancing Log Balance Tracking Report, and Transaction Detail Report.

iv. Messaging Component

The integrated ambulatory suite 400 supports communication between the clinicians and other staff members at a healthcare practice from any point in the facility at any time via the messaging component 424 of the framework module 402. The messaging component 424 creates, stores, and retrieves intra-office communications. Messages can also be generated by the integrated ambulatory suite 400 to indicate situations where action is required (e.g., prescription refills). Messages will be automatically added to a patient's chart when the user chooses to "attach" that patient to the message.

The messaging module gives near real-time updates that new messages have arrived. Each client workstation 106 is in contact with the client server 104 or 120 every few seconds to check if new messages have arrived. A separate service is used instead of a web page to keep that constant "pinging" from affecting the other modules or components of the integrated ambulatory suite 400 in which a user might be working. The messaging module maintains an envelope icon on the desktop 500 that indicates when new message arrives (e.g., by illustrating a letter inside the envelope of the envelope icon). The user can then retrieve the message by clicking on the envelope icon.

As discussed above with respect to FIG. 5, when composing a message to a selected patient, the corresponding patient frame 506 overlays in the body of the message. The patient frame 506 includes demographic data for the patient, such as name, patient ID, and age. And, if there is a digital photograph available for the patient, that photo will also be displayed in patient frame 506 within the message. The message also includes a "Patient" field that will be populated with the patient's name so that the message will be associated with that patient. All messages composed and sent by the user are audit logged, indicating that the logged action was a "sent message" and recording the patient ID, the sender and the recipient, and the time of that action. That audit logging is of particular usefulness for complying with the patient data access and disclosure requirements of HIPAA.

The messaging component 424 is also provided with pre-defined response templates for common requests and routine calls and questions. Each response that is associated with a patient generates a note in the patient's chart.

v. Visit Information Component

The visit information component 426 is primarily used to track patients during a visit at a healthcare practice. In preparation for the visit, the visit information component 426 obtains information from the scheduling module 408, namely date of service, time of service, providers, and location. That information is used to pre-populate a patient's check-in screen (e.g., FIGS. 6A and 6B), and the user can fill in any missing information. The visit information component 426 is also used by the A/R module 404 to pre-populate the associated date of service, providers, locations, and insurance plans for the service details required to generate bills, claims, and statements for patients. The functionality of the visit information component 426 with respect to the A/R module 404 is shown in more detail in FIG. 7.

vi. System Administration Component

The system administration component 428 supports all administrative functions, such as setting user passwords, managing system/user settings, and controlling access to the integrated ambulatory suite 400. Administrative functions may also be supported at each of the individual modules, such as at the A/R administration component 700 (FIG. 7) of the A/R module 404.

vii. Communication Component

The communication component 430 supports all the external communication for the integrated ambulatory suite 400 and the other systems of the IPI 100, including communication with the claims clearinghouses system 416. The communication component 430 also supports the interoperability engine and form management functionality of the present invention. That functionality is discussed in more detail above with respect to the system architecture.

viii. Help Component

The help component 432 provides user support information for all the modules.

B. A/R Management Module

Figure 7:
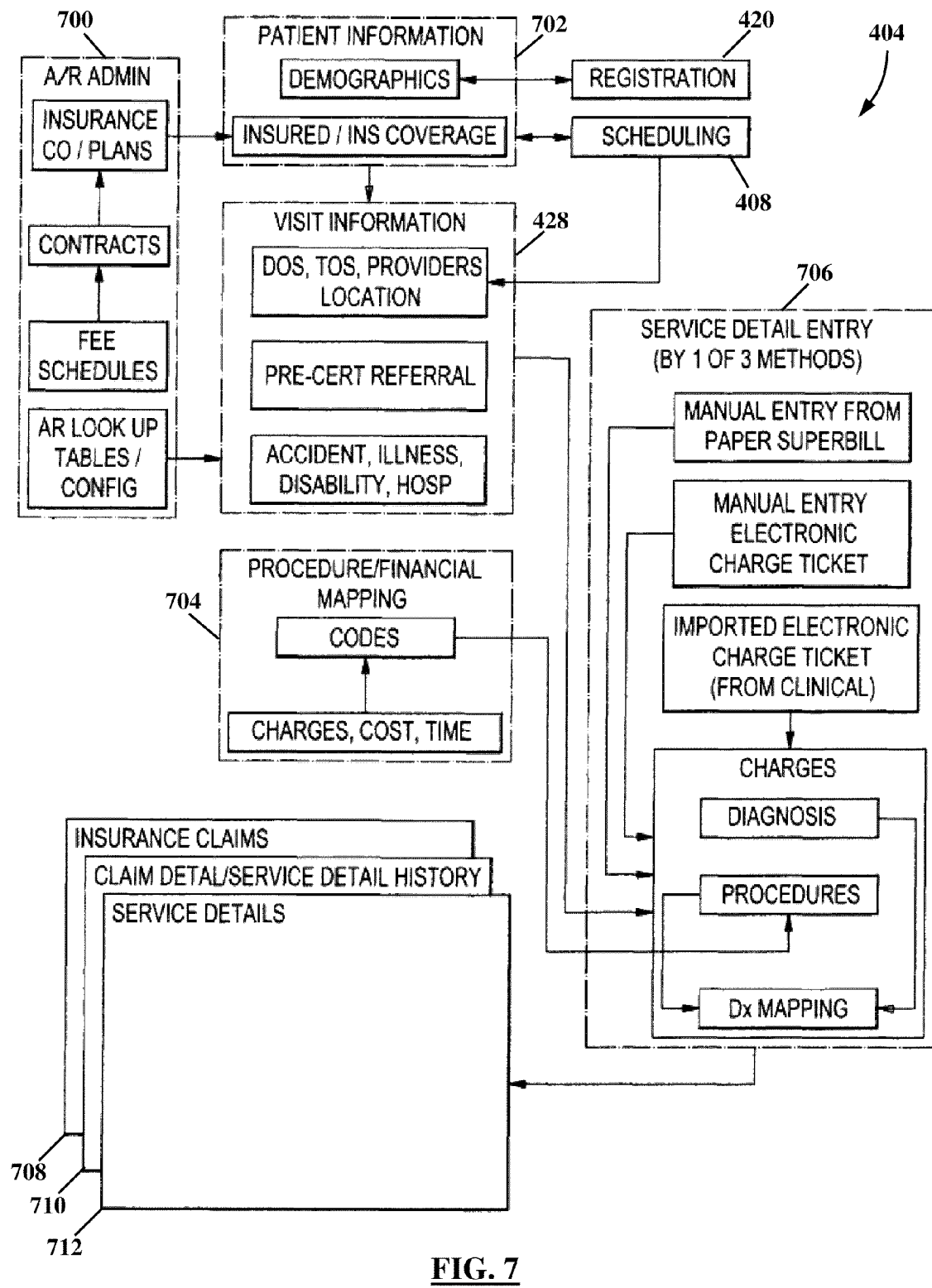
FIG. 7 is a schematic block diagram illustrating the functional makeup of the A/R module of the integrated ambulatory suite illustrated in FIG. 4.

Turning to FIG. 7, the A/R module 404 is shown in further detail, and is implemented in accordance with the architecture shown in FIG. 2. The A/R module 404 supports accounts receivable administration for a healthcare practice. The A/R module 404 summarizes patients' financial, clinical, and insurance information to produce a financial record of the patient's visit that is used in collecting payment for the services rendered during that visit.

The A/R module 404 pulls data from the registration component 420 and the visit information component 426 of the framework module 302, as well as from the scheduling module 308, to automate the accounts receivable activities of a healthcare practice. The A/R module 404 includes an A/R administration component 700, a patient information component 702, a procedure/financial mapping component 704, and a service detail entry component 706. The financial records that are generated by the A/R module 404 to collect payment for services are stored on the central database 410 in virtual file folders for each patient according to document type, including insurance claims 708, claim detail/service detail histories 710, and service details 712.

i. A/R Administration Component

The A/R administration component 700 supports administration of a healthcare practice's account management functions and communicates with the patient information component 702 and the visit information component 426, which communicate with the scheduling module 408 and the registration component 420. The A/R administration component 700 includes look-up tables and configuration information, fee schedules, contracts and insurance companies and plans. The information in the A/R administration component 700 is preferably set up by an administrator at a healthcare practice so as to be specific to the practice.

The A/R administration component 700 also includes parameters that allow accounting and claims information to be processed in "real-time" for automatic account posting and accurate reporting, or in "batch mode" for review and editing purposes. Users can also use the A/R administration component 700 to set up the A/R module 404 to properly manage billing for multiple locations using a single Tax I.D.

ii. Patient Information Component

The patient information component 702 supports the management and maintenance of patient information, including access, retrieval, and storage. For example, if a user wishes to access patient information, the patient information component 702 communicates with the registration component 420 of the framework module 402, which either stores the information in the central database 410 or retrieves it from another database 412 and/or 414. The patient information component 702 also retrieves insurance information for a patient from the A/R administration component 700.

The information retrieved from the registration component 420 and the A/R administration component 700 is presented to the user for display and manipulation at a client workstation 106 or similar user interface. For example, the patient information component 702 may pre-populate a form being viewed by the user, such as an insurance form or progress note, with the patient demographics and/or insurance information. Information that is new or updated from the patient is added via the client workstation 106 or other user interface and is sent to the scheduling module 408 and the registration component 420.

iii. Procedure/Financial Mapping Component

The procedure/financial mapping component 704 supports billing codes from the reference database 412, such as Unicor/Alpha II and CodeCorrect billing codes, as well as any charges, costs, and times that are obtained from the A/R administration component 700. The procedure/financial mapping component 704 associates procedures to the reason they were performed (e.g., diagnoses) and the charges, costs, and times for those procedures. For example, ICD and LOINC codes are mapped to the associated CPT billing codes and RxNorm codes are mapped to the corresponding drug prices in First DataBank, Inc.'s NDDF PLUS brand coded classification system. Accordingly, the procedure/financial mapping component 704 provides a reference database of procedures, diagnoses, medications, and orders and their corresponding charges, costs, and times so that such information can be used by the service detail entry component 706 to automatically post billing codes to a patient's account as a clinician completes clinical documentation (e.g., a progress note) during an encounter with a patient.

iv. Service Detail Entry Component

The service detail entry component 706 posts billing codes to a patient's account for services rendered. Information for the service detail entry component 706 may be entered by one of three methods: 1) manually from a paper superbill, 2) manually from an electronic charge ticket, or 3) electronically (e.g., electronically imported from the clinical module 406 as a clinician completes a clinical document with the EHR component 1106). A paper superbill is essentially a charge ticket that is used during checkout and/or billing and is created in response to the clinician's diagnosis and orders. An electronic charge ticket is an electronic representation of the paper superbill, which may be used during checkout and/or billing either manually or through an automatic import. And electronic input can occur via data transfer with the other components and modules of the integrated ambulatory suite 400.

For example, the service detail entry component 706 can retrieve information from the visit information component 426 and the procedure/financial mapping component 704 to generate service details for a patient. The information from the visit information component 426 is used to pre-populate the associated date of service, providers, locations, and insurance plans for the service detail being generated. And the information from the procedure/financial mapping component 704 is used to automatically post the appropriate billing codes to the service detail being generated. Thus, as a clinician completes encounter documentation (e.g., a progress note) during a patient visit, the appropriate ICD, RxNorm, LOINC, CPT, E&M, and HCPCS codes are suggested and captured. Those ICD, RxNorm, LOINC, CPT, E&M, and HCPCS codes are then automatically linked with the appropriate charges, costs, and times based on the associations made by the procedure/financial mapping component 704. The service detail entry component 706 then references the respective insurance plans, contracts, and/or fee schedules from the A/R administration component 700 to locate and enter the appropriate allowed charges into a patient's service detail entry.

The service detail entry component 706 sends information to the Unicor/Alpha II reference database 412 for validation prior to claim creation. Coding assistance is available for ICD, RxNorm, LOINC, CPT, E&M, and HCPCS codes, and warnings and alerts are based on the Medicare reimbursement guidelines to facilitate coding and billing compliance. Integrated coding edits enable the system to assist users in compliance with CMS and the National Correct Coding Initiative. Warnings and alerts based on the CMS reimbursement guidelines are displayed prior to saving the information and are available for reference purposes. For example, if a clinician uses an operating microscope during an internal neurolysis procedure, use of the operating microscope must be reported with CPT codes 64727 and 69990. And certain insurance companies will only reimburse internal neurolysis procedures under CPT code 64727 when that CPT code is submitted with one of the internal neurolysis codes on the "Services Allowed with CPT 64627" list. Accordingly, a warning to that effect will be provided to the clinician as an administrative flag (e.g., "Must Select From Services Allowed"), and that administrative flag will provide functionality for the clinician to select the appropriate internal neurolysis code from the "Services Allowed with CPT 64627" list. Such functionality helps provide improved coding accuracy, which increases a healthcare practice's revenue.

Information from the service detail entry component 706 is then used to generate an insurance claim. Upon entry of the appropriate charges, the claim is available for automatic electronic transmission. The service detail entry component 706 communicates with the clearinghouse system 416 to process the claims. The claims clearinghouse system 416 responds to claim requests with a pass, fail, or error message. That claim information is sorted and stored in the central database 310 according to insurance claims 708, claim detail/service detail history 710, and/or service details 712.

Figure 8:
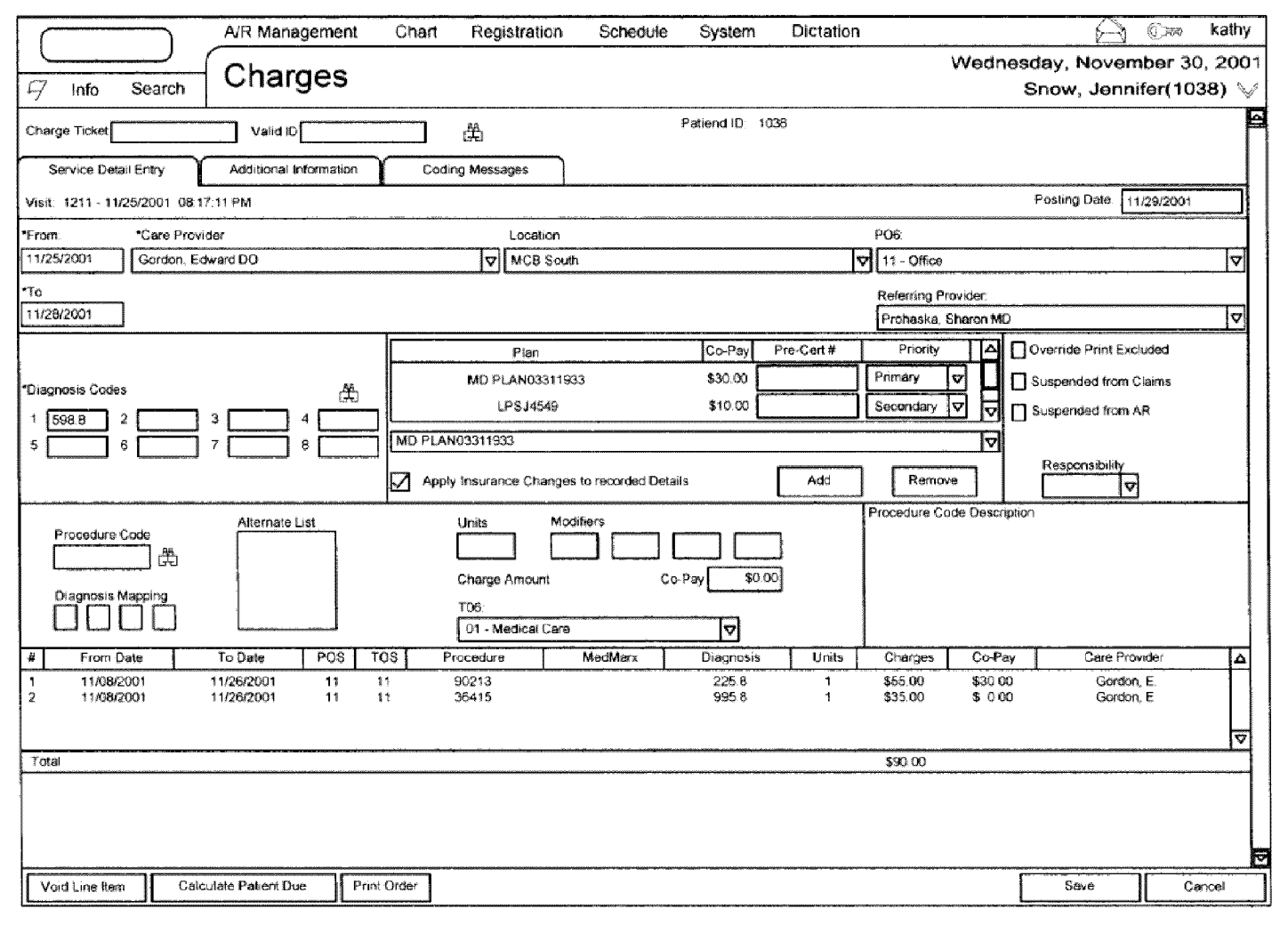

As FIG. 8 illustrates, claims and statements may consist of single or multiple pages and are automatically generated and available for electronic processing. Each claim or statement that is created contains data for only one patient and for only one visit. After charges are grouped together by patient and by visit, they are then evaluated for multi-claim or multi-page separation. After claims and statements have been created, they can be selected and edited prior to electronic submission. The system supports multiple electronic claim formats, such as the CMS-1500 or UB-04 formats using the ANSI X12N 837 transaction set. Claim payments are automatically posted and underpayment situations identified. Claims management functionality provides detailed filtering and sorting options that allow users to work with claims by insurance plan, date created, date submitted, claim priority, claim payment status, etc. That functionality provides quick access to claims information, notes and actions, as well as allowing users to view a claim as an electronic document, such as in the CMS-1500 or UB-04 form format.

Users can also search for all applicable diagnosis and procedure codes and arrange the format of a customized electronic superbill specific to the needs of the healthcare practice. When necessary, assignment of insurance coverage at the individual charge level is supported for tracking charges within a single visit that are attached to different insurance coverage. Support for tracking multiple pre-certification numbers by insurance plan is also provided, and all patient demographic and insurance information is accessible for real-time edits during charge entry.

Non-billable care providers can be attached to billable care providers to provide more accurate revenue tracking. Users may establish multiple charges and descriptions for individual ICD, RxNorm, LOINC, CPT, E&M, and HCPCS codes with defaults to streamline charge posting. Plan specific edits may be established to automate the conversion of data for specific claim generation requirements, such as type of service or modifiers.

Figure 9:

As FIG. 9 illustrates, the service detail entry component 706 retrieves the allowed amounts and contractual adjustments from the appropriate fee schedule in the A/R administration component 700 and posts them simultaneously during payment entry. Additionally, applicable contractual adjustments may be posted at the time of charge posting, or during payment entry according to the respective insurance plan setup. And should a patient's insurance coverage change, the respective allowed amounts are automatically recalculated.

In addition, contracts and fee schedules can be set up and maintained with minimal effort. For example, Medicare part B fee schedules are pre-loaded in the A/R administration component 700 and are automatically updated each year, which enables users to select the geographic region for their healthcare practice to have the corresponding fee schedule for that healthcare practice automatically identified and used to determine claim amounts. Those claim amounts are matched to the allowable amount of a contract to automatically establish the correct allowed amounts for procedures. The users can choose from several different methods to establish a variety of fee schedules, including allowed amount, percentage of charge, percentage of another fee schedule (including Medicare), etc., and to indicate which of those fee schedules should be rounded and/or capitated. Contract fee schedules are integrated into the A/R management module's 404 charge posting and payment entry functionality.

Figure 10:
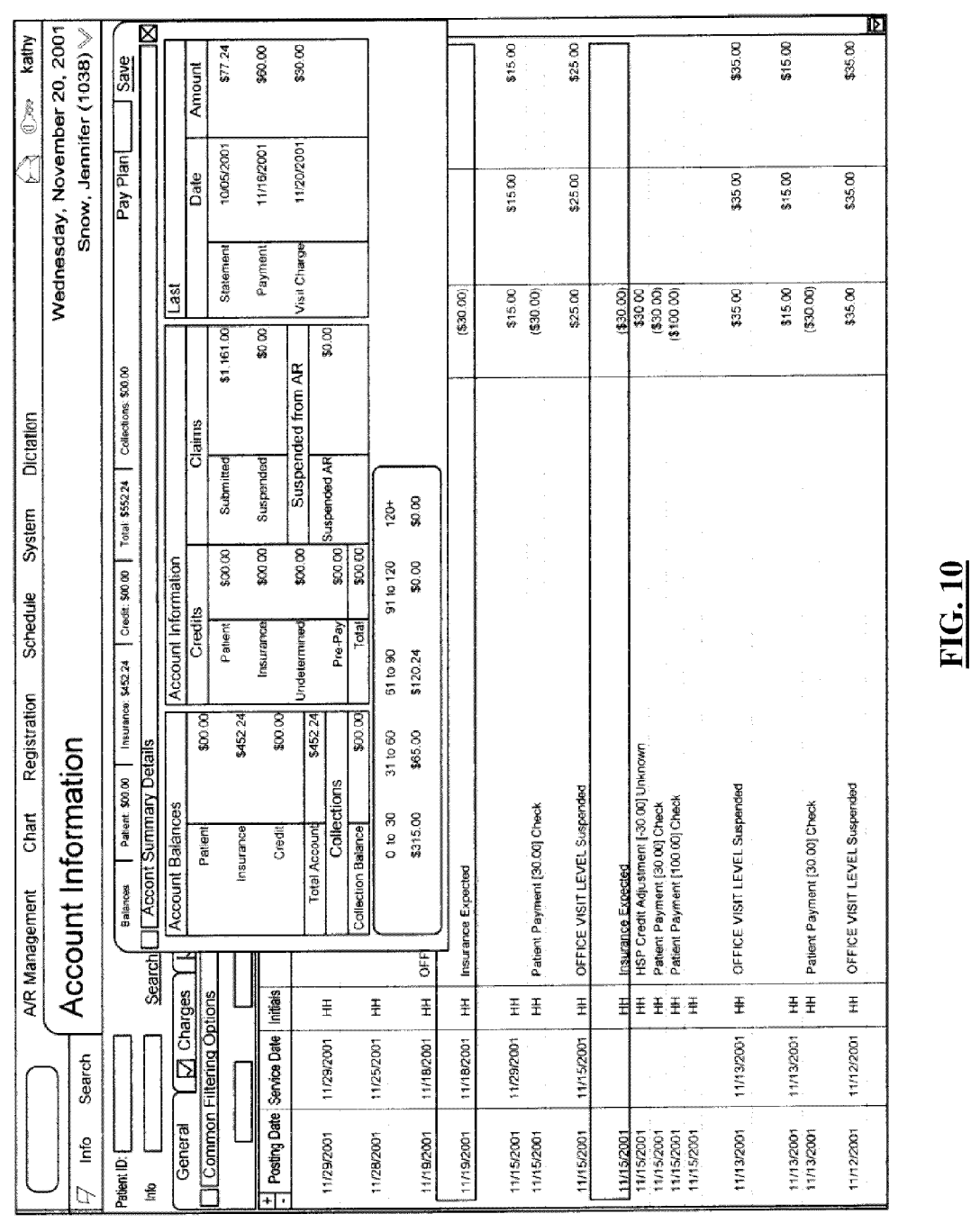

As FIG. 10 illustrates, the service detail entry component 706 provides account information in a quickly accessible format for viewing, processing, and editing purposes. That information may be provided in summary or expanded line item displays. From the account line item view, all related transactions and notes can be displayed. Account information can be viewed in chronological order by date of service, posting date, or visit order. Additionally, robust filtering and sorting options are available and can be saved for repeated use based on job function needs.

As payments are received, the A/R module 404 allows users to post payments and immediately reconcile the payments to ensure that all accounts balance properly. Credit management allows users to select a credit category for designation of payment overages or credits. The utilization of such "credit buckets" reduces the efforts required for refund processing and balance transfers by reducing the research needed for processing credit balances.

The A/R module 404 also generates collections letters and performs tracking of aged delinquent accounts and call tracking. Criteria can be defined so that accounts and claims qualify for concentrated collection and follow up activity by healthcare practice staff. Monitoring tools enable management to track and evaluate collection efforts.

C. Clinical Module

Figure 11:
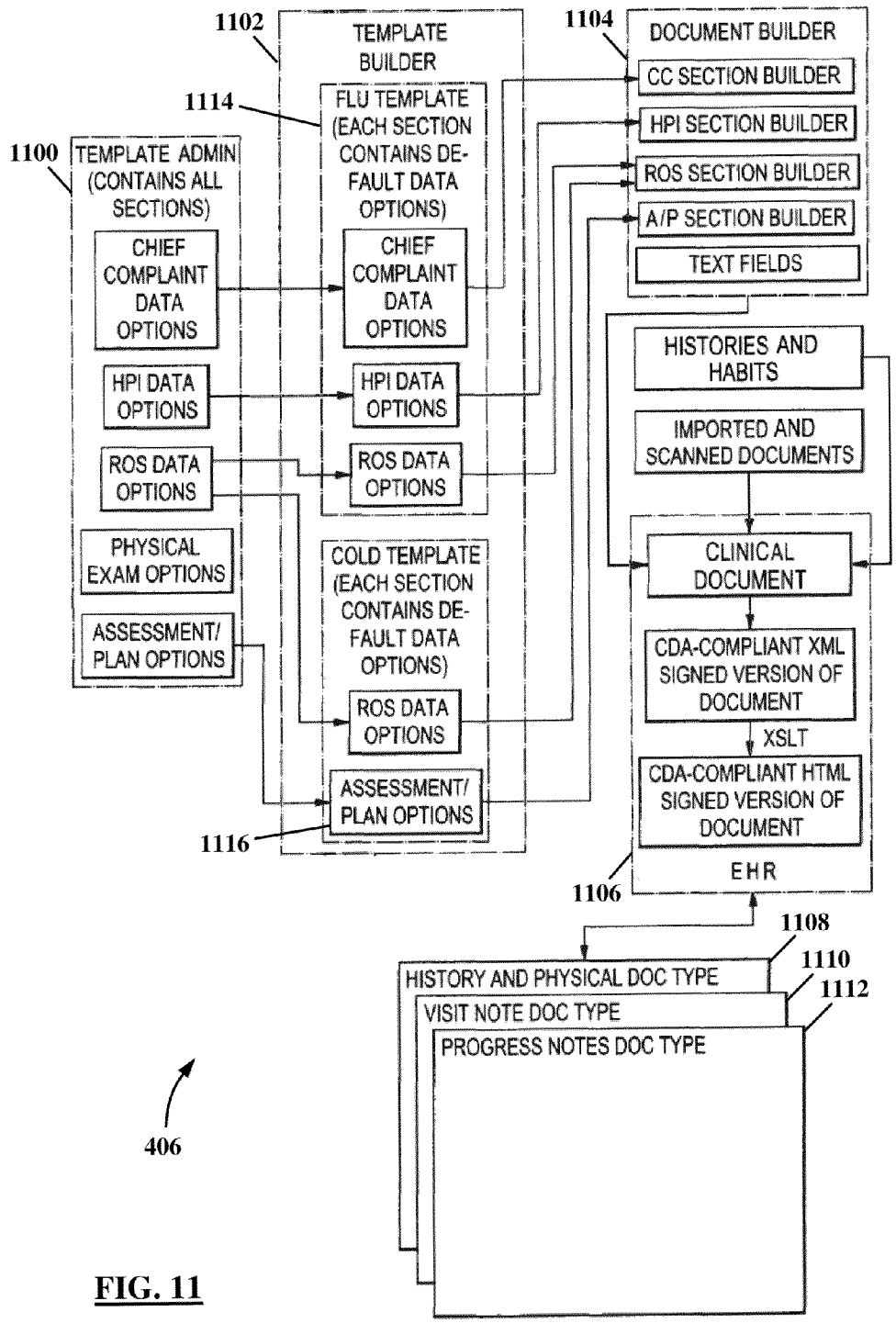
FIG. 11 is a schematic block diagram illustrating the functional makeup of the clinical module of the integrated ambulatory suite illustrated in FIG. 4.

Turning to FIG. 11, the clinical module 406 is shown in further detail, and is implemented in accordance with the architecture shown in FIG. 2. The clinical module 406 includes a template administration component 1100, a template builder component 1102, and a document builder component 1104 to build various clinical documents according to a clinician's individual needs. That clinical documentation is used to support a clinician's various activities, from when the patient arrives at the practice office until the patient leaves the practice office. The clinical module 406 also includes an Electronic Health Record (EHR) component 1106 that is used by the clinician to complete the clinical documentation for an individual patient during an encounter with that patient. Among the clinical documentation that a clinician can create and complete with the clinical module 406 is progress notes, procedure notes, consultation reports, hospital admission documents, hospital reports, history and physical (H&P) documents, triage notes, work and school excuses, and other standard communications. That clinical documentation is stored on the central database 410 in virtual file folders for each patient according to document type, including history and physical document type 1108, visit note document type 1110, and progress notes document type 1112.

Together with the desktop component 418 of the framework module 402, the clinical module 406 supports the following operations: creating clinical documentation for use in capturing clinical data during an encounter with a patient; indicating to the clinician that the patient encounter has begun by sending the clinician a message via the messaging module 424 that notifies the clinician that the patient has arrived and instructs him or her to retrieve the patient from the waiting room; automatically entering the patient's height, weight, and vital signs into the clinical documentation the clinician will complete during the encounter with the patient; reviewing and automatically updating or recording the chief complaint, allergies, current medications, past medical, family and/or social history, present illness, review of systems, miscellaneous notes; allowing the clinician to review previously entered information, including demographics and progress notes; automatically updating any patient information in the central database 410; capturing the results of a physical examination, such as the clinician's assessment; automatically coding diagnoses based on selections that were made during system setup and template building; capturing the clinician's plan; generating and documenting prescriptions and orders; capturing the clinician's treatments; selecting evaluation and management codes; generating claims, bills, and statements for processing; and closing the patient encounter.

Figure 12:
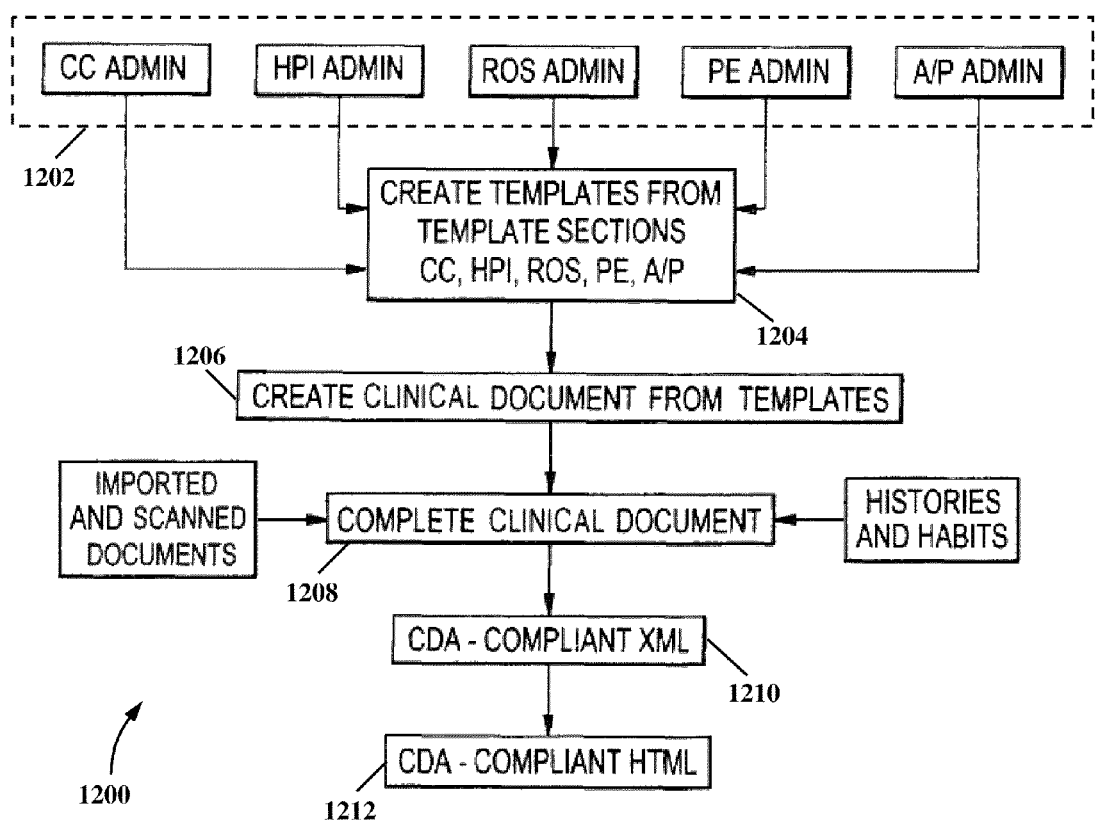
FIG. 12 is a flow chart depicting the overall operation of the clinical module illustrated in FIG. 11.

FIG. 12 illustrates the process 1200 by which the clinical module 406 is used to create clinical documentation. At step 1202, the user utilizes the template administration component 1100 to set up how different template sections are presented to the user, to define the standard content provided in each of those sections, and to perform other various administrative tasks for those sections (e.g., establishing which types of users can access and/or modify each section). At step 1204, the template builder component 1102 is used to create templates using one of the available sections from the template administration component 1100. Also at step 1204, the document builder component 1104 compiles the various sections of a clinical document from the different templates designated for that clinical document and adds text fields to the clinical document so that the clinical document complies with a chosen uniform document standard. The document is created in XML format, which is supported by the template structures.

At step 1206, the clinical document is pre-populated with various data for a patient prior to a clinician's encounter with that patient. That data is available within the integrated ambulatory suite 400. For example, the clinical document is pre-populated with data captured by other modules within the integrated ambulatory suite 400, such as a patient's demographic and financial data captured with the registration module 420 during patient check-in. The clinical document is also pre-populated with the patient's history and habit data, such as the patient's past medical history, specific condition history (e.g., cardiac history), surgical history, medications, prescriptions, allergies, family medical history, genetic screening, social history, and problems. That history and habit data may have been that may have been captured within the integrated ambulatory suite 400 as part of triage or documentation during prior encounters with the patient. In addition, any imported or scanned in documents associated with the patient (e.g., X-rays and test results) are associated with the clinical document.

At step 1208, the clinician completes the clinical document during the encounter with the patient. The sections of the clinical document generated from the templates are completed by the clinician using the functionality of the EHR component 1106 of the clinical module 406. At step 1210, the clinician signs the clinical document in the XML format. And, at step 1212, the clinical document is converted into a modified XML (e.g., HTML) format that is compliant with the chosen uniform document standard (e.g., CCD, CDA, or CCR) using predefined style sheets and Extensible Stylesheet Language Transformations (XSLT) processing.

The process 1200 by which the clinical module 406 is used to generate and complete clinical documentation is discussed in more detail below with respect to each of its various components.

i. Template Administration Component

The template administration component 1100 contains all of the various document sections that might make up a clinical document, such as the chief complaint ("CC"), history of present illness ("HPI"), review of systems ("ROS"), physical examination ("PE"), and assessment/plan ("A/P") sections. The template administration component 1100 allows the user to conduct administrative tasks for those various document sections, such as creating the sections that will be available for use in creating templates, defining how each of those sections is presented to the user, and defining the standard content provided in each of those sections. New sections can be created from scratch or existing sections can be modified to suit a user's needs. Preferably, the sections within the template administration component 1100 are created, formatted, and defined by a system administrator. A user creates, formats, and defines those sections and the standard content of those sections at step 1202 of the process 1200 illustrated in FIG. 12.

ii. Template Builder Component

The template builder component 1102 provides functionality for a clinician or other healthcare practice staff member to generate customized templates for use in generating clinical documents directed to that healthcare practice's specific needs. A template is a pre-defined set of data options that is used to dynamically generate a clinical document. Templates do not specify how sections are presented to the user, but rather the data that is utilized at the time of documentation (e.g., during an encounter with a patient). How sections are presented to the user is managed via the template administration component 1100.

Each section of a template permits the clinician to select from among a list of default data options during an encounter with a patient. The templates may be either created from scratch, created by modifying pre-defined templates, or selected from pre-defined templates. The templates can then be combined to form a clinical document (e.g., progress notes, procedure notes, consultation reports, hospital admission documents, H&P documents, triage notes, work and school excuses, and other standard communications). The clinical documents created from those templates are designed to track the manner in which a clinician and other healthcare practice staff would typically record events on paper during a patient's visit to the healthcare practice. Those clinical documents facilitate the entry of electronic data into the integrated ambulatory suite 400. The electronic data captured in those documents is retained as part of a patient's EHR. The structure of the templates ensures that a clinical document created from those templates can be converted between XML and HTML formats for use in web-based applications.

Turning to FIG. 13, the main screen of the template builder is shown. At that screen, pre-existing templates are organized in folders and displayed in a table. The user has a library of templates to choose from, with certain templates being for general use by nearly all clinicians and other templates being detailed to specialty clinicians, such as dermatologists and urologists. The user may create, import, export, delete, and rename the various templates and folders. Each template generally relates to a different type of illness (e.g., a hernia, gallstones, breast cancer, cervical cancer, a flu, and a cold). The user can also move templates between folders and place them in folders according to illness types. The user can enter the template administration component 1100 for each of the various template sections (e.g., chief complaint administration, the history of present illness administration, review of systems administration, physical examination administration, and assessment/plan administration) to perform various administrative tasks for those sections.

To build a custom template from scratch, the user selects the "Create Template" option and then identifies the type of template to be built. If the type of template is already pre-defined within the template builder component 1102, the template builder component 1102 will automatically select the sections from the template administration component 1100 that make up that template and exclude the sections that do not. For example, if a flu template 1114 (FIG. 11) is selected, the template will automatically include chief complaint, history of present illness, and review of systems sections. And if a cold template 1116 (FIG. 11) is selected, the template will automatically include review of systems and assessment/plan sections. Similarly, if a procedure note template is selected, review of symptom and physical exam sections will automatically be excluded from the template because those sections are not applicable to a procedure note.

In the alternative, the user can create a new type of template by naming the new template type and choosing which sections should be included in templates of that type. Then, the next time the user wants to create a template of that new type, he or she can choose the template by the name he or she assigned to it. Then, just as discussed above, the template will automatically include the sections the user previously chose for that type of template. After the type of template is selected, the system guides the user through the process for defining the various sections of the template.

FIGS. 15-29 illustrate an example of a template building process for a progress note in accordance with step 1204 of the process 1200 illustrated in FIG. 12. A progress note is a clinical document in which a clinician records data to document a patient's clinical status or achievements during the course of a hospitalization or over the course of outpatient care. A progress note typically includes a chief complaint section, a history of present illness section, a review of systems section, a physical examination section, and an assessment/plan section.

The chief complaint section includes a concise statement describing a patient's symptoms, problem conditions, diagnoses, physician recommended returns, and other factors that establish the reason for the clinician's encounter with the patient.

The history of present illness section includes a chronological description of the development of the patient's present illness, from the first sign and/or symptoms or from the previous encounter to the present. It may include the following HCFA recommended elements: location, quality, severity, duration, timing, context, modifying factors, and associated signs and symptoms.

The review of systems section identifies which symptoms display for which body system and in which order those symptoms display.

The physical examination section provides a worksheet or checklist for the clinician's physical examination of a patient.

And the assessment/plan section provides the clinician's diagnosis and the clinician's diagnosis-specific plans for treating the patient.

Different progress notes can be created for different types of illnesses for which a patient is being treated or examined by a physician. For example, a progress note can be created for treating or diagnosing patients with flu-like symptoms. And, because flu-like symptoms may be related to more than one type of illness, more than one type of template may be used to create the progress note for treating or diagnosing a patient with those symptoms (e.g., a flu template 1114 and a cold template 1116). A progress note generated from multiple templates will include all of the data in each section from each template of the progress note. Accordingly, the clinician will have more options in each section for diagnosing and developing a treatment plan for the patient than in the individual templates.

As FIGS. 15-29 illustrate, each of the sections within a template will appear in a navigation bar 1400 at the top of the screen at a user interface, such as the client workstation 106, when a user is working in the template builder component 1102. The user can navigate between each section in the template in any order by clicking on the corresponding text in the navigation bar 1400. The user can also navigate forward and backward from section to section in the order they are displayed in the navigation bar 1400 using navigation arrows 1402. The user can also preview and/or save the template in which he or she is working at any point by clicking on the "Preview" and/or "Save" option, respectively, in the navigation bar 1400. And the user starts the template building process by clicking the "Start" option in the navigation bar 1400. In the example of FIGS. 15-29, the first section the user will be directed to upon starting the template building process is the chief complaint section.

a. Chief Complaint Section

Figure 14:
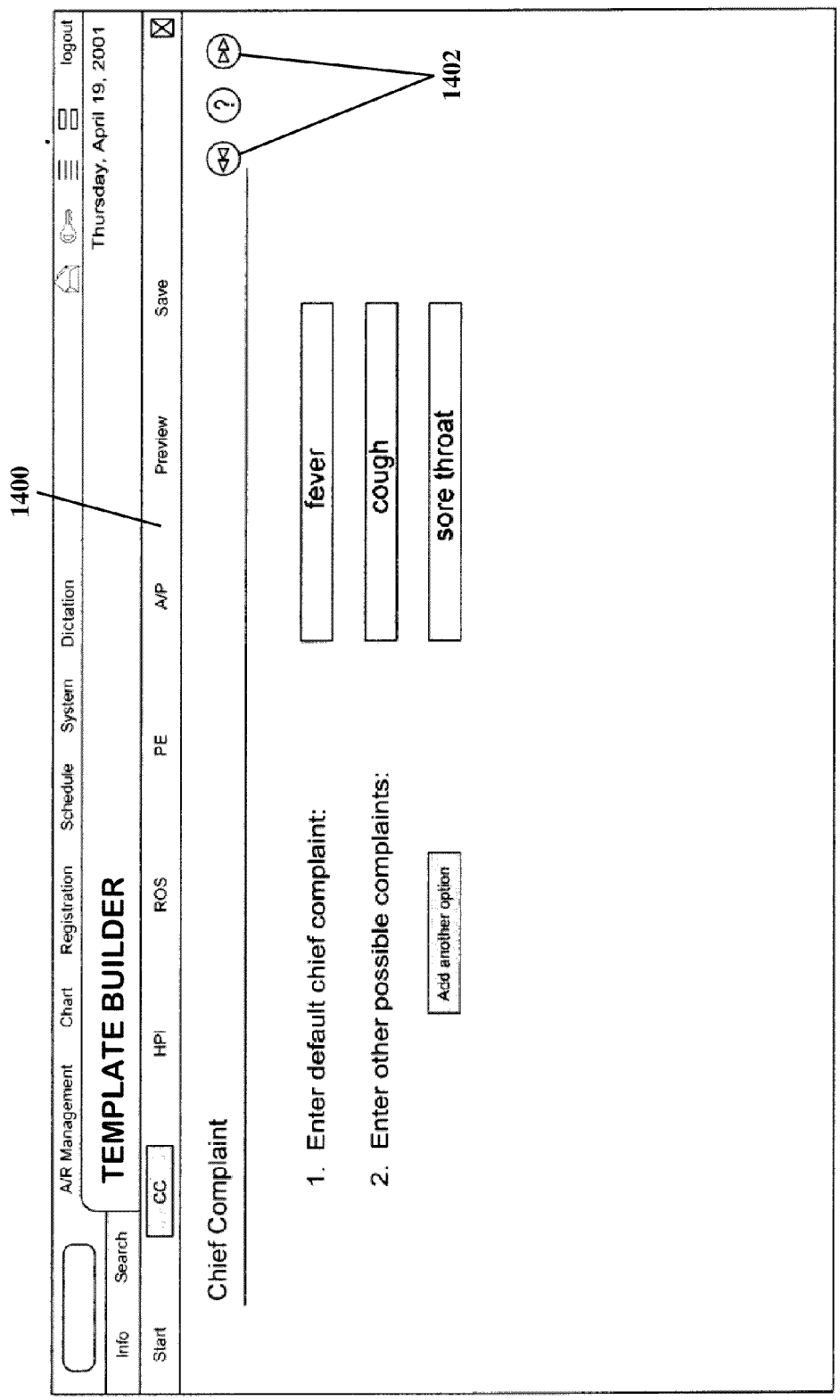
FIG. 14 illustrates an example of a template builder screen for a chief complaint section supported by the clinical module illustrated in FIG. 11.

FIG. 14 illustrates the chief complaint section for a flu template 1114. In the chief complaint section, the user defines the fields he or she wants to include in that section of the template. The template builder component 1102 allows the user to define a default chief complaint and other possible complaints. Those chief complaints will be unique to the type of template it is created within and the clinical document that the template will be used to generate. For example, those chief complaints might include fever, cough, and sore throat for a flu template 1114. The user can add additional chief complaints by clicking the "Add Another Option" button, by using the "Tab" key of a keyboard to tab out of one textbox and into another, or by a corresponding speech command (e.g., by saying "Add Another Option." into a dictation microphone 4000).

The chief complaints that will appear in the chief complaint section of a clinical document can be selected from a predefined list of chief complaints maintained by the template administration component 1100. They can also be input as freeform text by the user, such as by typing or dictation. The chief complaints maintained by the template administration component 1100 are linked to specific body systems, assessments, and plans for a patient so as to ensure those body systems, plans, and assessments appear in the other sections of the template being built, where applicable. And the chief complaints input as freeform text by the user can be similarly linked to body systems, plans, and assessments using a via a link selection tool (not shown) that is available in the chief complaint section of the template builder component 1102 and that allows the user to search the body systems, plans, and assessments maintained by the template administration builder 1100 and link them to the user-defined chief complaints.

b. History of Present Illness Section

Figures 15, 16:
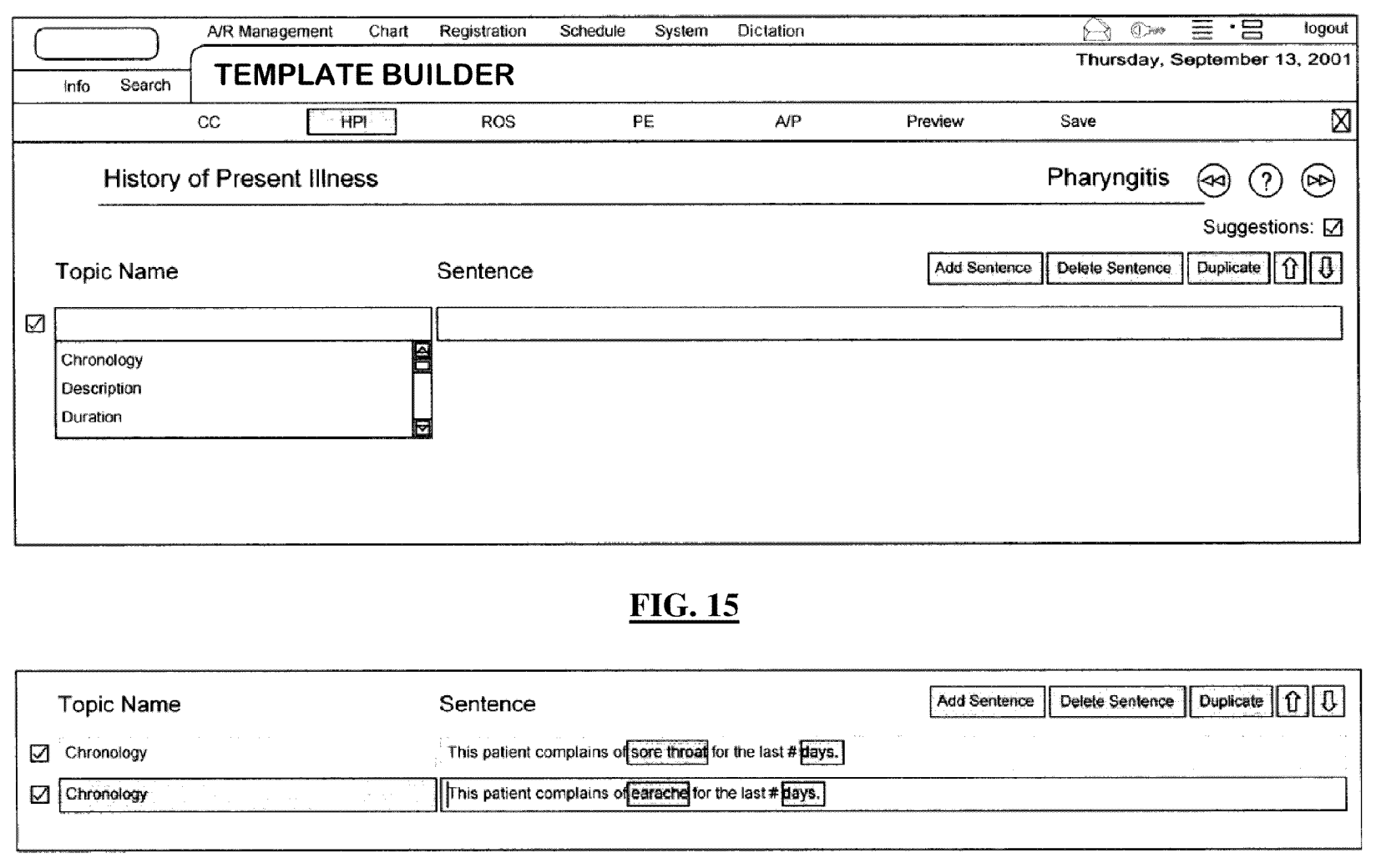

After the user completes the chief complaint section, clicking the right-most navigation arrow 1402 will take the user to the history of present illness section of the template builder component 1102, as shown in FIG. 15. In the history of present illness section, the user adds topics that may need to be addressed when a patient presents with a specific complaint or group of complaints by constructing sentences with actionable selection boxes next to them. The user may also add predefined topics with actionable check boxes. Those topics will be unique to the type of template within which they are created and the type of clinical document that the template will be used to generate.

Subjective information routinely reviewed with the patient for a particular complaint or disease process will be included in the history of present illness section. Such topics may include one of the CMS recommended element names (e.g., location, quality, severity, duration, timing, context, modifying factors, associated signs and symptoms, etc.) or one of the user's own choosing. As shown in FIG. 15, the template builder component 1102 provides a drop-down menu for the topic name field. The user can select from the defined list or type in new topics that will be displayed within the History of Present Illness section during an encounter with a patient. Specific sentences are associated with each topic name and address the associated topic.

Within a sentence, text may be selected, options such as text entry fields or drop-down boxes may be specified, and appropriate responses may be included. Other text options include patient specific demographic information (e.g., patient name, age, and sex) or gender specific pronouns (e.g., he/she, him/her, himself/herself, and his/her) that will automatically flow from the registration component 420 to populate portions of the sentence when the associated clinical document is created for a patient. As shown, for example, in FIG. 16, if the user selects the topic name "Chronology", the sentence "The patient complains of _ for the last _ _." is suggested for that topic name. And suggested elements/words for completing those sentences are automatically tagged to the sentence based on CMS reporting requirements. Those suggested sentences and elements/words are pulled in from the template administration component 1100.

The user can define control types to define text within the sentence by highlighting or selecting a phrase, as illustrated in FIG. 16. The user can also define control types for creating entire sentences from scratch. When a phrase is selected within a sentence, a list of available control types is displayed for selection by the user. Control types include, for example, demographic information, date stamp, care provider list, duration, number selector, measurement, make multiple select, make select list, and make input box. The different control types are color coded for easy reference.

The demographic information control type attaches the text "age/race/sex" control to this point in the sentence. The gender-specific pronouns (e.g., he/she, him/her, himself/herself, and his/her) may also be placed in sentences as a demographic control type. Those control types are used to designate a point where the correct gender-specific pronouns will automatically default into the sentence. Accordingly, when the clinical document built from the template is being completed with the EHR component 1106, the patient's age, race, and sex will automatically populate the corresponding fields, as will the appropriate pronouns.

The date stamp control type allows the user to create a point in the sentence where the time and/or date of the patient encounter will automatically be input when the resulting clinical document is completed during a patient encounter. The time and/or date may be obtained from the internal clock of any device on which the integrated ambulatory suite 400 is being implemented (e.g., the internal clock of the client server 104).

The care provider list control allows the user to create a point in the sentence where a care provider (e.g., Sharon Prohaska MD, Galvin Mera MD, Mary Laughlin MD, Edward Gordon DO, etc.) can be selected from a pull-down menu. Using the template builder component 1102, the user selects the care providers that will appear in the pull-down menu from a predefined list of care providers maintained by the template administration component 1100. In the alternative, the user can select a single, specific care provider from the predefined list whose name will automatically be populated at that point in the sentence.

The duration control type allows the user to create a point in the sentence where a duration of a symptom (e.g., hour, day, week, month, etc.) can be selected from a pull-down menu. Using the template builder component 1102, the user selects the durations that will appear in the pull-down menu from a predefined list of durations maintained by the template administration component 1100. In the alternative, the user can select a single, specific duration from the predefined list that will automatically be populated at that point in the sentence.

The measurement control type allows the user to create a point in a sentence where a unit of measure (e.g., inches, millimeters, pounds, ounces, C.°, F.°, mmHg, etc.) can be selected from a pull-down menu. Using the template builder component 1102, the user selects the unit of measure that will appear in the pull-down menu from a predefined list of units of measure maintained by the template administration component 1100. In the alternative, the user can select a single, specific unit of measure from the predefined list that will automatically be populated at that point in the sentence.

The number selector control type allows the user to create a point in the sentence where a number (e.g., 1-9) can be selected from a pull-down menu. Number selector control types can contain a single digit and be placed side by side as required to allow numbers with multiple digits to be input, or they can contain multiple digits. It will be advantageous to use the former configuration when the range of possible numbers that might be input into that point in the sentence is large (e.g., 1-10,0000), and it will be advantageous to use the latter configuration when the range of possible numbers that might be input into that point in the sentence is small (e.g., 100-150). Using the template builder component 1102, the user selects the configuration of the number selector control type as well as the range of numbers that will appear in the number selector control type.

The make multiple select control type allows the user to create a point in the sentence where a freeform list of choices can be provided in a pull-down menu. Instead of selecting choices from a predefined list maintained by the template administration component 1100, the user can define the different choices with freeform text input using any suitable input device, such as a keyboard or a dictation microphone 4000 (FIG. 40). Using the template builder component 1102, the user can create the different choices from scratch or modify a predefined list of choices maintained by the template administration component 1100. Such new and modified lists can be named and saved for use in subsequent template building processes. They will be available to all types of templates in the future, not just the type of template being created or edited at that time.

The make select list control type allows the user to create a list of sentence options that can be applied to other control types within the sentence. Those sentence options give more details about the sentence contents by automatically generating other sentences that branch of a main sentence based on the user-selected input into the main sentence. For example, if the user selects a "Yes" option from a pull-down menu when a patient responds positively to the question "Have you ever had these symptoms before?", then the progress not may be automatically populated with follow-up questions for the clinician, such as "How long ago?" and "What treatments were used?" And if the user selects a "No" option from a pull-down menu when a patient responds negatively to the initial question, the follow-up questions will not appear.

The make input box control type allows the user to create a point in the sentence, or to create a sentence from scratch, using freeform text input by the user using any suitable input device, such as a keyboard or a dictation microphone 4000 (FIG. 40). A clinician or other healthcare practice staff member can input freeform text into the make input box in the clinical document created from the subject template, such as during a registration process or an encounter with a patient. The make input box control type is particularly suited for places in a clinical document where predefined selections and/or sentences are not practical.

The control types that allow the user to selected from a list maintained by the template administration builder 1100 (e.g., care provider list, duration, measurement, and number selector) will already be linked to any associated data that may be used elsewhere in the integrated ambulatory suite. For example, a "Yes" response to a certain question may be linked to a specific type of clinical flag. And, the control types that allow the user input user-defined selections (e.g., make multiple select and make select list) may be linked by the user to any associated data that may be used elsewhere in the integrated ambulatory suite while the user is inputting those selections. For example, a selection related to a specific diagnosis may be linked to several different potential diagnoses so that those potential diagnoses are listed as choices in the Plan Section of a clinical document. Those user-defined selections can be similarly linked to body systems, plans, and assessments via a link selection tool (not shown) that is available in the history of present illness section of the template builder component 1102 and that allows the user to search the body systems, plans, and assessments maintained by the template administration builder 1100 and link them to the user-defined selections. The selections in the history of present illness section are linked to specific body systems, assessments, and plans for a patient to ensure that those body systems, assessments, and plans appear in the other sections of the template being built, where applicable.

c. Review of Systems Section

Figure 17:
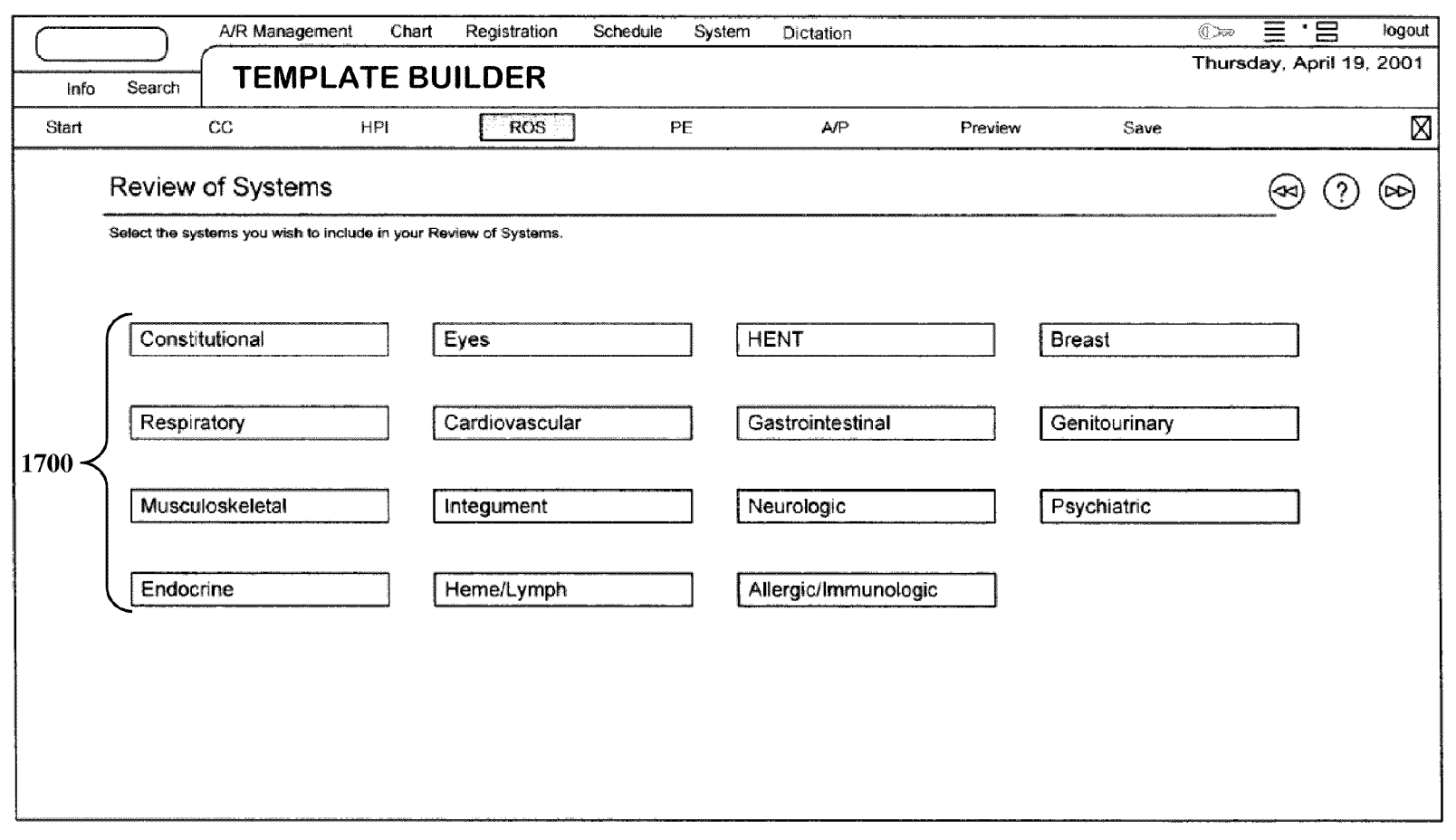

After the user completes the chief complaint section, clicking the right-most navigation arrow 1402 will take the user to the review of systems section of the template builder component 1102, as shown in FIG. 17. In the review of systems section, the user selects which symptoms and/or modifiers 1800 (FIG. 18) will be displayed for each body system 1700 and in which order Like the selections for the history of present illness section, those selections will be unique to the type of template within which it is being created and the type of clinical document that the template will be used to generate.

The default body systems 1700 appearing in the review of systems section may include those defined by CMS (e.g., constitutional; eyes; head, ears, nose, and throat (HENT); neck; chest; cardiovascular; breasts; gastrointestinal; genitourinary; lymphatic; musculoskeletal; skin; neurologic; and psychiatric) or any other widely accepted body system identifiers. All body systems 1700 and associated symptoms and/or modifiers 1800 will be available to all templates, not just specific types of templates. But, during the template building process, only the body systems 1700 corresponding to the specific type of template being built may be displayed for selection. Those selections may be broadened or narrowed by selections that were defined in the other sections of the clinical document for which the template is being created. For example, selections related to chest pains in the chief complaint section and history of present illness section may be linked to the chest body system 1700 and, more particularly, to specific symptoms and/or modifiers 1800 within that body system. Accordingly, that body system 1700 and those symptoms and/or modifiers 1800 will be presented for selection in the review of systems section during the template building process.

After the user selects the desired body systems 1700 for the template, the user will navigate to the next page and select the symptoms 1800 associated with those body systems that may be reviewed with the patient during an encounter with that patient. For each of the body systems 1700 selected from the inventory, one or more symptom and/or modifier 1800 is displayed, as illustrated in FIG. 18. The modifiers provide additional detail for the symptoms.

Standard sets of symptoms and/or modifiers 1800 are provided by the template administration component 1100 as comprehensive listings for each body system 1700 so as to provide a general review of each body system 1700. Users can choose symptoms and/or modifiers 1800 from the standard sets that will appear in the clinical document. Users can also add new symptoms and/or modifiers 1800 into a template according to his or her practice needs. Any symptoms and/or modifiers 1800 added to the review of systems section will be available to all types of templates in the future, not just the type of template being created or edited at that time.

The user can also define the default settings for a symptom and/or modifier 1800 to appear neutral, negative, or positive. That allows the user to more quickly document the findings by eliminating the need for the clinician to input data during the encounter when the default setting corresponds to the symptom observed.

The selections within the review of systems section can be linked to plans and assessments via a link selection tool (not shown) that is available in that section of the template builder component 1102 and that allows the user to search the plans and assessments maintained by the template administration builder 1100 and link them to those selections. The selections in the review of systems section are linked to assessments and plans for a patient so as to ensure that those assessments and plans appear in the other sections of the template being built, where applicable.

d. Physical Examination Section

Figure 37:
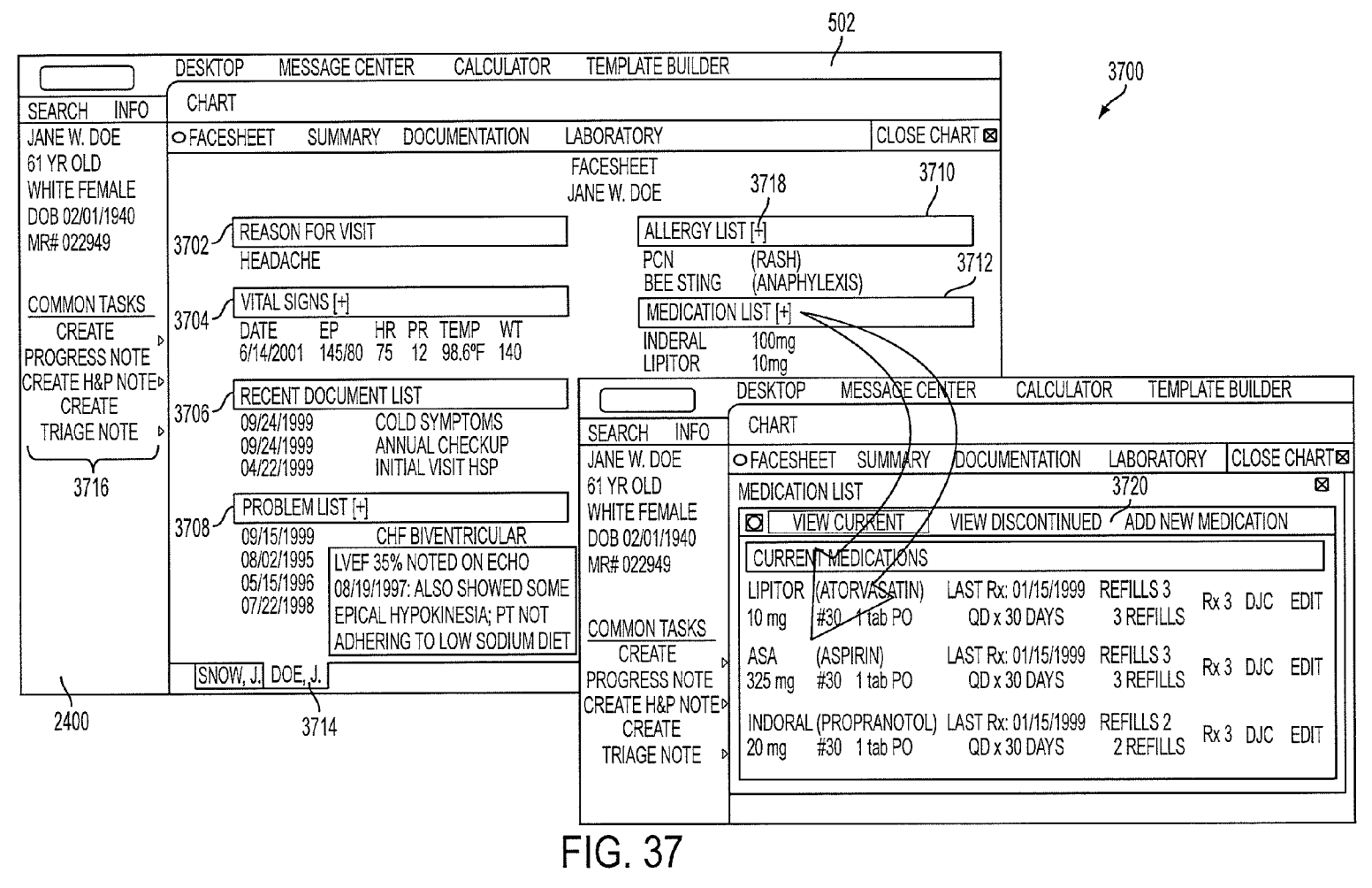

After the user completes the review of systems section, clicking the right-most navigation arrow 1402 will take the user to the physical examination section of the template builder component 1102. The physical examination section can also be accessed from the desktop 500 (FIG. 5) or the facesheet 3700 (FIG. 37). In the physical examination section, the user configures a page that will be used as a worksheet or checklist for a clinician's physical examination of a patient during an encounter with the patient. The type of physical examination set forth in the physical examination section will correspond to the chief complaints, history of present illness, and review of systems defined in the previous sections.

The physical examination section provides a system tree 1900 that includes a list of body systems 1700 that will be examined as part of the physical exam. That list of body systems 1700 serve as the clinician's guideline or checklist during the physical examination of the patient. A corresponding list of categories 1902 is provided in the system tree 1900 for each body system 1700. The user can view those categories 1902 by expanding a specific body system 1700, such as by clicking on a "+" beside the body system 1700. As with each body system 1700, each category 1902 can also be expanded to view another level of subcategories 1904 displayed beneath it. Although only one subcategory 1904 is discussed, the subcategories 1904 within each category 1902 can be created to greater and greater levels within a physical examination section. The template builder module 1102 will support as many levels as the user wishes to create.

Figure 19:
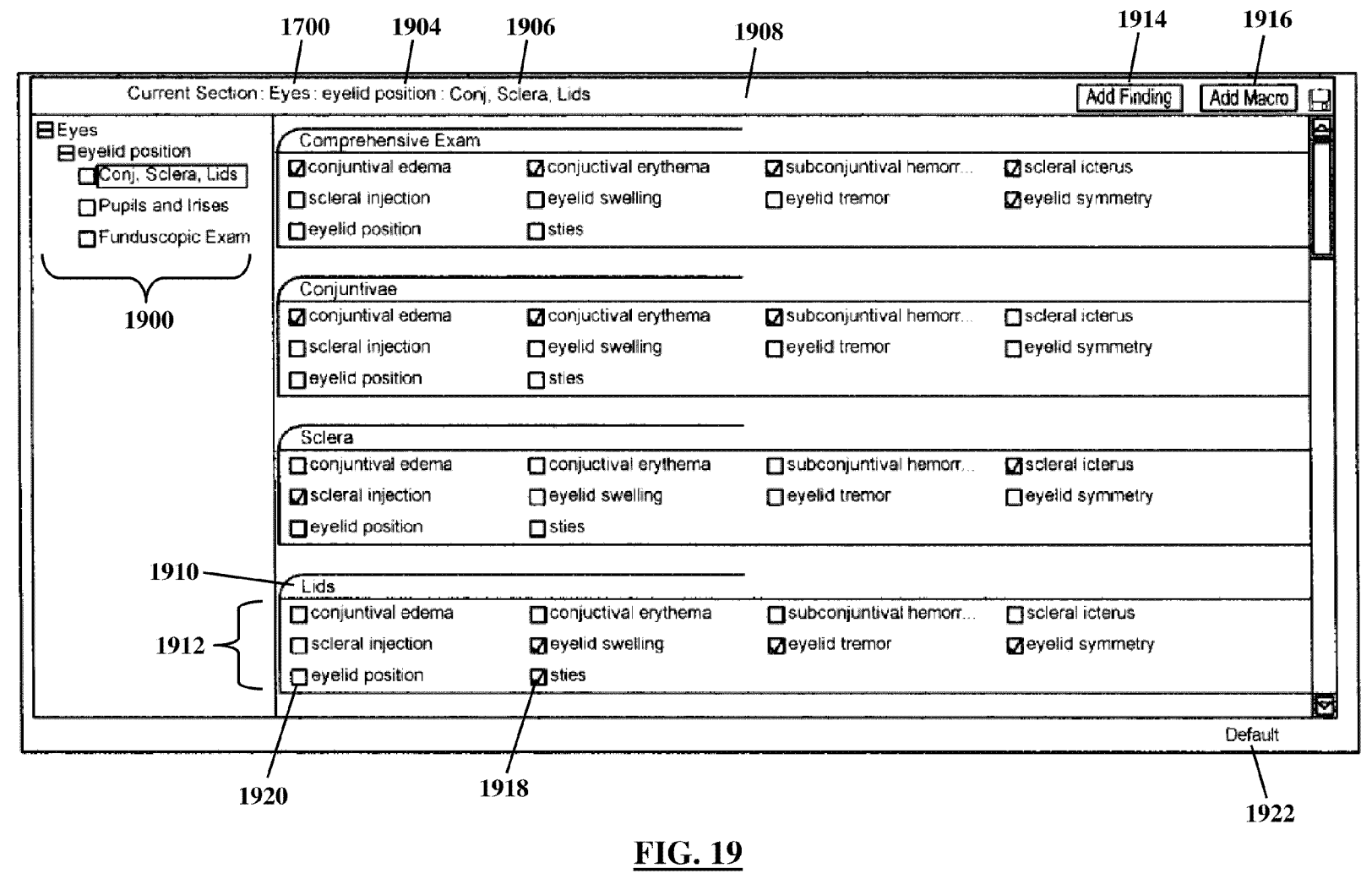

In the example illustrated in FIG. 19, the user has chosen the body system 1700 "Eyes", which is displayed in a title bar 1906. Within that body system 1700, the user has selected the category 1902 "eyelid position," which is also listed in the title bar 1906. That category 1902 has four subcategories 1904 associated with it: "Comprehensive Exam", "Conjunctivae", "Sclera", and "Lids", which are also listed in the title bar 1906. Each of those items is also listed in the system tree 1900, which the user can utilize to navigate between the various systems, subcategories, and locations by expanding and collapsing them and selecting the body system 1700, category 1902, or subcategory 1904 for which the user would like to view more detail.

At the highest level detail, one or more macro 1908 is listed. Each macro 1908 includes one or more corresponding finding 1910. The user can add new macros 1908 and/or findings 1910 to the selected subcategory 1904 by using the "Add Finding" button 1912 and "Add Macro" button 1914, respectively, in the title bar 1906. The user is then presented with a list of the current macros 1908 or findings 1910, and can add, delete, reorder, or edit any of them as desired.

To create a guideline or checklist for the clinician's use during a physical examination, the user selects those findings 1910 that the user would like displayed in the clinical document that will be used during the encounter with the patient. Only the selected findings 1916 will be displayed in the clinical document. The unselected findings 1918 will not be displayed in the clinical document.

After the user selects one or more findings 1910, the user is presented with a list of defined values for each selected finding 1916. Those values are listed in the order that they will be displayed in the clinical document. The user can select one or more of the displayed values to be the default value for the finding 1916 and can add, delete, reorder, or edit any of the displayed values. The selected values will appear in the clinical document when a clinician selects the finding 1916 during an encounter with a patient. The user can then select the values that are appropriate to be added to the document being built, or can add, delete, or edit those values. An example of a value would be the value "0.5" for the finding "eyelid symmetry," which would be displayed in the clinical document and would allow the user to specify a value for an eyelid symmetry measurement.

The user can also associate one or more modifiers to any of the findings 1916. The modifiers are listed according to categories, such as measurements, locations, and descriptions. The user can add, delete, or edit the categories and modifiers. The user can also return the body systems 1700, categories 1902, subcategories 1904, macros 1908, findings 1916, values, and modifiers back to their default settings at any level of detail by selecting the "Default" option 1920 at the bottom of the screen at which the selected level of detail is being displayed. An example of a modifier would be "inches" for the finding "eyelid symmetry," which would be displayed in the clinical document and would allow the user to specify the eyelid symmetry measurement in inches. Accordingly, the clinician can specify both the value and units of measurement for the "eyelid symmetry" finding.

As discussed above with reference to the A/R module 404, the service detail entry component 706 automatically links E&M codes with the appropriate billing codes as a clinician completes a clinical document during an encounter. To facilitate that automated process, each of the findings 1916 that can be selected during a physical exam are linked to E&M codes. The standard findings 1910 that are provided by the template administration component 1100 are already linked to the appropriate E&M codes. And when the user adds his or her own findings 1916, those findings will also be linked to the appropriate E&M codes based on the subcategory 1904 in which they appear. The user may also link his or her added findings 1916 and subcategories 1904 to a controlled medical vocabulary (CMV), such as the SNOMED CT CMV, via a CMV selection tool (not shown) that is available in the physical exam section and allows the user to search the CMV database and link findings 1916 and subcategories 1904 to the appropriate E&M codes. The CMV selection tool utilizes a global medical concept vocabulary that can also be used for linking assessments, findings, orders, medications, etc. to the appropriate codes, such as in the assessment/plan section of the present invention.

The findings within the physical examination section can also be linked to plans and assessments via a link selection tool (not shown) that is available in that section of the template builder component 1102 and that allows the user to search the plans and assessments maintained by the template administration builder 1100 and link them to those findings. The findings in the physical examination section are linked to assessments and plans for a patient so as to ensure that those assessments and plans appear in the other sections of the template being built, where applicable.

e. Assessment/Plan Section

After the user completes the physical examination section, clicking the right-most navigation arrow 1402 will take the user to the assessment/plan section of the template builder component 1102. In the assessment/plan section, the user builds a differential diagnosis list 2000 for the template in which the user is working. The type of diagnoses listed in the differential diagnosis list will correspond to the chief complaint and the history of present illness, where applicable. They may also correspond to the possible results from the physical examination checklist or worksheet generated in the physical examination section.

Figure 20:
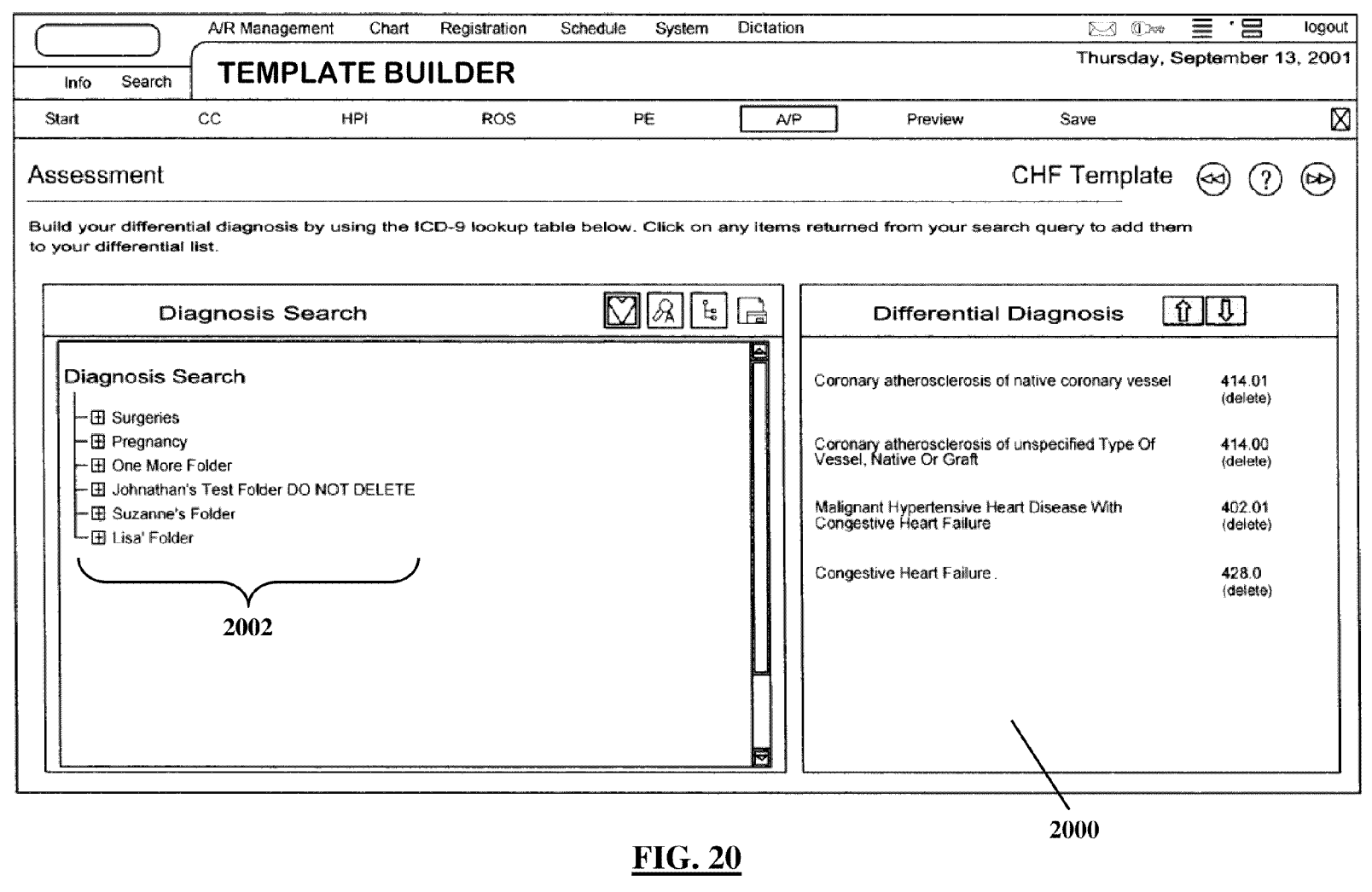
Figure 21:

As illustrated in FIG. 20, the differential diagnosis list 2000 is automatically populated with a list of pre-defined "favorite" diagnoses that correspond to the possible results from a coronary-type physical examination generated in the physical examination section. In addition to the predefined "favorites" for that type of physical examination, the user may also search for diagnoses from ICD lookup tables based on descriptions or codes using a search tool 2100, as illustrated in FIG. 21.

The user can narrow that search by using a folder tree 2002 (FIG. 20) to select the folders of the ICD lookup tables in which the search will be conducted. The user can then add or remove diagnoses in the search results 2102 to or from the differential diagnosis list 2000. The user can also remove "favorite" diagnoses that are already in the differential diagnosis list 2000.

The diagnoses in the differential diagnosis list 2000 will appear in the clinical document as choices to be selected by a clinician during an encounter with a patient. Those diagnoses make up an assessment subsection within the plan/assessment section. As with the E&M codes in the physical examination section, ICD codes are automatically linked to those diagnoses, which allows the A/R module 404 to automatically link the diagnoses to billing codes as that data is capture during a clinician's encounter with a patient.

The assessment/plan section also allows the user to create group-level and diagnosis-specific plans. A group-level plan defines a plan for the template and a diagnosis-specific plan defines a plan for a specific diagnosis (e.g., acute myocarditis) as selected from the differential diagnosis list 2000. As illustrated in FIG. 22, there are preferably at least three parts to each plan, which correspond to three additional subsections within the plan/assessment section of a clinical document: 1) an orders subsection, 2) a medications subsection, and 3) an instructions/education subsection.

Orders include procedures that may be performed to treat the patient's diagnosed illness. A set of standard orders is provided by the template administration component 1100 for inclusion in the orders subsection. A list of orders from which the user can choose is automatically generated from those standard orders based on the diagnoses in the differential diagnosis list 2000 of the assessment subsection. The user can remove standard orders from that list as well as add his or her own orders to the list. The standard orders provided by the template administration component 1100 are already linked to the appropriate CPT codes. And when the user adds his or her own orders, those findings can also be linked to the appropriate CPT codes. As with the E&M and ICD codes, linking CPT codes to the orders allows the A/R module 404 to automatically link those orders to billing codes as the clinician completes the assessment/plan section of a clinical document.

Figure 23:
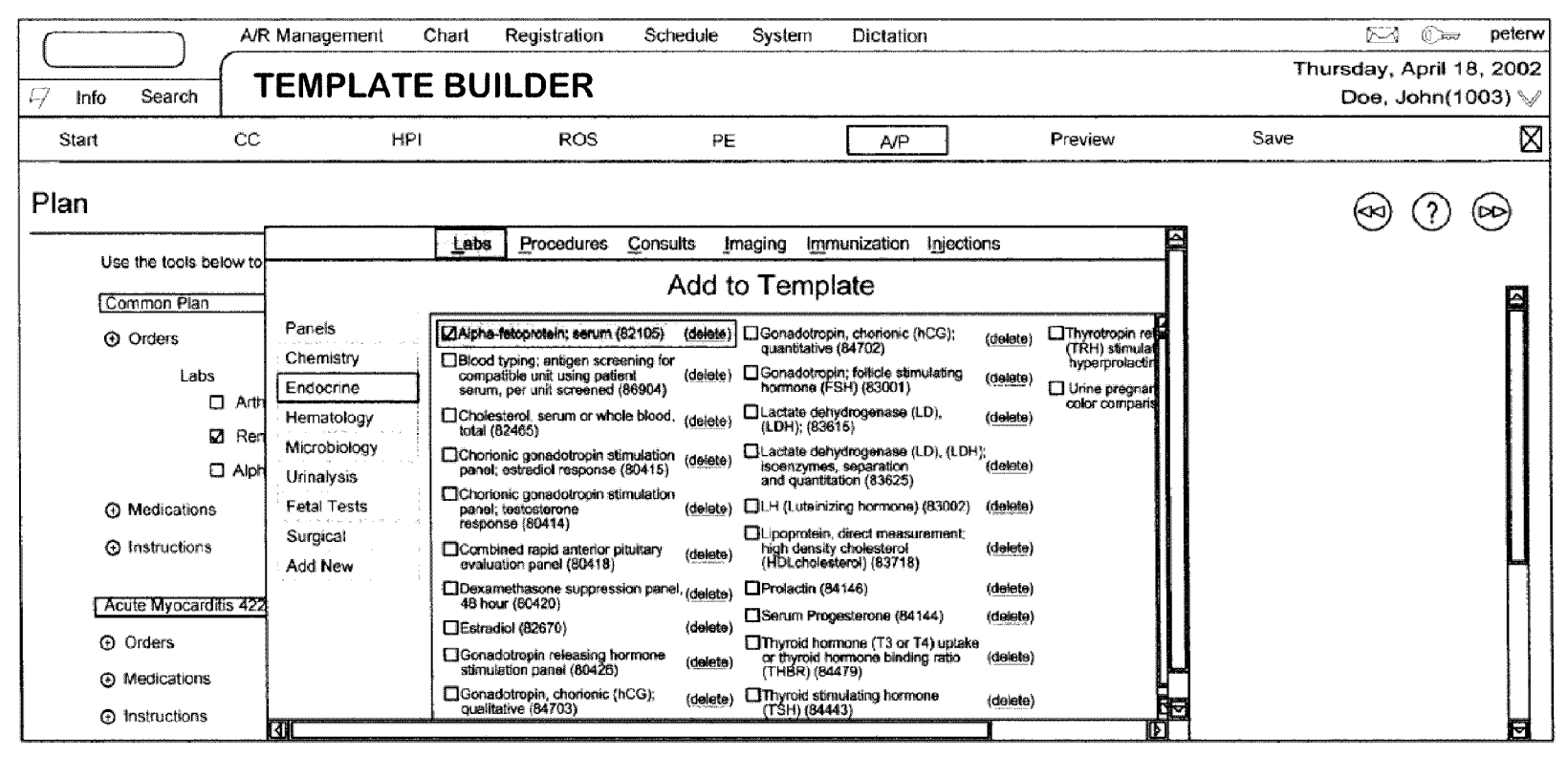

In the example of FIG. 23, the user has selected to configure the orders subsection of the assessment/plan section, and a menu list is displayed having various plan types and categories. Plan types include "Labs", "Procedures", "Consults", "Imaging", "Immunization", and "Injections". As illustrated, the user has selected the plan type of "Labs" and the categories for different types of "Labs" are displayed as "Panels", "Chemistry", "Endocrine", "Hematology", "Microbiology", "Urinalysis", "Fetal Test", and "Surgical". The user can select from those categories or create a new category for each plan type. As illustrated, the user has selected the category "Endocrine" and the list of "Labs" for that category are displayed. The user can then select which labs he wants to appear in the orders subsection. As shown in FIG. 23, the user has selected two "Panels" and an "Endocrine" lab from the menu list. A similar process is utilized for each for each category as well as each other subsection of the assessment/plan section.

f. Template Preview Mode

After the user defines each of the sections of the template, clicking the right-most navigation arrow 1402 will take the user to a template preview mode. In the alternative, the user can enter the template preview mode at any point during the creation of the template by clicking on the "Preview" option in the navigation bar 1400. In the preview mode, the user is able to view the template sections as they will appear in the clinical document that will be created from that template. The user can select which sections to view in the preview mode or the user can choose to view the entire template. While viewing the sections of the template, the user can add omitted items or delete unnecessary items.

Figure 25:
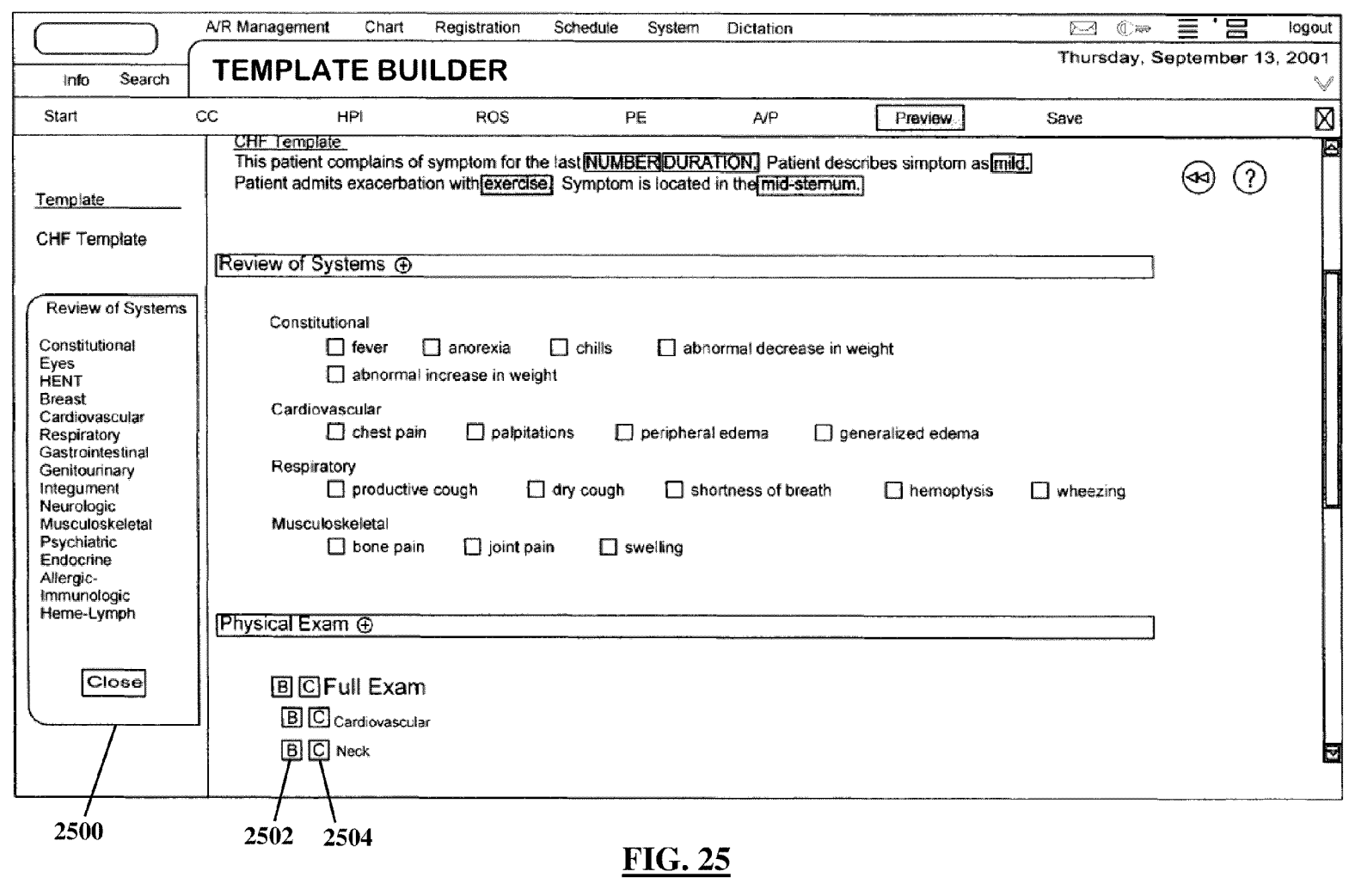
Figure 26:
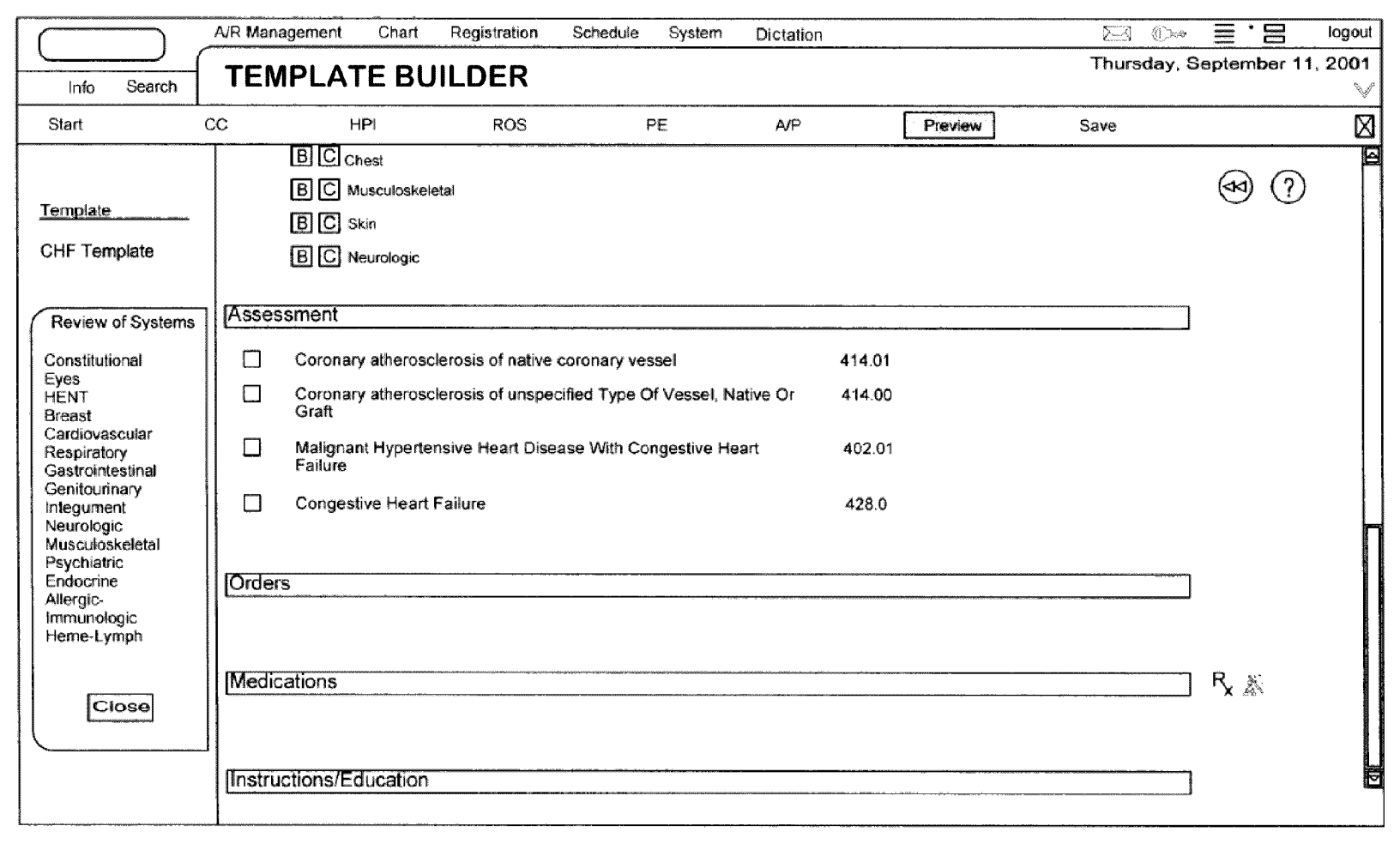

FIGS. 24-28 illustrate exemplary previews of chief complaint (FIG. 24), history of present illness (FIG. 24), review of systems (FIGS. 24 and 25), physical exam (FIGS. 25, 26, and 28), and assessment/plan sections (FIGS. 26 and 27). As illustrated in the exemplary preview of FIG. 24, an action bar 2400 is provided to the left of the preview that includes the name 2402 of the template being previewed in the preview mode. And a "+" button 2404 is provided to the right of the "Review of Systems" label and the "Physical Exam" label.

When the user clicks on the "+" button, a summary list 2500 of body systems 1700 selected for the review of systems section is displayed in the action bar 2400, as illustrated in the exemplary preview of FIG. 25. The user may then add or delete body systems 1700 from the review of systems section using the action bar. But, to edit the symptoms and/or modifiers 1800 within each body system 1700, the user must return to the review of systems section of the template builder component 1102 and/or the review of systems administration page. The user can navigate to those locations by selecting the "ROS" option in the navigation bar 1400 at the top of the preview mode being displayed or by selecting the "Review of Systems Admin" option at the main screen of the template builder (FIG. 13).

Figure 28:
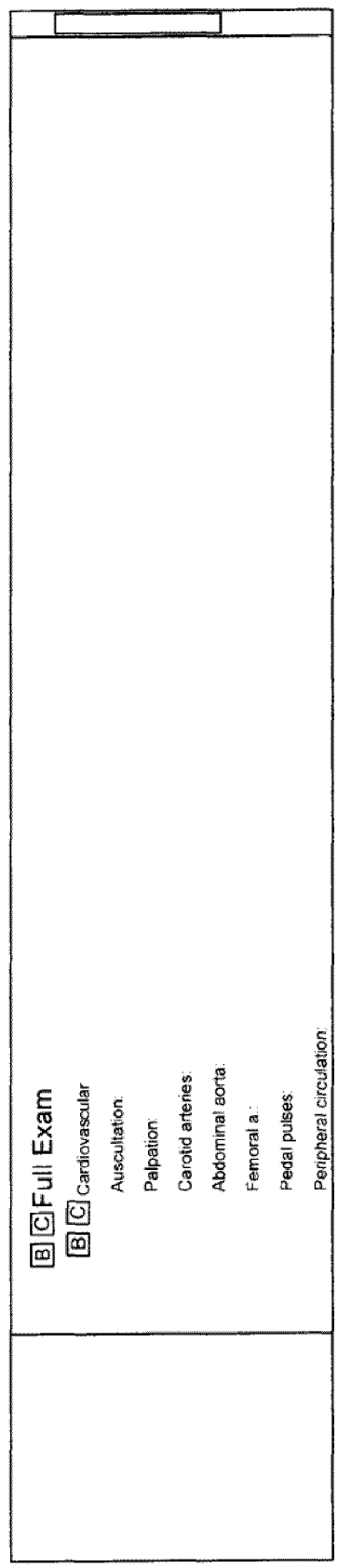
FIG. 28 illustrates an example of a preview screen for a physical exam section supported by the clinical module illustrated in FIG. 11.

In the preview of the physical examination section illustrated in FIGS. 25, 26, and 28, the user can either select the "B" button 2502 to preview a basic exam or the "C" button 2504 to preview a comprehensive exam. In FIGS. 25-26, the user has clicked the "B" button so that only a basic exam preview is displayed. And in FIG. 28, the user has selected the "C" button 2504 for the "Cardiovascular" exam so that a more comprehensive preview of exams is displayed for the "Cardiovascular" exam. To edit the categories 1902, subcategories 1904, macros 1908, findings 1910, etc. within each of those types of exam, the user must return to the physical exam section of the template builder component 1102 and/or the physical exam administration page. The user can navigate to those locations by selecting the "PE" option in the navigation bar 1400 at the top of the preview mode being displayed or by selecting the "Physical Exam Admin" option at the main screen of the template builder (FIG. 13).

As illustrated in the exemplary preview of FIGS. 26 and 27, the assessment/plan section is displayed according to its several different subsections—in particular, the assessment subsection, the orders subsection, the medications subsection, and the instructions/education subsection. When the user selects a diagnosis from the assessment subsection (e.g., congestive heart failure) illustrated in FIG. 26, the orders, medications, and instructions/education subsections are automatically populated with the corresponding data for that diagnosis, as illustrated in FIG. 27. Accordingly, the user can preview much of the functionality by which data is automatically populated into the various sections of the clinical document in the preview mode as well.

iii. Document Builder Component

The templates built with the template builder component 1102 are used by the document builder component 1104 to generate various clinical documents. A clinical document may be created using no template, one template, or more than one template. As illustrated in FIG. 11, for example, the flu template 1114 and the cold template 1116 are combined for a new visit progress note where the patient presents with flu-like symptoms. Although templates for only two types of illness are being combined in the example of FIG. 11, every template can be combined into a single document such that the clinician has every possible chief complaint to choose from during an encounter with a patient and, therefore, every possible assessment and plan. But, because that might be overwhelming, it is preferable to combine templates into smaller groups based on logical relationships, such as those displayed in FIG. 13.

The clinical documents generated by the document builder facilitate the entry of electronic data into the integrated ambulatory suite 400 in a manner that is easy to use, intuitive to users, and faster than making paper entries. The templates used to generate those documents ensure that all necessary information is entered so that documentation is complete and accurate. The integrated ambulatory suite 400 provides for direct entry of electronic data into the clinical documents via a user input device, such as a client workstation 106.

The default settings defined in the templates provide easy-to-use point-and-click data entry with a mouse (e.g., checking a box or selecting from a pull-down menu), manual data entry via a keyboard (e.g., typing text into a make input box), manual data entry by drawing or writing on the user interface (e.g., drawing or writing on a tablet computer with a stylus and using handwriting understanding software to translate the clinician's handwriting), as well as data entry via speech command and dictation (e.g., speaking into a dictation microphone 4000). The default settings defined in the templates also allow electronic data to be pulled forward from other modules and components of the integrated ambulatory suite 400, such as electronic data captured with the clinical module 406 during prior encounters with a patient. Accordingly, much of the clinical documentation generated from the templates will already be pre-populated with much of the requisite data during an encounter with a patient. Moreover, a clinician can note changes since the last encounter with the patient without re-recording information that was previously collected and that has not changed.

The document builder component 1104 generally generates three types of clinical documents from templates: H&P/progress notes, procedure notes, and consultation notes. Summary lists, such as medication, allergy, and problem lists, are automatically updated directly from that documentation. The document builder component 1104 also uses the templates to automate the generation of documents for consultation correspondence, hospital admission, H&P documentation, procedure notes, work and school excuses, and other standard communications.

The document builder component 1104 includes features that assist the user in quickly building document text for each section of a clinical document. Multiple data capture formats are supported in this feature. Data options defined in a template may be used to further simplify creation of that section of a document. For example, a "normal sore throat" template may have been defined to automatically populate the chief complaint, history of present illness, review of systems, physical exam, and assessment/plan sections of the document with appropriate questions and answers for a patient presenting with a sore throat.

After the user has created and/or selected a template with the template builder component 1102, the document builder component 1104 generates a clinical document that will be retained as a final electronic document that can be used by a clinician to capture information about a patient during an encounter with that patient. The clinical document will have a main body that consists of the sections from the templates as well as a section for histories and habits to address patient history information, such as past medical history, specific condition history (e.g., cardiac history), surgical history, medications, allergies, family medical history, genetic screening, social history and problems. In the example of FIG. 11, the main body section of the progress note being generated from the flu template 1114 and the cold template 1116 will have a main body that includes chief complaint, history of present illness, review of systems, and assessment/plan sections that will be completed by the clinician.

The document builder component 1104 compiles the various sections from the associated templates into a clinical document based upon a uniform clinical document standard, such as the CCD, CDA, and CCR standards. For example, a progress note will have a chief complaint section, followed by a history of present illness section, followed by a review of systems section, followed by a physical exam section, followed by an assessment/plan section. The document builder component also compiles the various text that is required by the uniform clinical document standard so that, in addition to the sections defined with the template builder component 1102, the clinical document includes all of the other content required by the uniform clinical document standard. The sections of the clinical document are compiled and the text fields are added at step 1206 of the process 1200 illustrated in FIG. 12.

iv. EHR Component

The EHR component 1106 of the clinical module 406 is used to generate the Electronic Health Record (EHR) for a patient, which includes all of the clinical documents generated for that patient. Accordingly, each patient's EHR contains instances of documents. Each document instance is a single entry in a patient's record that has a date/time stamp and that may also be associated with a specific visit to a healthcare practice. Each document instance also has a document type associated with it, such as a progress note, H&P note, or triage note document type. The document type is used to sort and filter documents when viewing the list of documents in a patient's record.

Patient data can be entered into the document instances via the EHR component 1106 in different formats, including scanned documents, RFD documents, dictation, transcribed electronic documents, and through interfaces with third-party software and devices that capture clinical results. The data is stored in the patient's electronic record on the central database 410. Through integration with the other modules and components of the integrated ambulatory suite 400, the EHR component 1106 eliminates redundant and illegible data in patient records and focuses on quick, dynamic generation of accurate notes that adhere to the applicable regulatory guidelines (e.g., HIPAA).

Authorized users may access the same patient record simultaneously to review patient medical history and vital signs; to capture the patient's history of present illness, review of systems, and physical exam; to document an assessment and plan; and to have orders and prescriptions automatically generated for fulfillment by labs and/or pharmacies. Patient information can be displayed in multiple views and formats, such as text, standard forms, tables, flow sheets, or graphs, to facilitate rapid chart review and determination of the context in which a patient's symptoms occur.

The clinical documents generated with the template builder component 1102 and document builder component 1104 are used by a clinician and other healthcare practice staff to conduct various activities at the healthcare practice and to capture all of the data associated with those activities in a uniform, standardized electronic data format. The EHR component 1106 extensively uses intuitive graphical user interface technologies, electronic drawing tools, and embedded speech understanding software to ensure that an entire patient encounter can be documented with as little physical interaction with the user interface as possible. The EHR component 1106 also allows for keyboard entry as an alternative method to input information.

As a clinician completes clinical documentation, the appropriate ICD, CPT, E&M, HCPCS, RxNorm, and LOINC codes are suggested and captured for automated billing purposes. Thus, the EHR component 1106 automates the entry of charges into the A/R module 404 for proper billing and claims filing, thereby reducing lost charges, ensuring that third-party reimbursement requirements are met, and increasing revenue. The coding and billing process is initiated by the EHR component 1106 and any patient documentation is electronically signed. For example, the EHR component 1106 eliminates the need for separate E&M coding for practice visits through the automatic calculation and suggestion of the E&M coding level based upon its template-driven point-of-care documentation. The integrated coding database used by the integrated ambulatory suite 400 facilitates proper documentation and improves reimbursement by enabling compliance with government and insurance coding guidelines.

The EHR component 1106 provides an automated encounter documentation process and electronic patient record solution within an easy-to-use interface that is both mobile and secure. Clinicians and other healthcare practice staff can electronically access and update all of their patient records within the practice while seeing patients, and they are provided with remote access to patient records to assist them while "on-call" or at the hospital. The functionality of the EHR component 1106 is discussed in more detail below with respect to four types of clinical documents: a) a progress note (FIGS. 29-35), b) H&P Notes (FIG. 36), c) a triage note, and d) a facesheet (FIG. 37).

a. Progress Note

A progress note is an example of a clinical document that can be created and completed using the functionality of the clinical module 406. A progress note is a clinician's primary note for a particular patient encounter. It is amendable and printable. And FIGS. 29-35 illustrate how the EHR component 1106 can be used to complete a progress note that includes functionality provided via the template builder component 1102, as discussed above.

Figure 29:
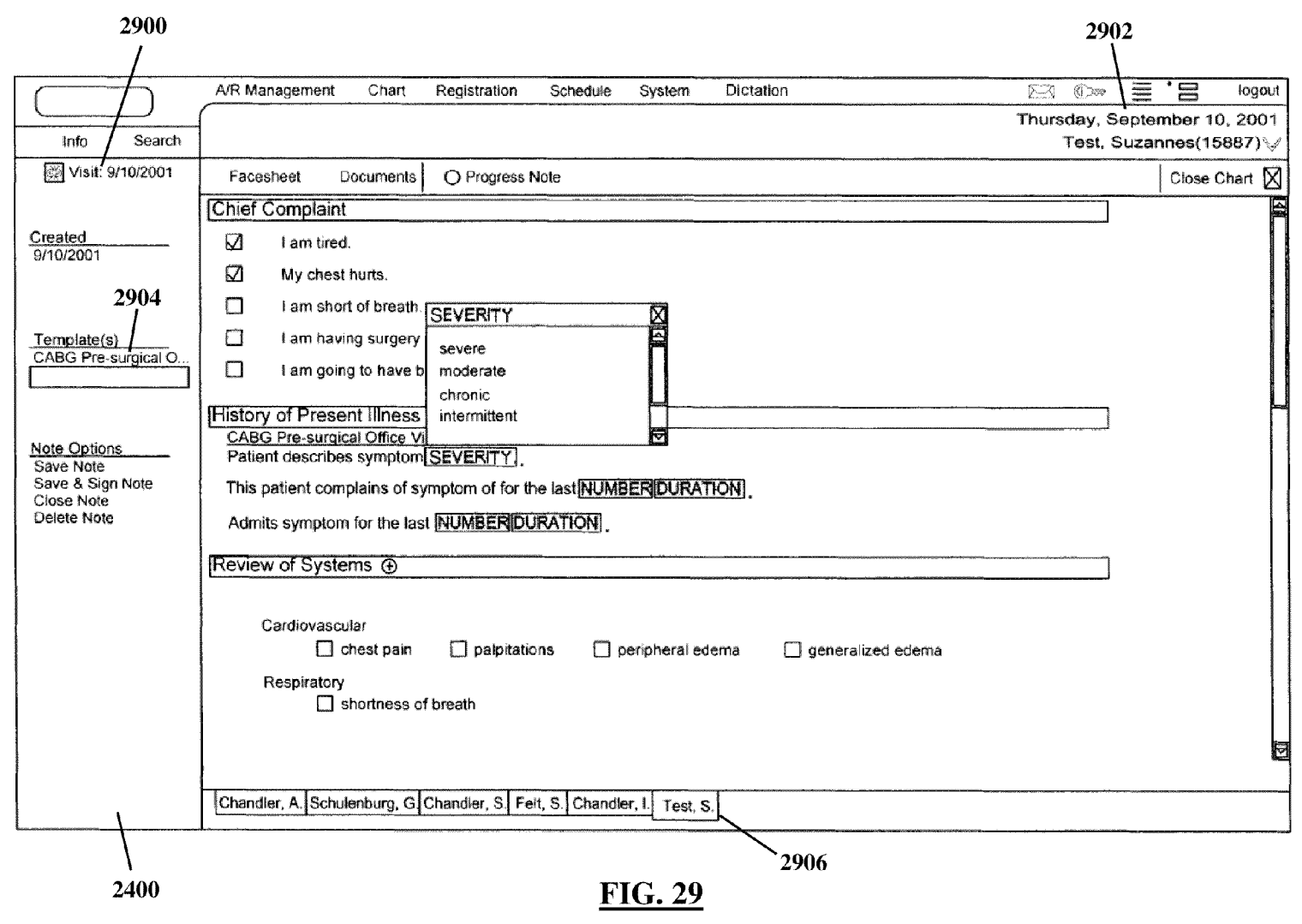

To access a progress note for a patient, the clinician can select the progress note from the desktop 500 (FIG. 5), a document list (FIG. 35), and a facesheet 3700 (FIG. 37). After the clinician selects a progress note to complete, a blank progress note is displayed at the user interface. As illustrated in FIG. 29, the clinician can then determine if the visit date 2900 displayed in the action bar 2400 matches the current date 2902. The date displayed in the action bar 2400 represents the date of the patient encounter that will be linked to the progress note in the patient's EHR. If the progress note is not already associated with a scheduled patient encounter, the clinician may also choose to create a progress by selecting the default visit displayed (e.g., the last visit instance) or selecting a new visit by clicking a link button (e.g., the icon to the left of the visit date 2900) that allows the user to search for and assign a visit date.

A template list 2904 of the available templates for use in a progress note is also provided in the action bar 2400 of the blank progress note. After the correct visit date 2900 is selected, the clinician selects one or more templates from the template list 2904 that the clinician wants to use to generate a progress note for use in during the encounter with the patient.

Several template fields can be provided to assist the clinician in finding the desired template(s), such as a physician's template field, a nurse's template field, or an illness type template field. Upon clicking on the template field, a drop-down menu displays custom templates that correspond to the template field, including pre-defined templates and those created by the user. After the clinician selects which templates he or she wants to use in generating the progress note, the document builder component 1104 compiles the sections from those templates and displays those sections in the progress note so that the progress note is no longer blank. The clinician can perform that process for many different patients at once, choosing different templates for each patient. The clinician can navigate between the progress notes created for each of those patients by clicking on the corresponding tabs 2906 at the bottom of the progress note.

In FIG. 29, the clinician has selected to work with the "CABG Pre-Surgical Office Visit" template. The document builder component 1104 has pre-populated all of the selected items for the progress note, which were defined using the template builder component 1102. As discussed above, a progress note typically has the following sections: chief complaint, history of present illness, review of systems, physical examination, and assessment/plan sections.

To begin completing the progress note, the clinician selects the desired elements within the progress note. First, the clinician selects the chief complaint that most closely relates to the patient's subjective description about the problem that has brought the patient to see the clinician. A list of possible chief complaints, such as "I am tired" or "My chest hurts", that were defined with the template builder component 1102 are displayed for the clinician to select from and add to the completed progress note. The clinician can select the relevant chief complaint(s) by clicking in the check box beside the corresponding chief complaint or by speech command (e.g., by saying: "Chief Complaints."—"I am tired."—"My chest hurts." into a dictation microphone 4000). The chief complaints may also have been entered in a similar manner by a healthcare practice staff member using the registration component 420 during patient check-in. If the latter, that data will automatically flow into the chief complaint section of the progress note so the clinician does not have to enter it.

After the chief complaint(s) are entered into in the chief complaint section of the progress note, the clinician enters information into the history of present illness section. Selecting the "History of Present Illness" header, or saying "History of Present Illness" when voice recognition software is used, will cause the fields within history of present illness section automatically populate with the descriptions that were defined for that section using the template builder component 1102. Some of those descriptions may be not displayed if they do not correspond to the selected chief complaint(s). In FIG. 29, for example, "I am tired" and "My chest hurts" were entered as the chief complaints and only the corresponding descriptions for the history of such a chief complaint are displayed in the history of present illness section. In other instances, the same descriptions will be displayed in the history of present illness section regardless of the chief complaint.

The descriptions in the history of present illness section can be completed in accordance with the manner that fields within those sentences were set up with the template builder component 1102. For example, information can be entered by the user in the form of a care provider list, date stamp, duration, measurement, make input box, number selector, make multiple select, make select list, or demographic information control type. In FIG. 29, the clinician is selecting the severity of a symptom from a make select list control type. The clinician can access the pull-down menu of the make select list with the click of a mouse on the "SEVERITY" field or by speech command (e.g., by saying "Severity." into a dictation microphone 4000). The clinician then selects from the choices in the make select list in a similar manner.

The fields into which the clinician can input or select data are surrounded by a box so they can be easily identified. Certain other patient-specific text may be automatically populated into the sentences without user input, such as gender-specific pronouns (e.g., he/she, himself/herself, his/her, and him/her) and patient demographic data (e.g., patient name, age, and sex). That text is populated into their respective fields without the need for any input from the clinician. The completed descriptions in the history of present illness section will appear in the completed progress note.

After completing the last field in the descriptions in the history of present illness section, the clinician will automatically be moved to the review of systems section of the progress note. In the alternative, the clinician can navigate to that section by selecting the "Review of Systems" heading as discussed above with respect to the history of present illness section. The clinician can navigate between sections in that manner at any point during the encounter with the patient. Navigating to a section results in the fields in that section becoming active for selection or speech command entry.

Figure 30:
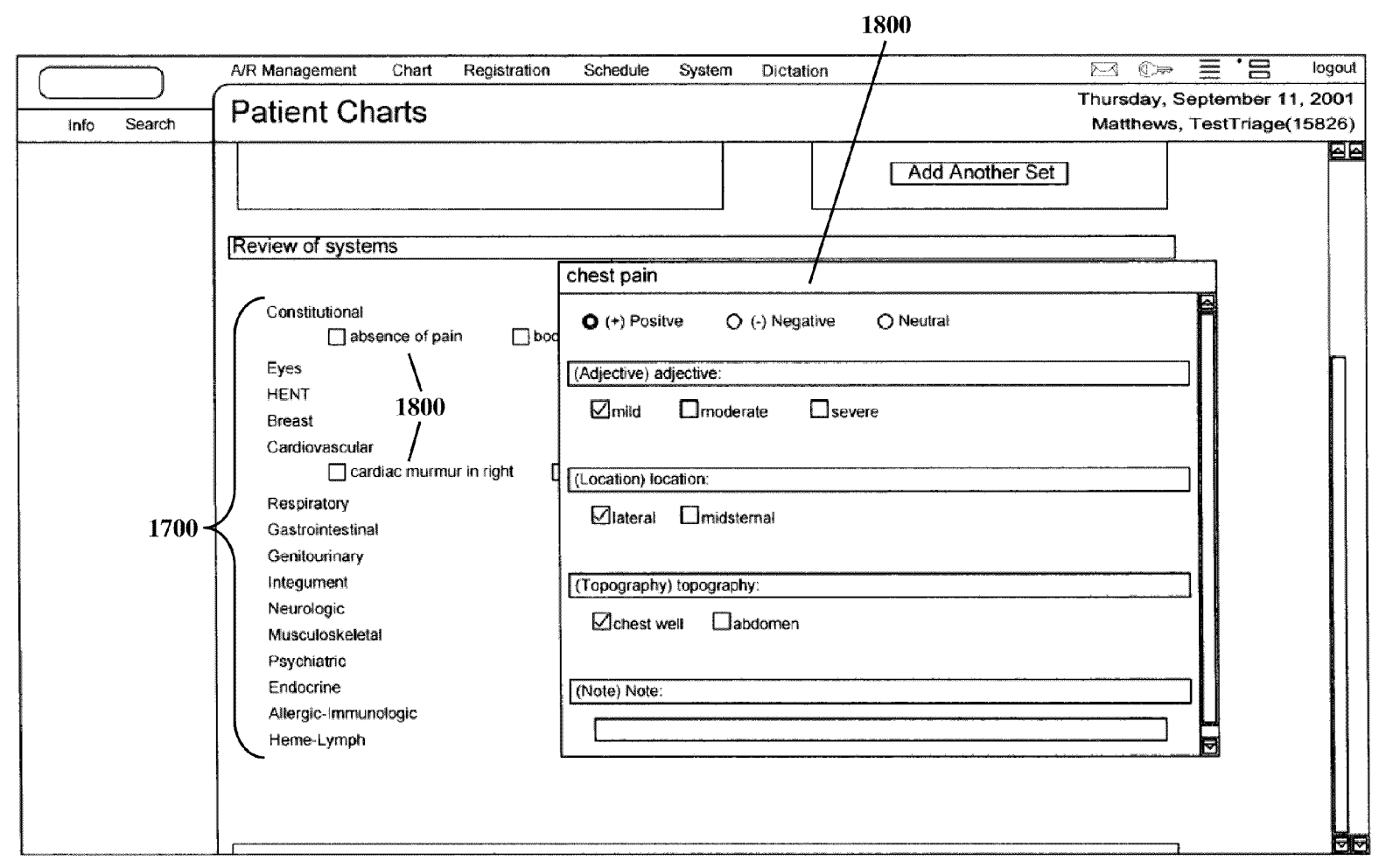

As illustrated in FIG. 30, the review of systems section is populated with an inventory of body systems 1700 that is defined based on a series of questions the clinician asks the patient to identify symptoms and/or modifiers 1800 corresponding to the specific illness that the patient may be experiencing or has experienced. Some of those questions may have been asked during the patient check-in process, and the answers will automatically flow to the review of systems section of the progress note from the registration component 420. Some answers may also flow from a triage note. The clinician will be prompted by pup-up boxes to ask any questions not already answered during his or her physical examination of the patient. In FIG. 30, the clinician is being prompted to ask the patient about any feelings of chest pain.

The clinician completes the review of systems section as he or she examines the systems identified in that section. The clinician may choose not to include some of the systems listed in the review of systems section, depending on the patient's reason for visit, physical appearance, etc. When some systems are not included in the review of systems section, those systems will not be shown in the completed progress note. Also, if all symptoms are neutral for a system, that system is not included in the completed progress note. If the system has either a negative or positive symptom, the system is included in the completed progress note.

As each system heading in the review of systems section is selected by the clinician, multiple symptoms and/or modifiers 1800 related to that body system 1700 are displayed. The default settings for each symptom will be "neutral" unless they were changed with the template builder component 1102 during the template building process. The user may click on the checkbox next to the symptom once to change the status of the symptom, or the user may use a speech command to select the checkbox (e.g., by saying "Chest Pain"—"Positive." into a dictation microphone 4000). Only one status can be selected. In FIG. 30, the user has selected the systems "Constitutional" and "Cardiovascular" and the respective symptoms are displayed, such as "absence of pain," "cardiac murmur," and "chest pain." The user has selected the "chest pain" symptom as a "positive" status, thereby indicating that the patient is experiencing chest pain. The "negative" status indicates that the patient denies the symptom.

To enter more details about the positive status of a symptom, the clinician can click on or say the actual name of the symptom. Selecting the symptom in that way will cause the radio button to change to "positive" and a pop-up box will appear, as shown in the foreground of FIG. 30. The pop-up box allows the user to select more detailed information, such as "severity," "location," and "topography." The clinician may also input notes with respect to the selected symptom by typing them in with a keyboard or dictating them into the integrated ambulatory suite 400. Each positive symptom and its descriptors will appear in the completed progress note.

After the clinician completes the review of systems section, he or she will be automatically moved to the physical exam section of the progress note, or the clinician can navigate to that section at any point, as discussed above. The physical exam section is typically defined by the templates defined with the template builder component 1102. In the alternative, the clinician can create a section for describing the examination from scratch during the examination by choosing the body systems and related components independent of any template.

Figure 31:
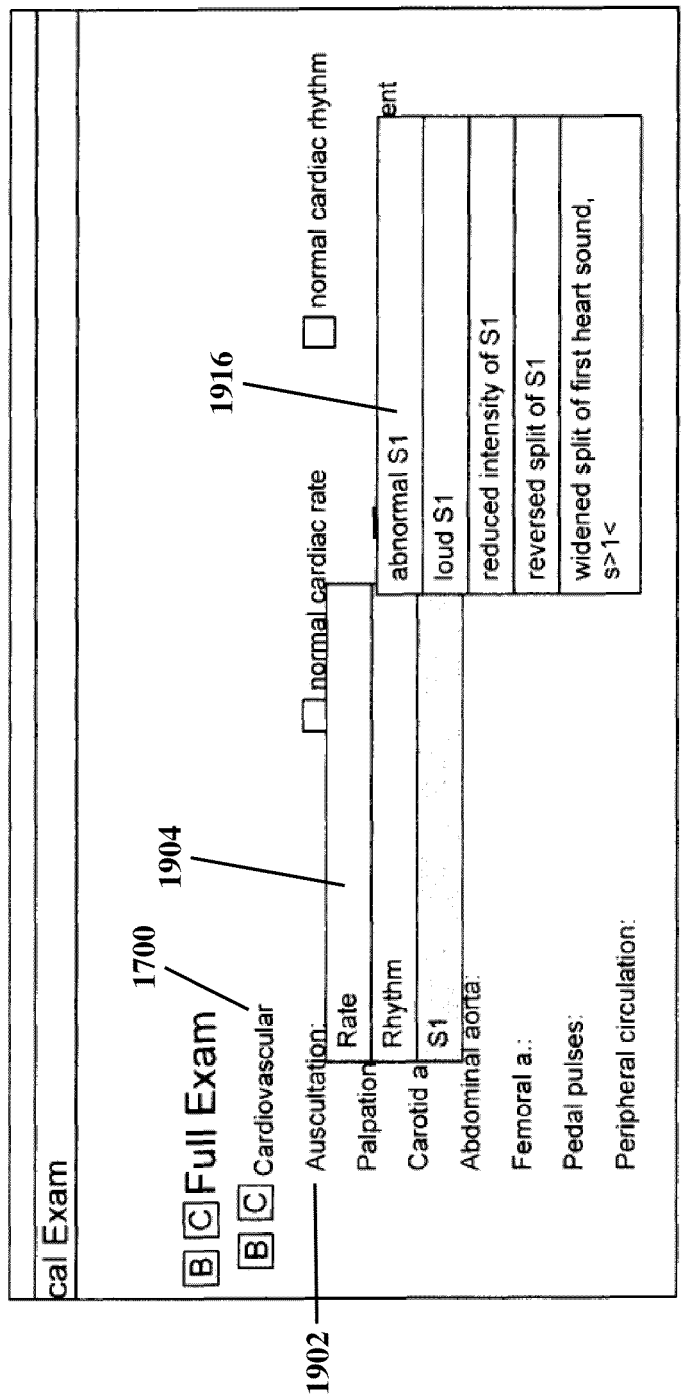
Figure 32:

As discussed above, when the basic exam, or "B" button, is selected, the body systems 1700 selected for the template that were pre-selected for the basic exam are displayed in the physical exam section. And when the comprehensive physical exam, or "C" button, is selected, the body systems 1700 selected for the template that were pre-selected for the comprehensive exam are displayed in the physical exam section. If nothing is selected in the physical exam section, then the clinician may select "B", "C", or both for each of the body systems 1700, as illustrated in FIG. 31 for the Cardiovascular body system 1700. If nothing is selected, then the both exams are displayed as the default.

The user can also select findings 1916 for any of the terms in the Physical Exam document section. In the example of FIG. 31, the category 1902 "Auscultation" has been selected for the body system 1700 "Cardiovascular" such that the subcategories 1904 "Rate", "Rhythm", and "S1" are being displayed. By selecting the text of those subcategories 1904 (e.g., hovering the pointer of a mouse over them or giving a corresponding speech command), a pop up box (foreground) is displayed with more detailed information about the findings 1916 for that subcategory 1904. In the example of FIG. 31, the "S1" subcategory 1904 has been selected and a cascading menu of findings 1916 in that subcategory 1904 are being displayed. The clinician may select from that menu, and whichever finding 1916 he or she selects will be added to the "Auscultation" portion of the physical exam section and displayed in the completed progress note. The clinician may select those findings 1916 by a series of mouse clicks or via a series of speech commands (e.g., by saying "Cardiovascular."—"Auscultation."—"S1."—"Abnormal S1." into a dictation microphone 4000).

In the alternative, the physical exam section can be implemented in a manner similar to that discussed with respect to the physical exam section of the template builder component 1102 and FIG. 19. More particularly, a system tree 1900 can be provided that lists all the body systems 1700 and the body systems 1700 and findings 1916 can be displayed with selection boxes. Values and modifiers can also be associated with each finding 1916 as discussed with respect to the physical exam section of the template builder component 1102 and FIG. 19.

After the clinician completes the physical exam section, he or she will be automatically moved to the assessment/plan section of the progress note, or the clinician can navigate to that section at any point, as discussed above. Following an encounter with a patient, a clinician typically has a diagnosis, orders, prescriptions, and instructions for the patient. The clinician is able to document his or her assessment of the patient and his or her plan for the patient in the assessment/plan section the progress note so that it will become part of the patient's EHR. Accordingly, the assessment/plan section may include an assessment subsection, an orders subsection, a medications subsection, and an instructions/education subsection. The assessment subsection contains diagnoses with related ICD coding chosen by the user with the template builder component 1102. And when the completed progress note is created, the assessment subsection of that document will display the selected diagnoses and their corresponding ICD codes.

The user selects a diagnosis or multiple diagnoses by clicking on the checkbox next to each desired diagnosis from the differential diagnosis list 2000 defined with the template builder component 1102. Checkboxes can also be provided to allow a clinician to mark an item as a "rule out" instead of a diagnosis. Such "rule out" boxes are used, for example, when tests are ordered to rule out a certain diagnosis, so the code for that item will not be used to bill the encounter, as it is not really a diagnosis. The selected diagnosis and the associated ICD code will become bolded to bring it to the clinician's attention.

Upon the user's selection of one or more diagnosis from the assessment subsection, the orders, medications, and instructions/education subsections of the assessment/plan section are automatically populated with corresponding data. For example, a patient who is diagnosed as having chest pain will typically require at least a chest X-ray, an EKG, a prescription for nitroglycerin, and a follow-up visit. Accordingly, the X-ray and EKG may be automatically populated as selectable options in the orders subsection, the prescription for nitroglycerin may be automatically populated as a selectable option in the medications subsection, and the follow-up visit may be automatically populated as a selectable option in the instructions/education subsection. The clinician completes each of those sections in a similar manner as that discussed for the assessment subsection—namely, by selecting from selectable options. The clinician may also add notes to any of the subsections of the assessment/plan section using any of the methods previously discussed.

In the order subsection of the assessment/plan section, the selected orders are automatically linked to CPT coding. Those orders may be specific to CPT codes and/or user-created orders that have been linked to the CPT codes using the template builder component 1102. As with the ICD code for a diagnosis, the CPT coding for a selected order is displayed next to that order in the completed progress note.

In the medications subsection, the clinician fills in the dosage and amounts for the selected medications, which are used to automatically write a prescription for the patient. Prescriptions may also be written from scratch within the medications subsection. Both types of prescription writing are facilitated via interaction with the drug information in the reference databases 412 (e.g., the First DataBank, Inc.'s NDDF PLUS brand coded classification system and the RxNorm coded classification system). That drug information includes descriptions of different drugs as well as unique identifiers and pricing information for each of those drugs. By selecting different drugs from the reference databases 412, the drug selected for the prescription will automatically be linked to its unique identifier and price for use in generating, electronically submitting, and fulfilling the prescription, and for use in generating a bill, claim, or statement for the prescription. The automated prescription process is discussed in more detail below.

After the clinician completes each subsection within the assessment/plan section of the progress note, the progress note is complete, which concludes step 1208 of the process 1200 illustrated in FIG. 12. The clinician's selections are displayed in a completed progress note document, as shown in FIGS. 33 and 34. Each section is displayed, even if no entries were made to that section. However, areas that were not examined or inquired into by the clinician are not displayed so that, for example, "Constitutional" is not displayed in the physical examination section.

The completed progress note is created in XML format and signed at step 1210 of the process 1200 illustrated in FIG. 12. The progress note can be electronically signed with a saved signature based on a clinician's approval, or it can be signed via a user interface, such as via a stylus and tablet computer, by the clinician writing his signature on the user interface. Then, at step 1212, that document is converted into a modified XML format (e.g., HTML) that is compliant with the HL-7 CDA standard using XSLT processing. That completes the process 1200 illustrated in FIG. 12.

As illustrated in FIG. 11, the progress note is saved to the central database 410 according to the progress notes document type 1112 after it is signed, created, and converted. The saved progress note is available for printing and future access. After the progress note is saved and/or signed, it will be displayed in the document list of a patient's EHR, as illustrated in FIG. 35. It may be closed, opened, or amended. If not saved, it can be deleted. In FIG. 35, the progress note is saved and displayed in a document list titled "Chart Documentation."

Other documents can also be generated and completed with the clinical module 406. And other medical history information can be included in a progress note as separate sections, including past medical history (PMH), past surgical history, social history, and family medical history. Those sections generally enable the clinician to gather information about the medical, social, and family history of a patient. As an example, illnesses can be organized under the categories of the body systems they affect for PMH. A list of illnesses may be pre-selected by the clinician. And when specific illnesses are selected, the clinician may enter dates of onset and any notes concerning that situation. That functionality can also be accessed from the other areas in the system, such as the face sheet 3700.

b. H&P Note

An H&P note is another type of document that is generated with the template builder component 1102 and document builder component 1104 and completed with the EHR module 1106. An example of the physical examination section of an H&P note generated with the template builder component 1102 and document builder component 1104 is illustrated, for example, in FIG. 36. In the H&P note of FIG. 36, the body systems 1700 pertinent to that H&P note are listed along the left side of the page (i.e., Eyes and HENT). The clinician selects a body system 1700, which causes the various categories 1902 and/or subcategories 1904 within that body system 1700 to be displayed. The clinician can then select findings 1916 within the various categories 1902 and/or subcategories 1904 to display and edit.

Figure 36:
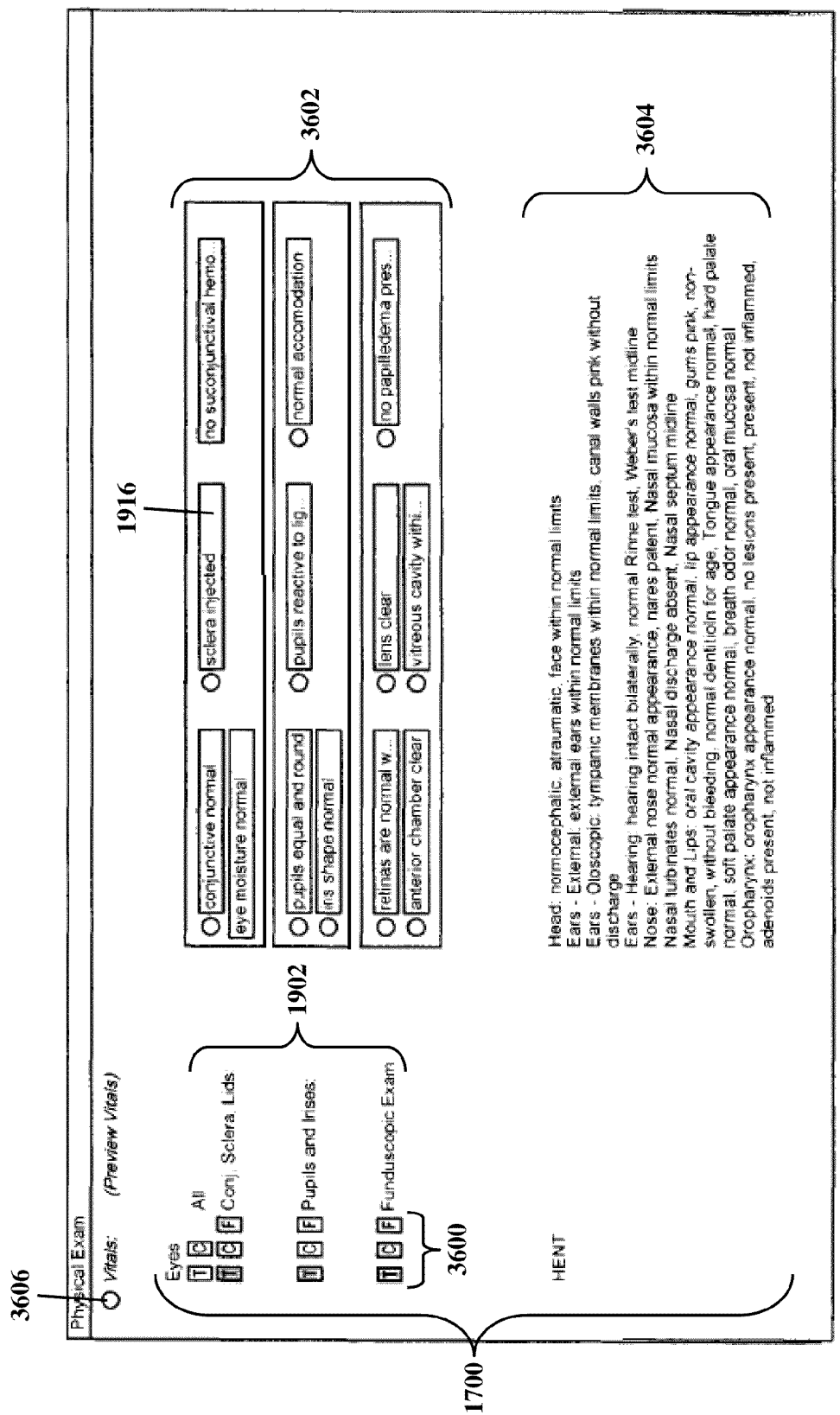
FIG. 36 illustrates an example of a history and physical (H&P) note being completed by a clinician using the EHR component of the clinical module illustrated in FIG. 11.

In the example of FIG. 36, the clinician selected the system "Eyes" and the subcategories 1904 "All", "Cond., Sclera, Lids", "Pupils and Irises", and "Funduscopic Exam" are displayed in the order of the categories 1902 from which they were chosen. The findings 1916 for those subcategories 1904 are displayed adjacent thereto in the edit window 3602. The findings 1916 for the body system 1700 that has not been selected also appear adjacent that body system, but not within an edit window 3602. Instead, as illustrated in FIG. 36, those findings 1916 appear as a pre-defined listing 3604 with the default values and modifiers that were defined with the template builder component 1102.

The clinician is provided with three different options 3600 for determining which findings 1916 are displayed for editing in an edit window 3602: options "T", "C", and "F". Selecting option "T" only displays the findings 1916 that were defined for a category 1902 and/or subcategory 1904 using the template builder component 1102 and excludes the standard findings 1916 provided by the template administration component 1100. Selecting option "C" displays all of the findings 1916 for the corresponding category 1902 and/or subcategory 1904 of the selected body system 1700. And selecting option "F" allows the clinician to focus on specific macros 1908 by displaying only the findings 1916 associated with one or more macros 1908 selected from a category 1902 and/or subcategory 1904 of the selected body system 1700.

When the clinician selects a specific finding 1916 to edit in the edit window 3602, a list of modifiers is presented for further selection by the clinician. Such modifiers can indicate, for example, the severity of the finding (e.g., "severe", "moderate" or "mild"). The user can select the appropriate modifier, which then becomes associated with the finding in the completed H&P note. Any findings 1916 changed from their default value in that way will be marked accordingly to provide a visual indication of the edit, such as marking the edited findings 1916 in red.

A drawing or other digital image can also be incorporated into the H&P note. For example, a clinician can select a digital image of a patient's abdomen and draw the location of previous surgical scars, changes in discoloration, or an area of infection between visits. As the H&P note is being created, the user has the option of selecting to include the drawing. The user then selects the desired image from the library of images. Preferably, that is achieved by displaying an image of a full human body and allowing the user to focus in on a specific area. After the desired image is displayed, the user can then draw the desired shape and color to add to that image, such as by using a "pencil" tool in an electronic sketch pad. Accordingly, a clinician can select anatomical images from a library, draw on them, and embed them into documents and notes to better document medical information that would otherwise be difficult to communicate with words alone. An image may be incorporated into other clinical documents in a similar manner.

Also in the H&P note of FIG. 36, a "Vitals" button 3606 is provided at the upper left corner of the screen. A clinician can click the "Vitals" button 3606 at any point during the physical examination of a patient to view or add vital clinical information for the patient (e.g., vital signs, problems, medications, allergies etc.).

c. Triage Note

A triage note is yet another type of document that is generated with the template builder component 1102 and document builder component 1104 and completed with the EHR component 1106. Such a triage note will prompt a clinician to enter detailed triage data for a patient. It is designed to be the initial documentation point in a patient's visit and will usually be completed by a nurse before the patient starts the encounter with the clinician. All information entered into the triage note will be used in other sections of the clinical documentation generated as part of the patient's visit to the healthcare practice and will become part of his or her EHR. For example, the reason for visit is updated based on the information gathered by the registration component 420 of the framework module 402 during the patient check-in process. The information available for entry includes reason for visit, presenting symptoms, additional notes, vital signs (e.g., blood pressure, heart rate, respiratory rate, temperature, etc.), review of systems, orthostatic vital signs, etc.

d. Facesheet

The EHR component 1106 of the clinical module 406 also supports the generation of patient charts, which represent a view of the patient's entire EHR. If the user selects the "Chart" option from the desktop 500 menu bar 502 (FIG. 5), a summary of the EHR for a selected patient is displayed as a facesheet 3700. As illustrated in FIG. 37, the facesheet 3700 of the selected patient contains a critical, but brief, summary of the patient information that is most frequently used by the clinician and other healthcare practice staff members. The facesheet 3700 serves as a "home base" for clinicians and other healthcare practice staff members, allowing them to quickly and easily access more detailed information in a patient's chart. For example, it allows the clinician to view vital clinical information (e.g., vital signs, problems, medications, allergies, etc.) at a glance without having to navigate further into the patient's chart.

In the example of FIG. 37, the facesheet 3700 includes a reason for visit summary 3702, a vital signs summary 3704, a recent document list summary 3706, a problem list summary 3708, an allergy list summary 3710, a medication list summary 3712, and other pertinent information regarding the patient's medical history. That data may have been entered during registration, scheduling, triage, or physical examination of a patient—prior to or during the current patient visit. The information displayed within the facesheet 3700 can be customized to show different information lists. And, as with the other clinical documentation generated by the clinical module 406, a clinician or other healthcare practice staff member can simultaneously open and navigate between the facesheets 3700 for multiple patients using corresponding tabs 3714 at the bottom of each facesheet 3700, thereby providing immediate access to clinical information for multiple patients at once. The clinician or staff member can also move to any other area of the integrated ambulatory suite 400 via the options in the menu bar 502 and can create a clinical document, such as a progress note, H&P note, or triage note, by selecting the desired type of clinical document from a list of "Common Tasks" 3716 in the action bar 2400.

The facesheet 3700 also allows the clinician or staff member to edit and add to the summary information displayed in the facesheet 3700 by clicking the "+" button 3718 to the right of each summary. For example, in FIG. 37 the clinician has chosen to add a new medication to the patient's medical record, which the clinician can do by selecting the "Add New Medication" option in the medication list toolbar 3720. As a result, a prescription for that medication will be added to the patient's medication list with an indicator as to whether that prescription was generated within the practice or by an outside provider. If no problem is identified with the other medications in the patient's medication list, the a prescription for the newly added medication may be automatically generated and sent to a pharmacy for fulfillment. The clinician can automatically generate prescription refills from the facesheet 3700 in a similar manner.

The facesheet 3700 also allows the clinician or staff member to open the various clinical documents on that facesheet 3700 by selecting those documents from the clinical documents listed in the recent document list summary 3706. Those documents include the note created with the template builder component 1102 and document builder component 1104 as well as other documents in the patient's EHR, such as scanned in documents. Those documents can be amended, printed, and cosigned via the facesheet 3700.

D. Scheduling Module

The scheduling module 408 supports scheduling for patients, clinicians, staff members, office equipment, and any resource the user chooses to define. The scheduling module 408 is a rules-based, flexible module that supports many different levels of scheduling complexity. Appointment scheduling is administered using automated scheduling rules that ensure proper resource and time allocation and further facilitates a smooth flow of patient appointments. Appointment scheduling functionality is configurable to the healthcare practice and to the specific user. Clinicians and other staff members at a healthcare practice can review schedules via a user interface, such as a client workstation 106, at any time and from any point in the healthcare practice, which provides those users with real-time access to appointment availability and scheduling information.

Using the functionality of the scheduling module 408, a healthcare practice's staff, such as office assistants, can schedule appointments for patients using simple "drag and drop" techniques in accordance with personnel, room, and equipment availability. As an appointment is scheduled, all resources, such as rooms, equipment, personnel, and medical procedures, are taken into consideration to ensure that conflicts do not occur between resources. Rules templates can be defined to control the available appointment times for resources so that patients, clinicians, rooms, and equipment can only be scheduled at times when each is available. In addition to preventing a resource from being scheduled for two appointments at the same time, those rules can also provide other limitations on resource scheduling to prevent other potential scheduling conflicts. For example, a clinician can create a rule that he or she is not available for any type of appointment during lunch (see, e.g., FIG. 38 (listing the rule "12:00:00 PM-01:00:00 PM"—"Exclude"—"All")) or that he or she is only available for a specific type of appointment at a specific time (see, e.g., FIG. 38 (listing the rule "8:00:00 AM-12:00:00 PM"—"Include"—"GYN Visits"—"OB Visits"—"Surgery Appointments")). And an office administrator can create a rule that designates a specific room for a specific medical procedure during certain days and times (e.g., scheduling examination room 1 for GYN visits only on every third Thursday of every month). Rules templates may be defined and applied across many resources and dates to minimize schedule maintenance.

Figure 38:
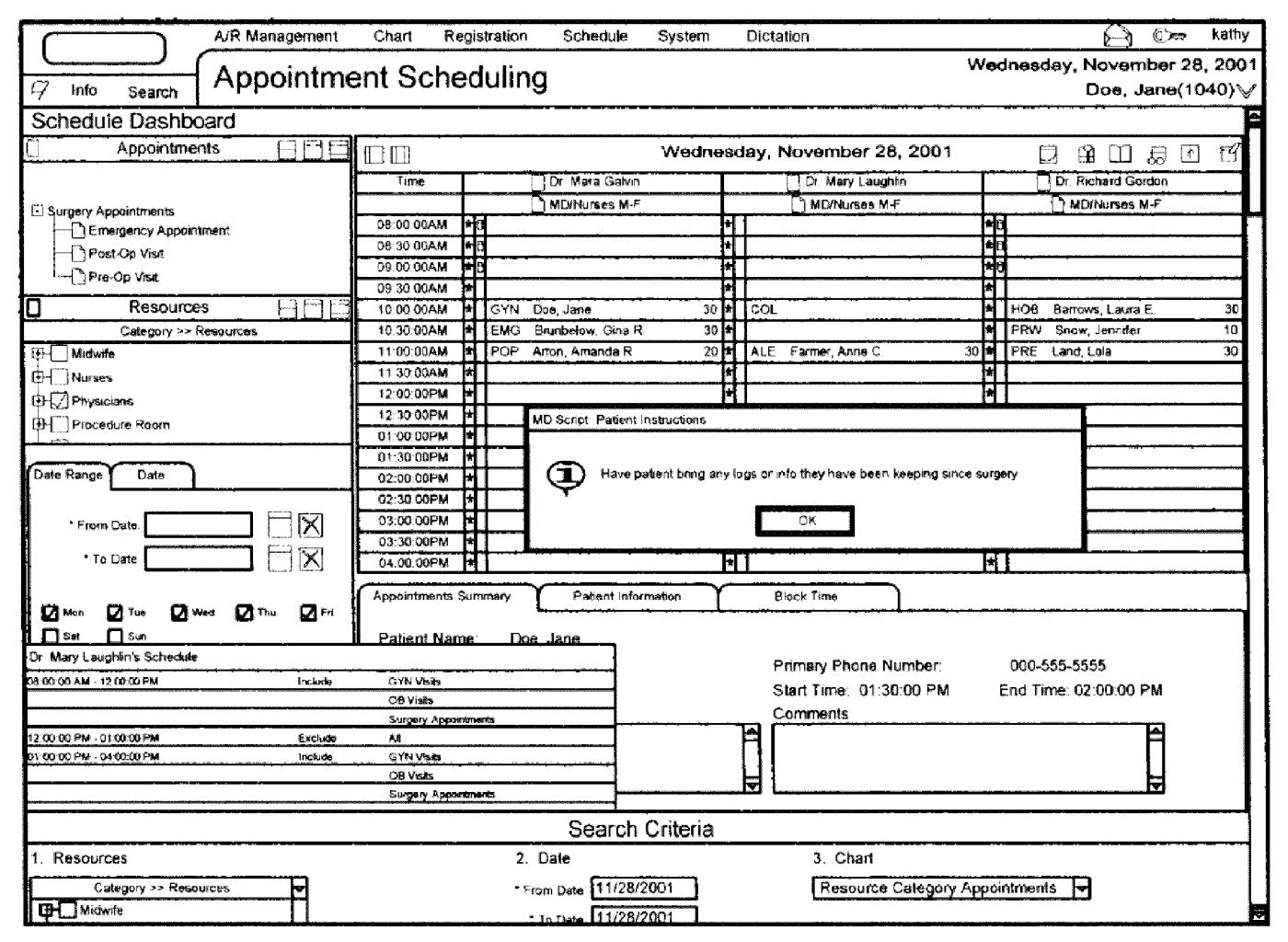

The resources that can be scheduled with the scheduling module 408 are presented to the user with several viewing options, such as viewing multiple clinician's schedules on the same day (see, e.g., FIG. 38 (listing three clinician's schedules for Wednesday, Nov. 28, 2001.)) or viewing multiple days for one provider (e.g., viewing one clinician's schedule for an entire week). The user can perform advanced searches for multiple resources and various time and date ranges. The search parameters that define a search template can be saved and accessed for future use in performing a subsequent search.

As illustrated in FIG. 38, and as discussed above with respect to the registration component 420, administrative flags can be associated with a patient to serve as reminders to make special arrangements for a specific patient when scheduling an appointment. For example, where an "In Collections" administrative flag is provided, the office assistant may be instructed by that flag to request payment for outstanding balances before scheduling the patient for another visit. Or where a "Needs Wheelchair" is provided, the office assistance may be instructed by that flag to schedule a wheelchair to be available during the corresponding patient's visit.

When a selected appointment time and date is not available, the next available time and date are quickly accessed and displayed to facilitate an efficient scheduling process. In the example of FIG. 38, the user has scheduled an appointment and the system automatically generated an administrative flag (pop-up in middle of screen) to remind the patient of specific instructions to follow prior to the appointment (e.g., "Have patient bring any logs or info they have been keeping since surgery."). The instructions are based upon the type of appointment that has been scheduled for the patient. Additionally, as the user attempted to schedule the appointment during a time which the physician, "Dr. Mary Laughlin" in the example of FIG. 38, has indicated she will not be available for that type of appointment (i.e., "12:00:00 PM-01:00:00 PM—Exclude—All"), for which the user then chose to view the rules (list in bottom left of screen) that prevented scheduling that appointment.

Scheduling data may also flow into the scheduling module 408 from other the modules and components of the integrated ambulatory suite 400 to automatically schedule appointments or create flags as reminders for scheduling appointments. For example, a clinician may identify that a follow-up appointment is needed in the instruction/education subsection of a progress note. A request for such an appointment will then be directly transferred from the progress note to the scheduling module 408, where the appointment will automatically be scheduled or a user will be reminded to schedule a follow-up appointment (e.g., generating an administrative flag that alerts an office assistant to schedule a follow-up appointment with the patient as the time for the appointment draws nearer). Similarly, such data may flow to the A/R module 404 to create an administrative flag alerting an office assistant to schedule a follow-up appointment while filling in payment information during patient check-out.

E. Central Database

The central database 410 is provided as part of the enhanced services server 116. The central database 410 is used to store data captured by the framework module 402, the A/R module 404, the clinical module 406, the scheduling module 408, and each of those module's various components. The central database 410 uses relational database technology (e.g., RDBMS) to manage all discrete data centrally, which facilitates the sharing of information across all modules and components of the integrated ambulatory suite 400. That functionality reduces the potential for redundant data entry and storage. And by allowing that data to be shared across all of the modules and components of the integrated ambulatory suite 400, the central database 410 avoids users having to enter information into clinical documents that has already been captured by the integrated ambulatory suite 400. It also ensures that all modules and components of the integrated ambulatory suite 400 have access to the most current version of that information.

F. Reference Databases

Figure 4:
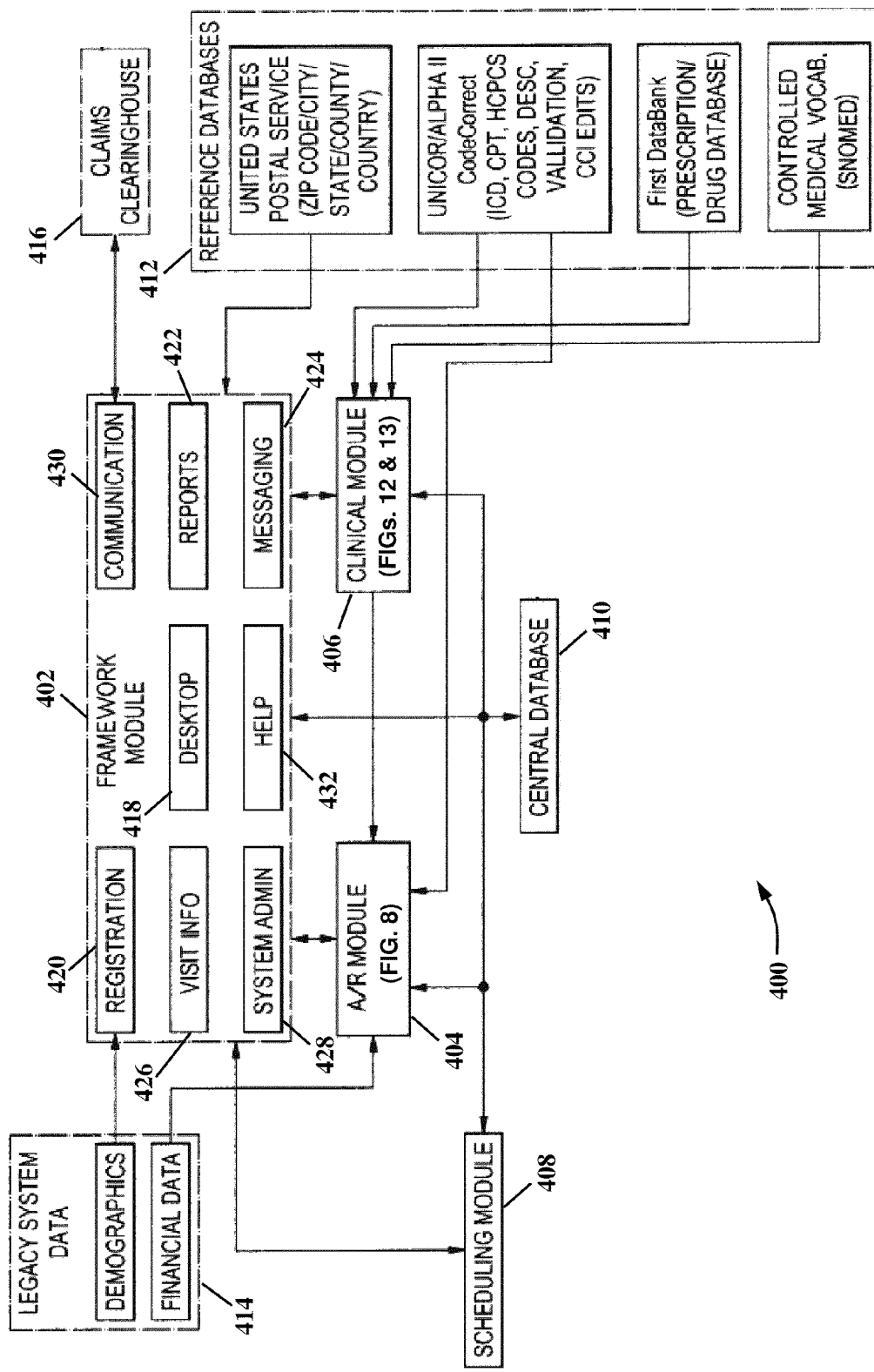
FIG. 4 is a schematic block diagram illustrating the functional makeup of the integrated ambulatory suite provided on the EHR systems in the integrated physician's network illustrated in FIG. 1.

The reference databases 412 maintain all reference information that is needed for the integrated ambulatory suite 400. As illustrated in FIG. 4, for example, the reference databases 412 include postal information, billing codes, drug information, and a controlled medical vocabulary. The postal information includes information on zip codes, cities, states, counties, and countries. The billing codes include insurance rules and regulations, such as ICD, CPT, and HCPCS codes and Correct Coding Initiative (CCI) edits. The CCI edits dictate which CPT code combinations and which ICD codes are valid to support certain CPT codes to ensure they are valid for obtaining payment for Medicare claims via the A/R module 404. The drug information includes descriptions of different drugs as well as unique identifiers and pricing information for each of those drugs, such as those provided in First DataBank, Inc.'s NDDF PLUS brand coded classification system. And the controlled medical vocabulary includes a collection of well-formed, machine-readable, and multi-lingual healthcare terminology that provides a standardized nomenclature for use in capturing, indexing, sharing, and aggregating healthcare data across specialties and sites of care, such as the SNOMED CT vocabulary.

G. Legacy Systems

The legacy system database 414 includes demographic data and financial data for patients from a prior healthcare practice management system. The data in the legacy system database 414 is imported from the prior healthcare practice management system through manual entry or by conversion of electronic information. The demographic information may include patients' names, addresses, dates of birth, ages, sexes, social security numbers, insurance coverage, and credit type. And the financial data may include patients' financial responsibility (e.g., credit rating), outstanding balances, insurance claims being processed, and other account information. The demographic data can be used by the registration component 420 to pre-populate required fields during the patient registration and visit check-in processes, which, in turn, can be used by the scheduling module 408 to schedule the patient and the clinical module 406 to pre-populate fields in various clinical documentation. And the financial data can be imported into the A/R module 404 via a financial migration utility and used to generate bills, claims, and statements for patients.

H. Order Management

To facilitate better order management, the integrated ambulatory suite 400 includes functionality for providing various clinical flags as well as functionality for tracking the completion of clinical documents. Clinical flags are used to provide clinicians and other staff members at a healthcare practice with various alerts, reminders, and recommendations for use during a patient's visit to the healthcare practice (e.g., during the check-in process, a physical examination, or other interaction with the patient). And the flow and completion of clinical documents, such as prescriptions and order, is tracked so that the status of those documents can be determined to ensure they are completed in a timely manner. Those features allow clinicians to more effectively serve their patients.

The alerts, reminders, and recommendations can be automatically generated as clinical flags based on standard health maintenance protocols, preferred treatment algorithms, or insurance rules for reimbursement. For example, if a patient's demographic information establishes that he or she is eighteen years old or older, a clinical flag can be automatically generated during an encounter with that patient to recommend screening him or her for high blood pressure, as recommended by the U.S. Preventive Services Task Force (USPSTF) for adults aged eighteen years and older. Clinicians can also request and/or define their own alerts, reminders, and recommendations and can define links to internal and external resources for clinician reference and patient education.

The status of various clinical documents is determined by automatically reviewing and tracking incoming and pending order results so that fulfillment is documented and failure to fulfill is investigated and remedied. For example, a clinician can have orders and/or prescriptions automatically generated for fulfillment by labs and/or pharmacies using the EHR component 1106 as they complete a clinical document. The integrated ambulatory suite 400 will log that such an order and/or prescription has been generated as well as each step in the fulfillment process. Accordingly, a clinician or patient can check the status of such orders and prescriptions via the integrated ambulatory suite 400. Moreover, the integrated ambulatory suite 400 will provide reminders to the clinician and other staff members at the clinician's healthcare practice if the order and/or prescription is not fulfilled within a predetermined time (e.g., the clinician will receive a message via the messaging component 424).

I. Automated Prescription and Order Fulfillment

Via its integrated modules and interfaces with outside systems, the integrated ambulatory suite 400 also provides automated prescription and order fulfillment. That automation is provided by the real-time electronic transfer of prescriptions and/or orders to pharmacies and/or labs as those prescriptions and/or orders are generated with the integrated ambulatory suite 400. The pertinent information is transferred directly from clinical documents to the fulfillment source without the need to duplicate the instructions in an intervening document or data entry process. That functionality reduces the amount of processing that would otherwise be required for prescription and/or order fulfillment.

BY way of example, using the drug information in the legacy databases 412 (e.g., the First DataBank, Inc.'s NDDF PLUS brand coded classification system), medications are automatically linked to corresponding drug identifiers and pricing information for use in generating electronic instructions for prescription fulfillment. When a clinician selects a medication to prescribe to a patient, such as in the medications subsection of a progress note, the drug identifier, pricing information, and other information required for the prescription is automatically transmitted to the pharmacy for fulfillment. As discussed above with respect to the registration component 420, pre-approval for prescriptions may be provided to further streamline the fulfillment process. When the prescription is completed, it is automatically documented in the patient's EHR.

The prescription refill process is also automated. Where a prescription has already been written for a patient, the clinician can select the prescription that was previously written to generate the refill. The clinician can then change the dosage or other aspects of the prescription as desired. And when the refill requires no changes to the previous prescription, the refill prescription can be generated and submitted for fulfillment by selecting the previously written prescription and making no changes. The refill is automatically documented in the patient's EHR and the instructions are electronically transmitted to the pharmacy for fulfillment.

Similar functionality is provided for generating orders. Thus, just as prescriptions are automatically transmitted directly from a clinical document to the participating pharmacy with the appropriate coding for billing and fulfillment, lab orders are automatically transmitted directly from a clinical document to the participating lab with the appropriate coding for billing and fulfillment (e.g., with LOINC classifications). And, just as prescriptions include any required drug identifiers and pre-approval, the orders include any required supporting diagnoses information and pre-approval.

J. Patient Access

The integrated ambulatory suite 400 also provides secured and structured two-way communication between the patient and the clinician, such as via an internet connection between a client workstation 106 and another user interface (e.g., a personal computer at the patient's home). The patient can submit post-treatment outcome results and status to the clinician in a predefined template. That allows the clinician to analyze the effectiveness of the treatment provided without the burden of reading free-text email. The increased patient interaction strengthens the clinician-patient relationship and increases the efficiency in scheduling appointments, registration, the interview process, and requesting prescription refills. That interaction is not only more convenient for the patient, but also allows the clinician's healthcare practice to shift a great deal of data entry from their clerical staff to the patient.

Patients can access the system through a centralized web portal, such as their clinician's website. The web portal allows the patient to perform limited functions with respect to appointment scheduling, patient interviews, prescription refill requests, personal health record (PHR) access, appointment follow-up information, and electronic consults. Patients can choose to be reminded of appointments electronically at various intervals before visits. Data from paper records can also be moved to the PHR. A PHR allows a patient to track visits to a clinician, medications, in-home observations of blood sugar, vital signs, etc. It is effectively an EHR that is in the control of the patient, rather than the clinician.

K. Audit Logging and Security

In addition to the audit logging performed by the messaging component 424 of the framework module 302, audit logging is also performed throughout the system to assist system administrators in enforcing practice policies and compliance with regulations. Security options include username and password and/or biometric identification for access control. The username allows role-based and/or user-based control of permission to use various system functions. That audit logging is of particular usefulness in complying with the patient data access and disclosure requirements of HIPAA.

III. Speech Understanding Functionality

As discussed above, much of the data captured in clinical documents with the integrated ambulatory suite 400 can be captured using speech understanding functionality. That speech understanding functionality is embedded in the various modules and components of the integrated ambulatory suite 400. Through seamless integration with the various modules and components of the integrated ambulatory suite 400, the data captured in clinical documents using the speech understanding functionality is processed in the same manner as the data captured by other mechanisms (e.g., text typed in with a keyboard). More particularly, that data is captured and stored using uniform, standardized medical vocabularies and is transmitted using uniform messaging, document, and form management standards so that it can be used throughout the integrated ambulatory suite 400, not just in the clinical document in which it was captured. And because the speech understanding functionality is embedded within the modules and components of the integrated ambulatory suite 400, users do not need to familiarize themselves with and accept new software. Moreover, by allowing clinicians to continue to use a form of data capture with which they are already familiar—dictation—the speech understanding functionality helps transition new users of the integrated ambulatory suite 400 into the electronic record-keeping medium.

A. Transcription Engine

The speech understanding functionality of the integrated ambulatory suite 400 is embedded within the modules and components of the integrated ambulatory suite 400 so that it can be accessed and utilized to input substantially any type of data. For example, it can be used to input clinical data with the EHR component 1106 during an encounter with a patient or to input demographic information, financial information, and/or administrative information with the registration component 420 during a check-in or registration process. By "embedded" it is meant that the speech understanding functionality is integrated within the standard clinical workflows utilized by a user. Accordingly, the speech functionality operates seamlessly within the specific modules and components of the integrated ambulatory suite 400 in which it is being utilized. And it can be initiated and utilized within each of those modules and components without leaving the page/application in which the user is working.

The speech understanding functionality of the integrated ambulatory suite 400 supports two primary speech-driven functions—1) the selection of predefined fields, text, sections, etc. within electronic documents and 2) the real-time dictation of freeform text into the fields and sections of electronic documents. The former involves direct speech-to-text conversion, and the latter involves receiving dictation and transcribing it into written text. For example, speech commands can be received to select a choice from a list defined by a make multiple select control type, and dictation can be received to write a sentence from scratch in a field defined by a make input box control type. Both of those speech-driven functions require the speech understanding functionality to transform spoken words into electronic data.

The data transformation performed by the speech understanding functionality includes taking the audio signals associated with spoken words and translating them into electronic commands/selections or into electronic text. That transformation can be performed by the processor of the client server 104 or a processor in another system being used by a clinician or other healthcare practice staff member to capture data at the healthcare provider's site 102 (e.g., a tablet computer or client workstation connected to the client server 104 at the healthcare provider's site 102). Or the audio signals can be streamed to a system outside of at the healthcare provider's site 102 for remote processing, such as by the enhanced services server 116 of an IPI provider system or the processor of an external system 142 (e.g., an external electronic medical transcription system, such as that provided by MultiModal Technologies, Inc. (M*Modal). Even when an external system is used to process the signals of the dictated information into text, those signals are processed in near real time so that the module or component in which the clinician or other healthcare practice staff member is working can quickly respond to the words being spoken.

When a user speaks a speech command (e.g., "Chief Complaint."), the spoken selection within the module or component in which the clinician or other healthcare practice staff member is working will automatically be highlighted and/or selected in response to the command. And when a speech command is used to make a selection from a predefined list, selections that will effect data in other sections of a clinical document and/or that will be used by other modules or components (e.g., a diagnosis selected from a pull-down menu) will already be linked to the appropriate coding (e.g., ICD, RxNorm, LOINC, CPT, E&M, and HCPCS codes), flags (e.g., administrative flags and clinical flags), and other related data (e.g., body systems, assessments, and plans) based on the default settings defined using the template builder component 1102, as discussed above. Those speech commands are associated with selections using the speech understanding functionality of the present invention. Accordingly, speech commands allow a clinician or other healthcare practice staff member to quickly input data into clinical documents that will flow throughout the integrated ambulatory suite 400 to support other automated process, such as automatically generating the appropriate billing codes for claims and submitting those claims for payment.

When a user recites dictation (e.g., "Patient has had a cough for the past week."), the corresponding text is automatically transcribed and populated into the selected field or section of the clinical document in which the clinician or other healthcare practice staff member is working. But, because such transcribed text is not already linked to the appropriate coding and flags, it is translated into a uniform, structured language format, such as the XML format, as it is processed so the corresponding text can be manipulated as required for storage and data linking. Accordingly, it may take longer to process dictated information than speech commands, in which case it may take a few seconds after the clinician or other healthcare practice staff member is done speaking for the dictated information to appear as text in the field or section of the clinical document in which he or she is working.

Figure 39:
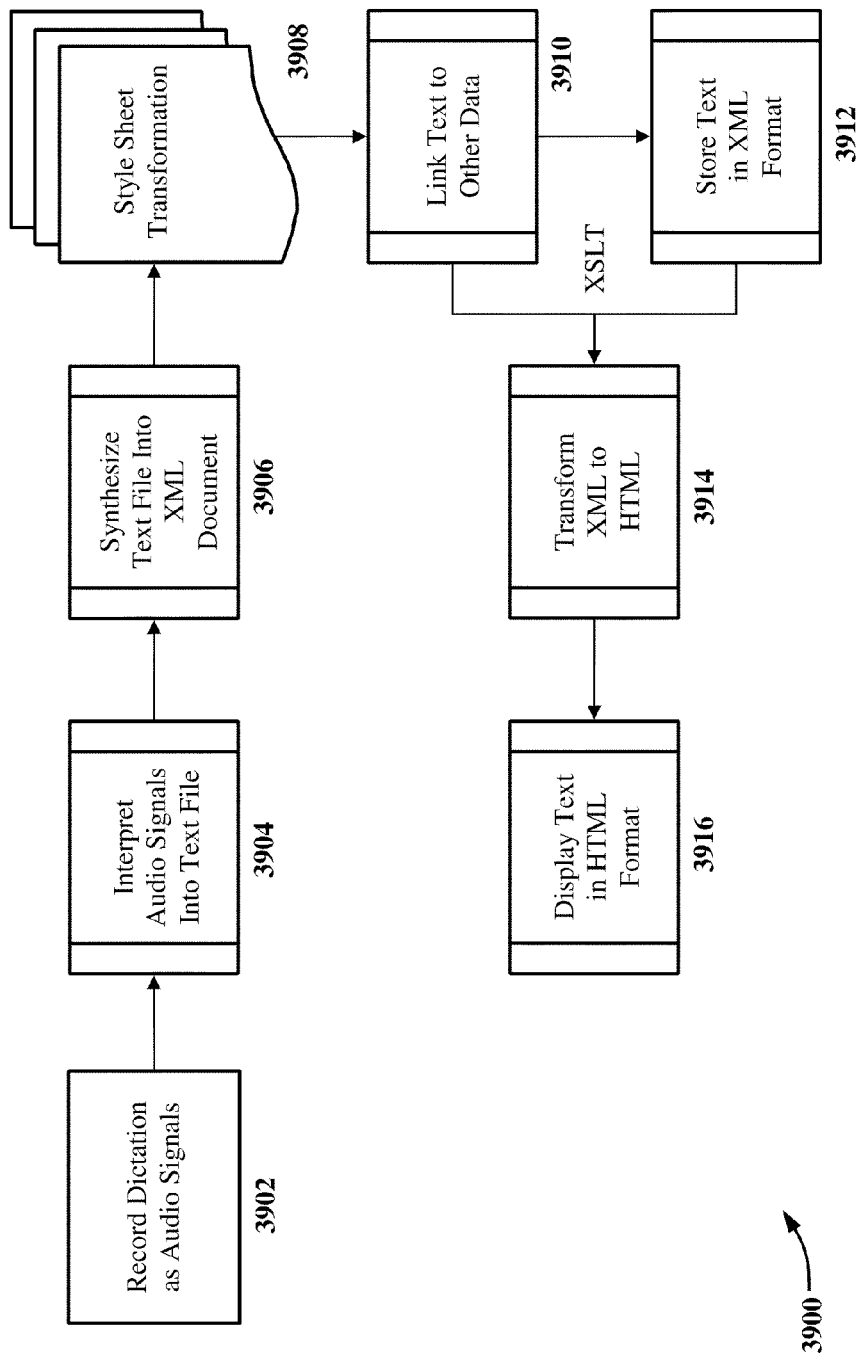
FIG. 39 is a flow chart depicting a process for transcribing and linking dictated text according to a non-limiting embodiment of the present invention.

As FIG. 39 illustrates, a transformation process 3900 used to transcribe, link, and store dictated text in the integrated ambulatory suite begins with the step 3902 of recording the audio signals associated with the words spoken by the clinician or other healthcare practice staff member. Those audio signals are recorded with any suitable electronic audio recording device in electronic data communication with the present invention (e.g., cellular telephone, switched telephone, dictation microphone 4000, etc.). Those audio signals are then translated into text at step 3904 of the transformation process 3900 using the speech understanding functionality of the present invention. But because the words spoken as dictation are freeform rather then based on predefined selections, the speech understanding functionality may be provided with speech understanding capability, wherein it is calibrated to a specific user's voice for more accurate recognition of the words being spoken by that user. The speech understanding functionality utilizes semantic interpretation, such as the Semantic Interpretation for Speech Recognition (SISR) recommended by the a World Wide Web Consortium (W3C), to describe the meaning the words spoken by the clinician or other healthcare practice staff member in a form that can be understood by a processor, such as an ECMAScript text file. The resulting text is then stripped of any tags associated with it during semantic interpretation and the resulting text file is serialized into an XML document at step 3906 of the transformation process 3900 so that it may be more easily manipulated.

In the XML format, the text associated with the words spoken by the clinician or other healthcare practice staff member can be parsed out to determine their meaning, which allows them to be linked to the appropriated coding, flags, and other related data. For example, the W3C's Speech Recognition Grammar Specification (SRGS) can be used to specify a grammar tree with the possible word and phrase sequences that could be spoken by the clinician or other healthcare practice staff member, to generate runtime information when a word or phrase is recognized, and to specify languages and semantics types. Each of the words or phrases in the grammar tree can be linked to a grammar that is independent of the words spoken by the clinician or other healthcare practice staff member when the associated word or phrase is recognized. And the words and phrases that determine those linkages are based on terminologies currently in clinical use, such as those defined in Global Medical Transcription, LLC's common medical vocabulary. For example, when the phrase "fractured upper arm" is recognized, the ICD code "818.0" associated with that diagnosis will automatically be linked to that phrase so it can be used to generate a claim for that diagnosis.

Other examples of linking transcribed text include: linking an insurance plan transcribed during a registration process in the registration module 420 to a fee schedule that will be used by the A/R module 404 to determine an allowed amount for a bill, claim, and/or statement; linking a sex transcribed during a registration process in the registration module 420 to a demographic information control type so gender-specific pronouns (e.g., he/she, him/her, himself/herself, and his/her) will be automatically populated into a clinical document by the clinical module 406; linking an age and/or date of birth transcribed during a registration process in the registration module 420 to a clinical flag (e.g., "Screen Patient for High Blood Pressure.") that will be automatically generated by the clinical module 406 during an encounter with the patient; linking a date and/or time transcribed in the scheduling module 408 during a scheduling process to a date stamp control type so the date and/or time of a scheduled patient encounter will be automatically populated into a clinical document by the clinical module 406; and linking a prescription transcribed in an assessment/plan section of a clinical document in the clinical module 406 to an RxNorm code that will be used by the A/R module 404 to automatically generate a bill, claim, and/or statement. Such linking occurs at step 3910 of the transformation process 3900.

Because different words and phrases can have different meanings based on the field, section, and/or clinical document in which that word or phrase is input, certain grammars will only be active in certain fields, sections, and/or clinical documents. For example, when the phrase "fractured upper arm" is recognized in the History of Present Illness Section of a Progress Note, it will be linked so that the corresponding body system appears in the Review of Systems section of the Progress Note. But when the phrase "broken arm" is recognized in the Assessment/Plan section of a Progress Note, it will be linked to the associated diagnosis code, as discussed above. That phrase is treated differently in those different sections because a history of upper arm fractures is different than the present diagnosis of an upper arm fracture.

Because the linking that occurs at step 3910 of the transformation process 3900 will depend on the field, section, and/or clinical document in which a word or phrase is input, the XML document generated at step 3906 of the transformation process 3900 must be transformed with style sheets at step 3908 of the transformation process 3900 before that linking can occur. The XML document is transformed according uniform document standards (e.g., CCD, CDA, or CCR) using XSLT processing at step 3908 of the transformation process 3900. That transformation breaks the text of the XML document out into the associated fields and/or sections of the clinical document defined by the associated style sheet. Accordingly, the XML document created at step 3906 of the transformation process 3900 will include not only the text associated with the words spoken by the clinician or other healthcare practice staff member, it will also include text associated with the field and/or section in which the clinician or other healthcare practice staff member was working when those words were spoken.

After the XML document is transformed using style sheets at step 3908 of the transformation process 3900 and linked to the appropriate coding, flags, and other data at step 3910 of the transformation process 3900, the corresponding information is stored in a central location (e.g., on the central database 410) at step 3912 of the transformation process 3900 so it can be used by and seamlessly shared between the modules and components of the integrated ambulatory suite 400. And at step 3914 of the transformation process 3900, the data can be transformed into a modified XML (e.g., HTML) using XSLT processing so the clinician or other healthcare practice staff member can view his or her spoken words as written text at step 3916 of the transformation process 3900. The written text is displayed at the user interface and it can be presented to a user in near real time as the associated information is linked to the appropriate coding, flags, and other data at step 3910 of the transformation process 3900, or it can be queried from the central storage location at a later time.

As demonstrated by the transformation process 3900 illustrated in FIG. 39, the speech understanding functionality of the integrated ambulatory suite 400 performs like a hybrid between a front-end and back-end speech recognition engine. It provides front-end type functionality because words spoken by the clinician or other healthcare provider are displayed right after they are spoken and the person speaking those words is responsible for editing and signing off on the transcribed text. And it provides back-end type functionality because the manipulation of the text using style sheets acts as an automated medical transcriptionist by associating the transcribed text into the appropriate sections of a clinical document while linking that text to codes, flags, and other related data.

B. Dictation Microphone

The only additional hardware required to utilize the speech understanding functionality of the integrated ambulatory suite 400 is a dictation microphone 4000 for recording dictation and receiving speech commands. Depending on the type of dictation microphone 4000, a microphone utility may need to be installed on the client workstation 106 or other user interface so that the dictation microphone will operate properly with the client workstation 106 or other user interface. The microphone utility may also allow a user to program various buttons on the dictation microphone.

Turning to FIG. 40, an exemplary dictation microphone 4000 is illustrated that includes a microphone receiver 4002, a speaker 4004, a record button 4006, an end-of-line (EOL) button 4008, a play/stop button 4010, a rewind button 4012, a fast forward button 4014, a roller ball 4016, an enter button 4018, a move forward button 4020, a move backward button 4022, and a plurality of customizable buttons 4024. The microphone receiver 4002 transforms the mechanical vibrations of a user's voice into electronic signals as the user speaks into the dictation microphone 4000. The speaker 4004 converts electronic signals into audible vibrations to replicate the user's voice during dictation playback. Pressing the record button 4006 initiates the recording of dictation. Pressing the EOL button 4008 stops a recording of dictation and advances the transcribed text to the next line. Pressing the play/stop button 4010 initiates dictation playback when pressed the first time and stops dictation playback when pressed a second time.

Pressing the rewind button 4012 moves dictation playback backward in time. Pressing the fast forward button 4014 moves dictation playback forward in time at a faster rate than it was recorded. The roller ball 4016 operates like a mouse and moves a cursor displayed at the client workstation 106 or other user interface. Pressing the enter button 4018 operates as an execute key that causes commands to be executed, such as selecting an item over which a cursor is placed with the roller ball 4016. And the plurality of customizable buttons 4024 can be programmed to perform other specific commands for taking and playing back dictation (e.g., start a new paragraph, start a new section, undo, redo, delete, quote, etc.). That functionality may be provided, for example, with the SPEECH MIKE PRO PLUS brand dictation microphone manufactured by Philips Electronics N.V.

Although the dictation microphone 4000 of FIG. 40 includes a roller ball 4016 and several buttons 4002-4014 and 4018-4024 for the user to interface with the client workstation 106 or other user interface, a dictation microphone without those features may also be used. When a dictation microphone without such features is used, the functionality of the roller ball 4016 and several buttons 4002-4014 and 4018-4024 may be provided by substantially any other means, such as a keyboard and/or a mouse.

C. Receiving Speech Commands and Taking Dictation

To facilitate ease of use, the speech understanding functionality of the integrated ambulatory suite 400 may be set up to load upon startup of the client workstation 106 or other user interface that is used to interact with the integrated ambulatory suite 400. Accordingly, as soon as a user is working within the integrated ambulatory suite 400, the user can perform substantially any task using speech commands and/or dictation. For example, the user can register a patient using the registration component 420 of the framework module 402; generate a bill using the A/R module 404; create, edit, or complete a clinical document using the clinical module 406; and schedule a patient using the scheduling module 408. The user can also use the speech understanding functionality to create, edit, and complete research documentation, as discussed in more detail below with respect to the present invention's research functionality.

By way of further example, a clinician can use the speech understanding functionality of the present invention to complete clinical documentation, such as a progress note. To complete a progress note for a patient, the clinician selects the patient from the desktop 500 (FIG. 5) and then selects the "Chart" option from the menu bar 502. Within the "Chart" option, the clinician can then select the "Create Progress Note" option, which will open a progress note. The clinician can make those selections manually via the click of a mouse or verbally via speech commands (e.g., by saying "Select Patient."—"[Patient Name]."—"Chart."—"Create Progress Note." into the dictation microphone 4000). The clinician can then create the progress note by selecting the various templates that will form the progress note, and the progress note will be automatically populated with the predefined sections for those templates and any data already available within the integrated ambulatory suite 400 (e.g., patient demographic data, history of present illness data, etc.), as discussed above. Although the following example is discussed in terms of a progress note, any type of clinical document supported by the integrated ambulatory suite 400 can be created, edited, and/or completed in a similar manner to that disclosed.

The clinician makes selections via speech command by holding down the record button 4006 of the dictation microphone 4000 and stating each selection. The clinician should release the record button 4006 between each command to signify that the command is complete and should be processed (indicated by the dashes "-" in the preceding parentheticals). Clinicians and other healthcare practice staff members can navigate through the various modules and components of the integrated ambulatory suite 400 in a substantially similar manner—namely, by speaking commands into the dictation microphone 4000 that correspond to options and headings displayed while that user is working in the various modules and components of the integrated ambulatory suite 400.

Figure 41:
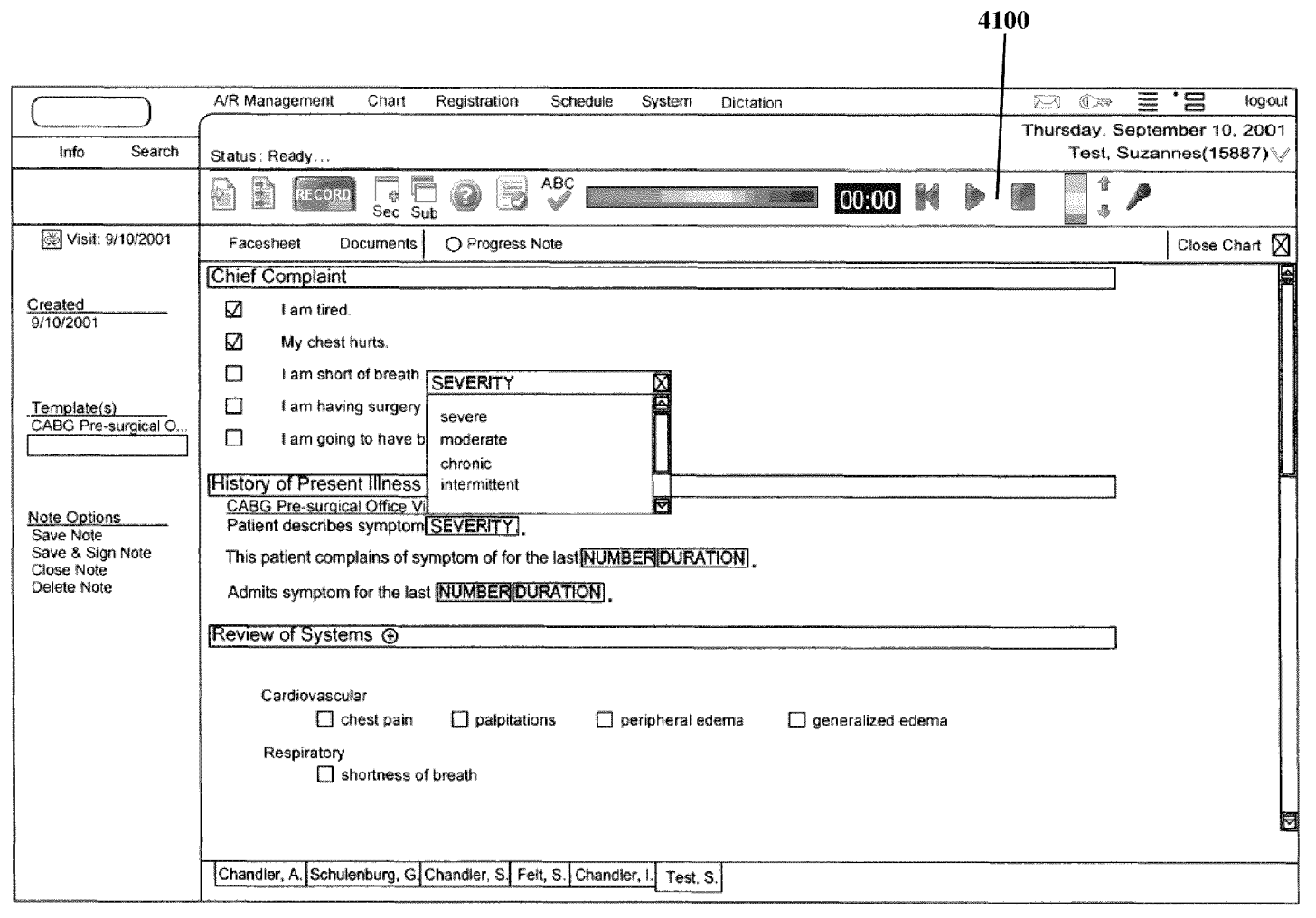

With the progress note opened and pre-populated with all of the pertinent data that is already available for a patient, the clinician can begin completing the remaining portions of the progress note via dictation by selecting the "Dictation" option from the menu bar 502 and then selecting the "Create Dictation" option within the "Dictation" option. Upon selecting the "Create Dictation" option, a dictation toolbar 4100 will be displayed in the document in which the clinician is working, as illustrated in FIG. 41. The dictation toolbar 4100 is provided to assist the clinician and other users in creating, editing, and completing clinical documentation within the integrated ambulatory suite 400. That clinical documentation includes the clinical documents created using the template builder component 1102 and document builder component 1104 of the clinical module 406 as well as other documents supported by the integrated ambulatory suite 400, such as scanned in documents or documents imported using the RFD functionality discussed above.

Figure 42:
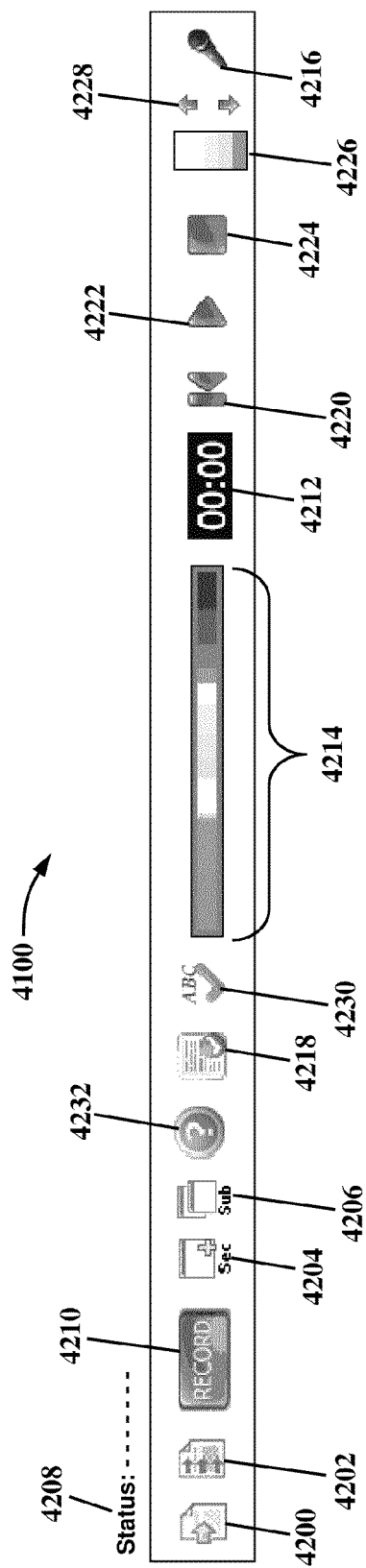
FIG. 42 illustrates a dictation toolbar according to a non-limiting embodiment of the present invention.

As illustrated in more detail in FIG. 42, the dictation toolbar 4100 includes a full import button 4200, a partial import button 4202, a section button 4204, a subsection button 4206, a dictation status indicator 4208, a record button 4210, a dictation timer 4212, a dictation record volume indicator 4214, a microphone calibration button 4216, a sign and save button 4218, a restart dictation playback button 4220, a start dictation playback button 4222, a pause dictation playback button 4224, a dictation playback volume indicator 4226, dictation playback volume controls 4228, a learn button 4230, a spell check button 4230, and a help button 4232. Any of those buttons may also be provided in other locations, such as in an actions section of the Desktop 500. The clinician or other healthcare practice staff member can make selections from among those buttons 4200-4232 using corresponding speech commands, by using the roller ball 4016 and enter button 4018 on the dictation microphone 4000, or via any other suitable user input device (e.g., a mouse).

Selecting the full import button 4200 on the dictation toolbar 4100 allows the clinician to import all of the completed sections from a patient's face sheet 3700, such as medical history, medications, allergies, surgical history, problem list, etc. And selecting the partial import button 4202 allows the clinician to import only specific sections from the face sheet 3700. The clinician or other healthcare facility staff member can move previously transcribed text into a new section or subsection by selecting the section button 4204, or by selecting the subsection button 4206. And the clinician or other healthcare facility staff member can add multiple levels of sections and subsections as desired. The format of the sections and templates defined with the template builder component 1102 support the importation of data from the sections of one clinical document to another. That process can be used to build and complete clinical documents, such as Progress Notes.

After importing any completed sections from a completed progress note that the clinician wants to reuse in the current progress note, the clinician can complete the remaining sections or empty portions of the imported sections via dictation. To begin dictating text into a section of the progress note, the clinician holds down the record button 4006 on the dictation microphone 4000, or selects the record button 4210 on the dictation toolbar 4100, and states the name of the section in which he or she wants to begin dictating text (e.g., stating "Chief Complaint."). The text to the right of the dictation status indicator 4208 will read "Status: Ready . . . " when that section is ready to begin receiving dictation. The clinician then hits the record button 4006 on the dictation microphone 4000, or selects the record button 4210 on the dictation toolbar 4100, either of which will cause the record button 4210 to illuminate and the dictation timer 4212 to begin counting up from "00:00" seconds. As the clinician dictates into the microphone receiver 4002 of the dictation microphone 4000, the dictation volume indicator 4214 will illuminate stepwise to indicate the volume at which the clinician's dictation is being recorded. The clinician can observe that volume to ensure that he or she is not speaking so loud as to cause clipping, which would cause the recognition of his or her dictation to be less accurate. The clinician can adjust that volume by selecting the microphone calibration button 4216 and calibrating the level at which the dictation microphone 4000 records.

As discussed above, the electronic signals translated from the vibrations of the user's voice are processed to convert the dictated information into corresponding text as the clinician or other healthcare practice staff member dictates information into the microphone receiver 4002 of the dictation microphone 4000. Those signals are processed in real time (e.g., by the client server 104 or a processor in another system) as the user speaks, during which time the text to the right of the dictation status indicator 4208 will read "Status: Recording . . . ". If the signals take additional time to process after the user is done recording then the text to the right of the dictation status indicator 4208 will read "Status: Processing . . . " as the signals continue to be processed. The clinician or other healthcare practice staff member can edit his or her dictated text as soon as it has been fully processed, at which time the status indicator 4208 will read "Status: Ready for edit."

As discussed above, the signals are converted into the XML format as they are processed so they can be manipulated with the style sheets to identify discrete data and make the appropriate links with that data. Because the data input with the speech understanding functionality is linked to the appropriate coding and flags as a clinician or other healthcare practice completes clinical documents, all of the integrated functionality of the various modules and components of the integrated ambulatory suite 400 is preserved. That data may be actively linked with style sheets as it is input by the user, as discussed above, or it may already be linked to data from which the clinician or other healthcare practice staff member can select. For example, the findings listed in the physical exam section of a clinical document will already be linked to the corresponding bullets and sub-bullets of the E&M codes, the diagnoses in the assessment subsection of a clinical document will already be linked to the corresponding ICD codes, and the orders listed in the orders subsection of a clinical document will already be linked to the corresponding CPT codes. Thus, when a clinician uses the integrated functionality of the present invention to select from a list of those findings, diagnoses, and/or orders, the corresponding ICD, CPT, E&M, HCPCS, RxNorm, and LOINC codes will automatically be linked to billing codes as the clinician makes his or her selections, which facilitates the A/R module 404 automatically generating a bill, claim, or statement for a patient.

The clinician can complete the various sections of the progress note in several different ways. He or she can select options from a list, input or select options for various control types, or dictate entire sentences into the sections. The lists (e.g., lists of chief complaints or body systems) and control types (e.g., care provider list, date stamp, duration, measurement, make input box, number selector, make multiple select, make select list, and demographic information control types) can be defined using the template builder component 1102, as discussed above.

If the clinician must select from a list to complete a section, the clinician can read the text that corresponds to the desired selection (e.g., stating "I am tired" and then "My chest hurts" in the chief complaint section illustrated in FIG. 29). And if the corresponding section includes sentences with control types that require input from or selection by the clinician, the clinician can input text or select from those control types by stating the corresponding control type identifier provided in the sentence and then stating the text that corresponds to the desired input or selection (e.g., stating "Severity" and then "Severe" in the history of present illness section illustrated in FIG. 29, or reciting text into a make input control type). As discussed above with respect to the EHR component 1106, the fields into which the clinician can input or select data are surrounded by a box that indicates that the speech understanding functionality is enabled for the make input box. The control type identifier that the clinician needs to state to open such a field will be written in that box (e.g., "SEVERITY", "NUMBER", and "DURATION" in the history of present illness section illustrated in FIG. 29). The control type in which the clinician is working will provide some visible indication so the clinician knows which control type he or she is working in (e.g., the appearance of a pull-down menu or a blinking cursor in the box). Using speech commands, the user will be able to navigate to the next control type. The user can also navigate between control types and sentences using the move forward button 4020 and the move backward button 4022 on the sides of the dictation microphone 4000.

After inputting text or making selections for each control type within a sentence, the clinician can move to the next sentence by pressing in EOL button 4008 on the dictation microphone 4000, by making an appropriate speech command (e.g., by saying "Next sentence." into the dictation microphone 4000), or by using the move forward button 4020. After the last sentence is complete, pressing the EOL button will move the clinician to the next section. The clinician can also move to the next section at any point using corresponding speech commands (e.g., by saying "Next Section." into the dictation microphone 4000), by using the roller ball 4016 and enter button 4018 on the dictation microphone 4000 to select that section, or by selecting that section via any other suitable user input device (e.g., a mouse). The clinician or other healthcare practice staff member can navigate forward and backward through sentences and sections within any clinical document in a substantially similar manner.

If the clinician prefers to complete sections of a progress note or other clinical document without the use of lists or control types, the clinician can also dictate entire sentences into those sections. The clinician inputs complete sentences into sections in substantially the same manner as he or she selects items from a list or inputs or selects data for control types—in particular, by pressing the record button 4006 on the dictation microphone 4000, or selecting the record button 4210 on the dictation toolbar 4100, and speaking full sentences into the microphone receiver 4002 of the dictation microphone 4000. As those full sentences are dictated into the sections of the progress note, they begin to appear in the corresponding section of the progress note as typed text. The clinician can create various sections and subsections in which those dictated sentences will appear using the section button 4204 and the subsection button 4206, as discussed above.

Unlike selecting from a list or selecting from control types where the clinician's selections are limited to the pre-defined text, inputting text into a make input box control type and inputting complete sentences into a document section allow errors to occur in the corresponding text based on errors in speech understanding and dictation. Accordingly, the clinician can make corrections to the text as it is displayed after transcription, similar to front-end speech recognition, or he or she can send the clinical document to a medical transcription/editing service for review and correction of the transcribed text, similar back-end speech recognition. Thus, the speech understanding functionality of the present invention provides the clinician with the option of using front-end or back-end correction techniques.

Preferably, the clinician will only use back-end correction techniques for more complex and detailed clinical documents that require the input of large amounts of data and that do not require a quick turn-around. Reserving back-end correction for those types of documents helps reduce the costs associated with paying a medical transcription/editing service to review and edit clinical documents. The clinician will preferably use front-end type correction techniques for all other clinical documents, particularly those that require a quick turn-around. Accordingly, when the clinician finishes dictating information into a progress note or other clinical document and selects the sign and save button 4218, he or she may be presented with an option to sign the document in its current condition or to send the document to a medical transcription/editing service for back-end correction before signing the document.

The clinician can review the audio file that will be submitted to the medical transcription/editing service after recording it by selecting the restart dictation playback button 4220, which will return the recording to its beginning (i.e., 00:00 seconds). The clinician then presses the a play/stop button 4010 on the citation microphone 4000, or selects the start dictation playback button 4222 on the dictation toolbar 4100, to begin playback, pausing playback as necessary using the play/stop button 4010 and/or the pause dictation playback button 4224. As the dictation is played back to the clinician, the volume at which the dictation is played back is indicated by stepwise illumination of the dictation playback volume indicator 4226. The clinician can adjust that volume up and down using the corresponding dictation playback volume controls 4228. If the clinician wants to replace any portion of the dictation, he or she can pause the dictation playback at the desired point by pressing the play/stop button 4010, or selecting the pause dictation playback button 4224, and then holding down the record button 4006 of the dictation microphone 4000, or holding down the record button 4210 on the dictation toolbar 4100, to record over the subject portion of the dictation.

When the clinician wants to edit dictated text him- or herself using front-end correction techniques, he or she selects the section in which the subject text is displayed and identifies the text that he or she wants to correct. For example, to change the term "nonproductive" to "productive" in a sentence in the history of present illness section that recites "The patient is a 35-year-old white male and has a four-day history of nonproductive cough.", the clinician states "Section."—"History of Present Illness." to select the history of present illness section and begin editing. Upon selecting that section, the status indicator 4208 will read "Status: Ready for edit." Or in the alternative, if the clinician has just completed dictating the subject text in that section, the status indicator 4208 will read "Status: Ready for edit." as soon as that dictated text is processed. Then, to edit the term "nonproductive", the clinician states "Select."—"Nonproductive.", which will cause the term "nonproductive" to be highlighted in the history of present illness section. The clinician can then speak the replacement word "productive" while holding down the record button 4006 of the dictation microphone 4000, or holding down the record button 4210 on the dictation toolbar 4100, and the highlighted word will be changed to that replacement word. In each of those commands, the dash "-" represents a break in different commands spoken.

Words, phrases, and/or entire sentences can be corrected in various sections of various clinical documents in that same manner. The clinician can also select words for replacement using the roller ball 4016 and enter button 4018 or any other suitable input device (e.g., a mouse) to select an "Edit" option within the "Dictation" option in the menu bar 502 and to highlight the text or phrase in the desired section. The clinician can then dictate replacement text into the highlighted section as discussed above.

Whenever a user is done making a correction to dictated text, which may be indicated by the user selecting the sign and save button 4218, the corrected information will be automatically saved on the central database of the enhanced services server 116 as part of a voice profile. The speech understanding functionality will then use the information in that voice profile to better recognize that user's voice and mannerisms and to ensure that the same mistakes are not made in the future. And by saving that voice profile on the enhanced services server 116, it can be accessed and used at any client workstation 106 within the IPI 100, such as via "cloud" computing. Accordingly, the user will not need to physically carry around a portable electronic storage medium (e.g., a CD-ROM or zip disk) with his or her voice profile for use with different client workstations 106. Moreover, the user will not need to correct the same dictation mistakes over and over again.

To further assist a clinician or other staff member of a healthcare practice check the text he or she dictated into a document, a spell check button 4230 and help button 4232 are also provided in the dictation toolbar 4100. Selecting the spell check button 4230 will result in each word within the dictated text being checked to ensure it is spelled properly. Improperly spelled words will be identified and replacement words suggested. By selecting a replacement word, the incorrectly spelled word will be replaced with the selected replacement word. And selecting the help button 4232 will navigate the user to a help screen at which the user can obtain guidance on how to perform various tasks and/or trouble-shoot any issues. Persons having ordinary skill in the art will readily appreciate the manner in which the functionality associated with the spell check button 4230 and the help button 4232 operates.

As discussed above, a clinician may also decide to forego such front-end editing functionality and route the clinical document to another staff member for back-end editing. That staff member may be a designated editor, and the document can be transmitted to that editor via electronic communications between systems within the IPI 100. The editor can open the transcribed document at a client workstation 106, listen to the dictation, and modify the text as required based on the speech playback. After the editor is done editing the document, the document is transmitted back to the clinician who authored it for final review and signature.

By providing clinicians and other users with the ability to quickly turn around dictation to transcription and to immediately correct that dictation, the speech understanding functionality of the present invention increases the efficiency of clinical document completion. And by linking the transcribed dictation to the appropriate coding, etc., the speech understanding functionality of the present invention also increases the efficiency of the various automated functions of the integrated ambulatory suite 400, such as automatically generating bills, claims, and statements as clinical documentation is completed by a clinician. And by allowing users to immediately make corrections to transcribed dictation and save those corrections, the accuracy of the speech understanding functionality is continuously improved for subsequent transcription.

IV. Research Functionality

The research functionality of the present invention may be used to quickly and accurately locate a large number of patients for participating in a clinical trial by running a sequential filtering process across the systems of the IPI 100 (FIG. 1). By utilizing an IPI 100 that includes a large network of EHR systems built on the same architecture, the filtering process can be run quickly and accurately across the databases on each client server 104 and/or querying a central database on the enhanced services server 116. And, where the IPI 100 is employed on a national scale, the results of that filtering process provide a larger pool of patients, and therefore a more desirable cross-section of people, from which researchers can recruit participants for clinical trials. For example, utilizing the present invention over Greenway Medical Technologies, Inc.'s IPI will provide researchers access to data for more than twenty million active patients collected at more than fourteen hundred sixty healthcare provider sites across the continental United States and Puerto Rico. Collecting, tracking, and analyzing data on such an expansive scale is indicative of the present invention's functionality.

Thus, a clinical trial sponsor, such as a pharmaceutical company, can utilize the present invention to quickly and accurately identify and register patients that qualify for clinical trials. The clinical trial sponsor can become a partner with the IPI provider and utilize the functionality of the present invention to locate patients within the IPI 100 network that qualify for a clinical trial, or the clinical trial sponsor can solicit proposed clinical trials through Clinical Research Organizations (CROs) who will become partners of the IPI provider and utilize the functionality of the present invention to locate patients within the IPI 100 network that qualify for a proposed clinical trial. To utilize that functionality, the clinical trial sponsor or CRO will develop specific clinical criteria that patients must satisfy to qualify for participation in the clinical trial. Those criteria are given to the IPI provider, who utilizes the present invention to run a sequential filtering process 4400 (FIG. 44) and determine the number of patients within the network of the IPI 100 that qualify for the clinical trial. In the alternative, the clinical trial sponsor or CRO may utilize the present invention to run the sequential filtering process. But, before a clinical trial sponsor or CRO obtains access to the network of the IPI 100 and/or the data captured thereon, the clinical trial sponsor or CRO must register as a research partner of the IPI provider and agree to certain provisions to ensure compliance with HIPAA's regulations.

A. Partner Registration Process

Figure 43:
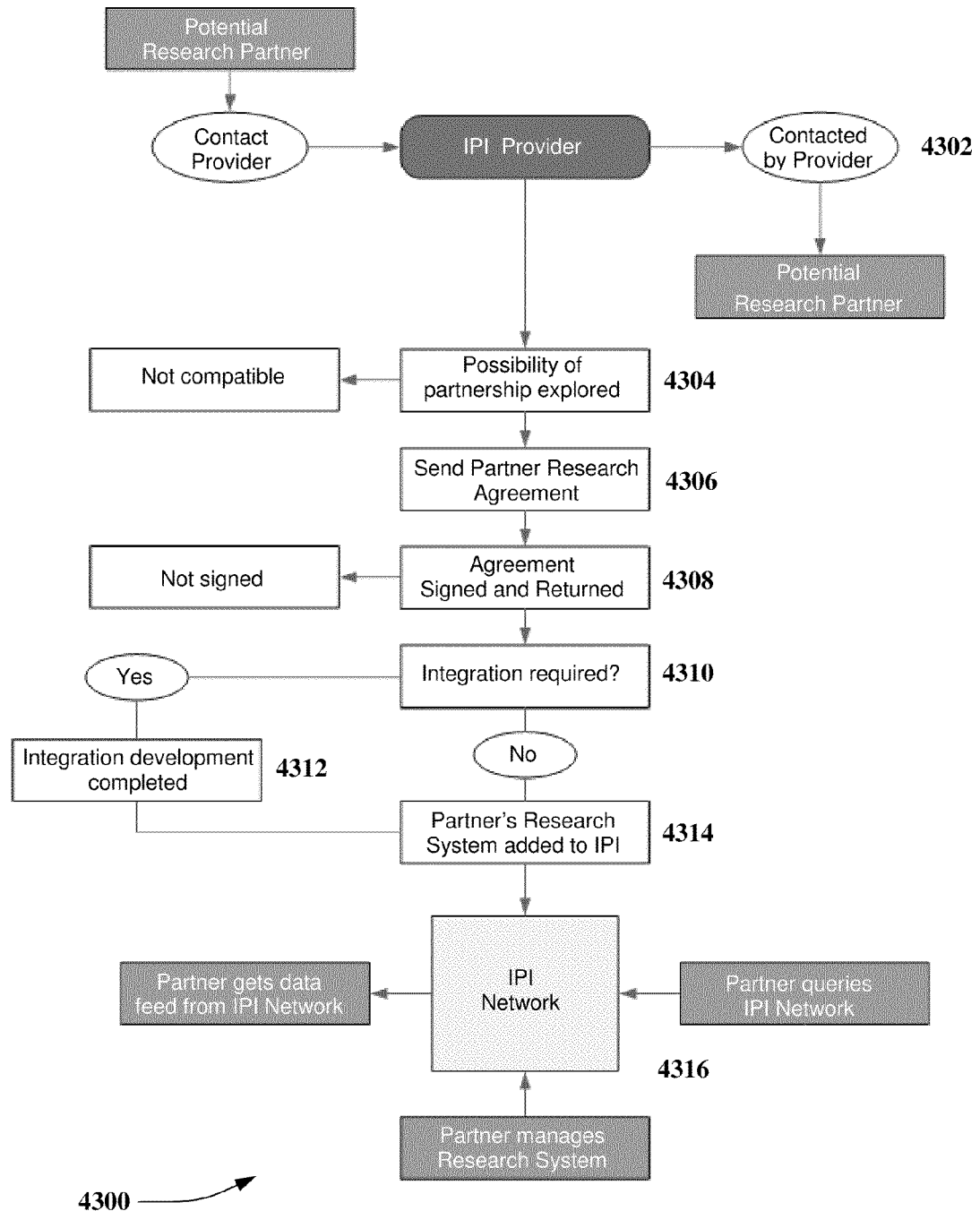
FIG. 43 is a schematic block diagram illustrating the functional steps of a partner registration process according to a non-limiting embodiment of the present invention.

As FIG. 43 illustrates, the partner registration process 4300 includes several steps before a potential research partner can utilize the functionality of the present invention. At step 4302 of the partner registration process 4300, a potential research partner can contact the IPI provider or the IPI provider can contact the potential research partner via any suitable means, such as via a link on the IPI provider's internet home page or via an e-mail. At step 4304 of the partner registration process 4300, the IPI provider and the potential research partner explore the possibility of the partnership and determine whether the two entities are compatible with each other for performing the desired research. If the IPI provider and the potential research partner agree that they are compatible, the IPI provider sends a Partner Research Agreement to the potential research partner at step 4306 of the partner registration process 4300.

The IPI provider and the potential research partner may negotiate the terms of the Partner Research Agreement, except for those requiring compliance with the regulations of HIPAA and other state and federal laws. For example, the IPI provider and the potential research partner may negotiate the format and protocol by which data will be exchanged between the potential research partner's research system and external information systems 142 utilized by the potential research partner, such as a Clinical Trials Management Systems (CTMS) and/or Electronic Data Capture (EDC) systems. The Partner Research Agreement may also identify a CRO, such as eCast Corp. or Outcome Sciences Inc., who will provide a Clinical Research Coordinator (CRC) to conduct the clinical trial at the point of care. After all of the terms of the Partner Research Agreement are negotiated, the agreement is executed and returned to the IPI provider at step 4308 of the partner registration process 4300.

If the research partner negotiated for its research system to be developed to exchange data with any of the research partner's external information systems 142 in a format other than the standardized format in which that data is captured by the systems of the IPI 100, the interoperability engine is used to facilitate integration of those external information systems 142 with the research partner's research system at step 4310 of the partner registration process 4300. After integration development is completed at step 4312 of the partner registration process 4300, or if no integration was required, the partner's research system is added to the network of the IPI 100 at step 4314 of the partner registration process 4300. After the research partner's research system is added to the network of the IPI 100, the research partner is given access to a research partner web portal at step 4316 of the partner registration process 4300 through which the research partner can manage its research system, set up data feeds, and run queries. Managing its research system includes viewing those research tasks the research partner is in charge of completing and setting up data feeds and running queries includes choosing the criteria by which de-identified data is collected, tracked, and analyzed by the research system.

B. Sequential Filtering Process

Figure 44:
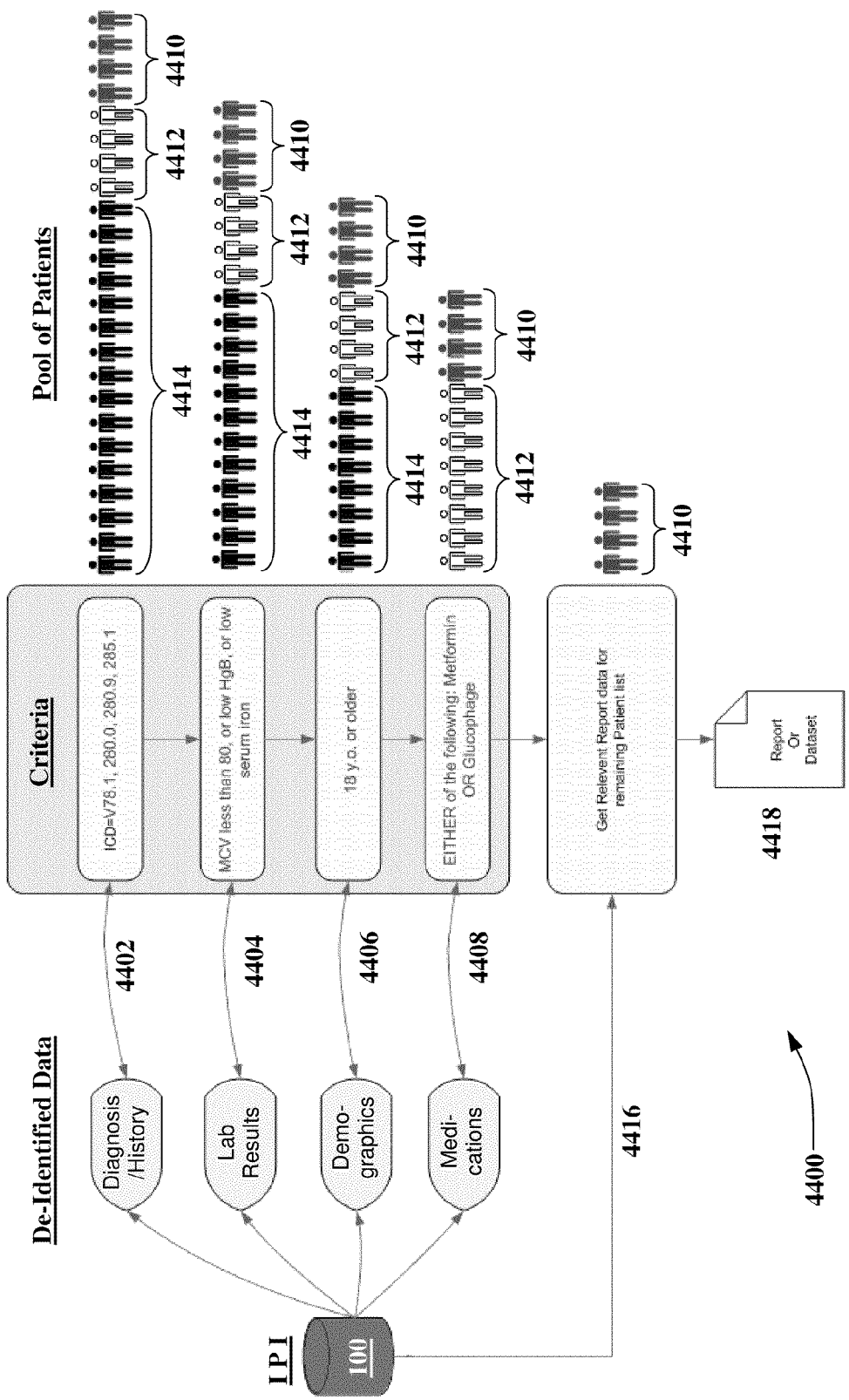
FIG. 44 is a schematic block diagram illustrating the functional steps of a sequential filtering process according to a non-limiting embodiment of the present invention.

As FIG. 44 illustrates, the research system may analyze, collect, and/or track data by applying a sequential filtering process 4400 to generate de-identified data sets from the data captured by the various systems of the IPI 100. The sequential filtering process is performed by a codified search of a universal vocabulary common to all databases using the SQL language to compare lexicons and prepare the desired result. That search can be performed utilizing functions/procedures that can be integrated into the databases of the various systems of the IPI 100. Such functions include SQL functions and, for large and/or complex queries, Stored Procedures (SPs) and User Defined Functions (UDFs). Using those functions, data can be efficiently queried from the databases of the various servers 104, 110, 116, 120, and 132 of the IPI 100, either individually, simultaneously, or at a central database where data has been aggregated (e.g., the database on the enhanced services server 116).

i. Identifying Qualifying Patients for Clinical Trials

In the example illustrated, the sequential filtering process includes steps 4402-4408 for determining the number of patients among a large pool of patients that qualify for a clinical trial 4410 (hereinafter "qualifying patients 4410"). Although FIG. 44 illustrates separate steps for performing the sequential filtering process, the research functionality of the present invention automatically performs those after a research partner chooses the criteria by which qualifying patients 4410 are to be identified. According, a research partner need only choose the criteria for identifying patients that qualify for a clinical trial via its research partner web portal, and the research functionality will automatically perform the sequential filtering process across the systems of the IPI 100 to determine the number of patients that satisfy all of those criteria.

In addition, although the pool of patients illustrated in FIG. 44 only includes twenty-four patients, that number of patients is provided for ease of explanation. As discussed above, the pool of patients can actually include fourteen million or more active patients. Among the pool of patients at each step, there may be patients that do not satisfy the associated criteria 4412 and patients that do satisfy the associated criteria 4414 in addition to the qualifying patients 4410 that qualify for the clinical trial by satisfying the criteria at every step.

Step 4402 in the exemplary sequential filtering process 4400 includes querying de-identified patient diagnosis/medical history data and determining the number of patients with specific diagnoses. Those diagnoses are queried based on the ICD values captured for those patients (e.g.; V78.1, which corresponds to screening for other and unspecified deficiency anemia; 280.0, which corresponds to iron deficiency anemia secondary to blood loss (chronic); 280.9, which corresponds to iron deficiency anemia unspecified; and 285.1, which corresponds to acute posthemorrhagic anemia). Step 4402 in the sequential filtering process 4400 reveals that twenty of twenty-four patients have been diagnosed with at least one of the health conditions specified.

Step 4404 in the exemplary sequential filtering process 4400 includes querying de-identified patient lab results data and determining the number of the remaining twenty patients that have a mean corpuscular volume (MCV) less than eighty, low hemoglobin (HgB), or low serum iron. The patient lab results may be queried based on the associated LOINC classification. Because the filtering process is sequential, only the data for the twenty patients that satisfied the criteria at step 4402 are queried at step 4404. Step 4404 in the sequential filtering process 4400 reveals that sixteen of the twenty patients that have been diagnosed with at least one of the health conditions specified in step 4402 also have the lab results specified in step 4404.

Step 4406 in the exemplary sequential filtering process 4400 includes querying de-identified patient demographic data and determining the number of the remaining sixteen patients that are eighteen years old or older. The demographic data is de-identified in accordance with the HIPAA privacy regulations, so the only element of data that is queried is the year. Again, because the filtering process is sequential, only the sixteen patients that satisfied the criteria at step 4402 and step 4404 are queried at step 4406. Step 4406 in the sequential filtering process 4400 reveals that twelve of the sixteen patients that have been diagnosed with at least one of the health conditions specified in step 4402 and at least one of the lab results specified in step 4404 also satisfy the demographic requirement specified in step 4406.

Step 4408 in the exemplary sequential filtering process 4400 includes querying de-identified patient medication data and determining the number of the remaining twelve patients that have been prescribed either Metformin or GLUCOPHAGE brand Metformin. The patient medication data may be queried based on its associated RxNorm classification. By querying only the twelve patients that satisfied the criteria at steps 4402-4406, step 4408 in the sequential filtering process 4400 reveals that four of the original twenty-four patients have been diagnosed with at least one of the health conditions specified in step 4402, have at least one of the lab results specified in step 4404, satisfy the demographic requirement specified in step 4406, and have been prescribed one of the medications specified in step 4408. Thus, the sequential filtering process 4400 determines that there are four qualifying patients 4410 that qualify for the clinical trial by satisfying each of the established criteria.

At step 4418, any additional de-identified data that is relevant to the clinical trial is retrieved from the IPI 100 for qualifying patients 4410. And, at step 4318, all of the retrieved data for the qualifying patients 4410 is presented in the form of an electronic report or a dataset. When the sequential filtering process 4400 is initiated by the IPI provider at the IPI provider's site 114, the electronic report or dataset is presented to the IPI provider at an administrator workstation 118 and can be transferred to the research partner that requested it at a researcher's site 108 or a third party (e.g., a pharmaceutical company) at an external information system 138 via one of the secured connections of the IPI 100. And, when the sequential filtering process 4400 is initiated by a research partner at the researcher's site 108 or is transferred from the IPI provider to the research partner at the researcher's site 108, the electronic report or dataset is presented to the research partner at a partner workstation 112. A research partner can transfer the electronic report or dataset from the research partner's research system to an external information system 142, such as a CTMS or EDC system, via one of the secured connections of the IPI 100. Regardless of who initiates the sequential filtering process via the research system, the research partner can establish the criteria for that search through its research partner web portal using its partner workstation 112, which, as discussed above, may include a PC, a laptop, a PDA, and an SME PED.

Thus, the present invention can utilize a sequential filtering process 4400 to quickly and accurately generate an electronic report or dataset for patients that qualify for a clinical trial that can be easily disseminated to the parties requesting that data. Moreover, that data can be collected in a matter of minutes in lieu of the months it used to take to identify qualifying patients 4410, which saves clinical trial sponsors and CROs millions of dollars. And, because the present invention provides an integrated system comprising standardized data for over fourteen million active patients, the patients that qualify for the clinical trial represent a more accurate cross-section of the population from which they are drawn, which is extremely desirable for clinical trials.

ii. Gathering Data for Quality Assessment and Financial Analysis

Although the sequential filtering process 4400 illustrated in FIG. 44 is described with respect to locating patients that qualify for clinical trials, the present invention also provides similar research functionality for generating reports or datasets of other clinical and financial information across the vast network of the IPI 100. For example, the present invention can be used to analyze, collect, and track data for comparing a medical practice to other practices (e.g., in the same specialty, in the same region, of the same size, etc.) based on customized criteria (e.g., previous performance, specified financial goals, etc.) or national standards and benchmarks (e.g., Medical Group Management Association (MGMA) certifications, Agency for Healthcare Research and Quality (AHRQ) quality indicators, National Committee for Quality Assurance (NCQA) accreditations, Healthcare Effectiveness Data and Information Set (HEDIS) measures, CMS initiatives, etc.). The present invention performs analytics on those electronic reports or datasets to generate average values that can be easily compared by clients and research partners. Such comparisons provide healthcare providers with guidance for improving the clinical quality and financial performance of their respective practices.

iii. Gathering Data for Adverse Event Reporting

The present invention also provides functionality similar to the sequential filtering process 4400 illustrated in FIG. 44 for generating reports or datasets that track the effects of various drugs and medical procedures on patients within the network of the IPI 100. For example, a research partner, such as a pharmaceutical company, can utilize the present invention to identify any adverse effects of one of its drugs by tracking patients that have taken that drug, alone or in combination with other drugs, and determining whether any pattern of illnesses or side effects appears among those patients. And, because the IPI 100 of the present invention actively analyzes, collects, and tracks data in real time, drug companies can quickly and accurately identify any adverse events and respond by removing the drug from the market or altering the composition of the drug. Moreover, the present invention provides functionality that allows the IPI provider or a research partner to establish criteria for automatically identifying such adverse events as they occur.

iv. Gathering Data for Drug Efficacy

In addition to tracking adverse events, the research functionality of the present invention can also be used to track the efficacy of various drugs by tracking actual usage of those drugs in various scenarios. That data can be used to verify and reinforce the conclusions drawn as a result of a clinical trial and confirm that marketing authorization of the drug was valid. Accordingly, the research functionality of the present invention can be utilized to accomplish any required pharmacovigilance (PV) activities during a drug's post-marketing period, such as those required by the World Health Organization (WHO) International Drug Monitoring Programme. For example, the present invention can be used to study how certain drugs are used and their impact on pregnancy outcomes by identifying pregnancy events across the systems of the IPI 100 and linking them to child births and deaths, birth defects, and the drugs administered to the pregnant patients based on the data captured for the pregnant patients at the various systems in the IPI 100.

v. Gathering Data for Disease Tracking

The research functionality of the present invention can also be used to provide real-time feedback for various other purposes, such as tracking diseases for disease registries or even tracking the flu. Moreover, that type of data tracking can be performed by globally polling the data on the systems of the IPI 100 as a whole in lieu of querying that data to identify specific datasets. Utilizing that broader, global polling functionality in real time, the research functionality of the present invention can be used as an electronic biosurvielance system for providing early warnings of health threats, early detection of health events, and overall situational awareness of disease activity on a national scale. The research functionality achieves those objectives by monitoring the environment for bacteria, viruses, and other biological agents that cause disease in real time across all of the systems of the IPI 100.

C. Client Registration Process

Returning to the example of the present invention's functionality for identifying qualifying patients 4410, the sequential filtering process 4400 only identifies the number of patients that satisfy all of the criteria for a clinical trial and provides de-identified data for those patients. The query results do not include any patient-specific information. For a research partner to obtain access to patient-specific data from a particular user of the IPI 100, that user must establish a formal relationship with the IPI provider by becoming a research client of the IPI provider. Accordingly, the present invention also provides functionality for recruiting IPI users to become research clients of the IPI provider. When an IPI user becomes a research client of the IPI provider, the IPI user not only authorizes research partners of the IPI provider to access patient-specific data for the IPI user's patient population, the IPI user is also given access to the infrastructure within the IPI 100 that interconnects all of the systems of the IPI 100 to the IPI provider's research partners' research systems (hereinafter "the Research Network").

Figure 45:
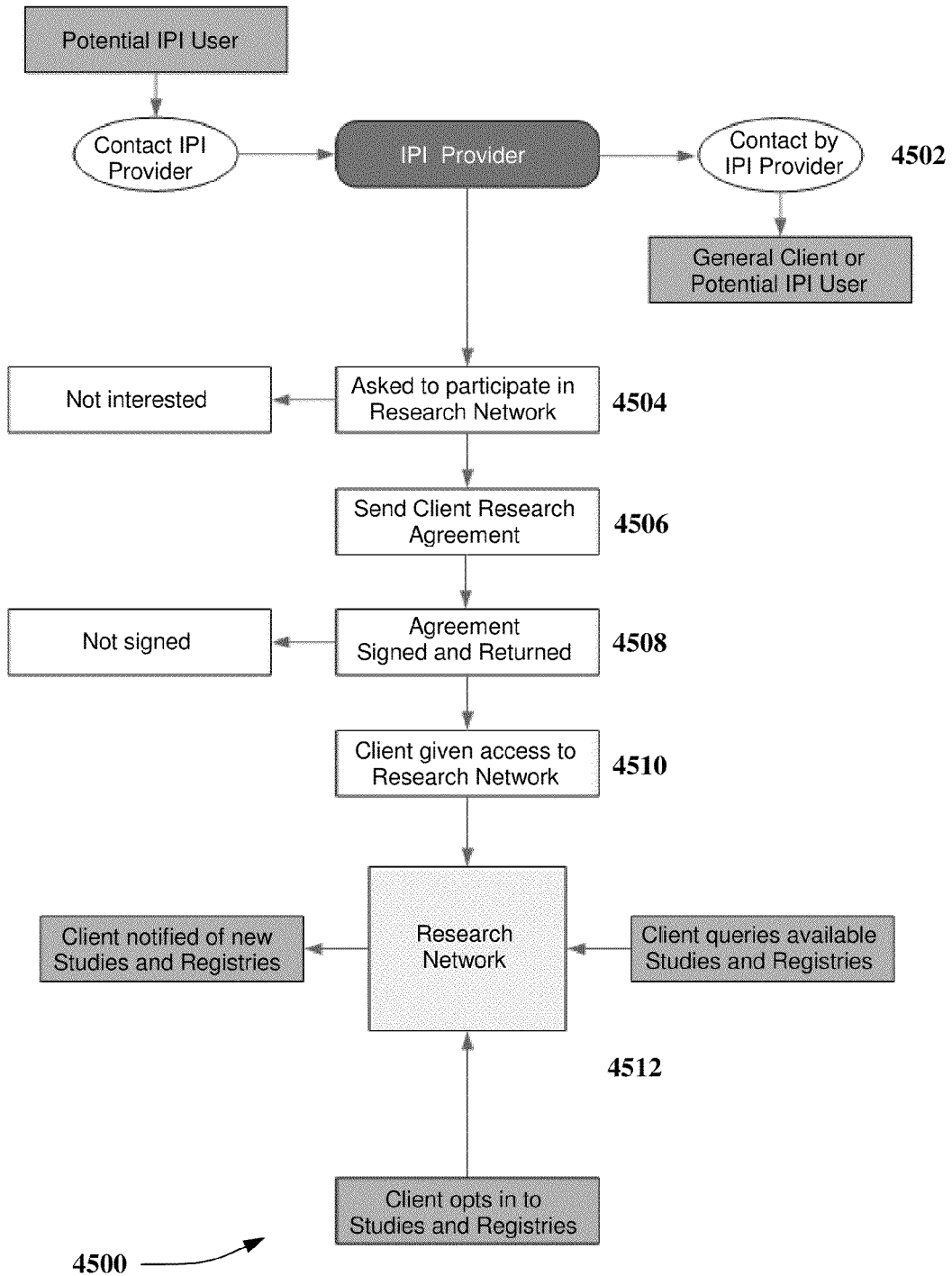
FIG. 45 is a schematic block diagram illustrating the functional steps of a client registration process according to a non-limiting embodiment of the present invention.

As FIG. 45 illustrates, the client registration process 4500 includes several steps before an IPI user can access the Research Network of the present invention. At step 4502 of the client registration process 4500, a potential user of the IPI 100 may contact the IPI provider to become a general client of the IPI provider and obtain at least one of the services provided by the IPI provider (e.g., an EHR system). In the alternative, the IPI provider may solicit potential IPI users to obtain at least one of the services provided by the IPI provider or may contact existing general clients that have already obtained at least one of the services provided by the IPI provider. Once contact is made at step 4502 of the client registration process, the potential IPI user or existing general client is asked if it would like to be a research client in addition to being a general client at step 4504 of the registration clients. By becoming a research client in addition to a general client, an IPI user is able to participate in the Research Network of the present invention as part of the services provided to the user by the IPI provider. Accordingly, the present invention provides an effective means for recruiting healthcare providers to participate in its Research Network.

If the IPI user is interested in participating in the Research Network, a Client Research Agreement is sent to the IPI user at step 4506 of the client registration process 4500 via any suitable means, such as via e-mail or via a link in the web portal of the system the IPI user is utilizing to obtain the IPI provider's services. The terms of that agreement set out the requirements that will be adhered to by both parties to ensure compliance with the regulations of HIPAA and other state and federal laws. If the IPI user agrees to the terms of the Client Research Agreement, the agreement is executed and returned to the IPI provider at step 4508 of the client registration process 4500. Because the IPI user is already using the services of the IPI provider, the system that the IPI user is utilizing to obtain those services is already integrated into the network of the IPI 100, and no integration is required for the IPI user to become part of the Research Network.

After the IPI user has executed and returned the Client Research Agreement at step 4508 of the client registration process 4500, the research client is given access to the Research Network at step 4510 of the client registration process 4500. The research client can access the Research Network at step 4512 of the client registration process 4500 via a research client web portal. The research client web portal provides functionality for the research client to easily view all of the clinical trials for which any of its patient's qualify, the criteria for each of those trials, and all of the patients that qualify for those trials. The research client can configure the research client web portal to send automatic notifications of any new clinical trials for which its patients qualify. The research client can also request to opt in to any available clinical trial via the research client web portal.

Participation in a clinical trial can be a source of income for those research clients that opt in to such trials, which serves as an incentive for more IPI users to become research clients. The more IPI users that become part of the Research System, the more powerful of a research tool the Research System becomes. But, before a research client can begin participating in a clinical trial, the qualifying patients 4410 may need to be screened and give their authorization to verify their eligibility for the clinical trial.

D. Patient Verification Process

Figure 46:
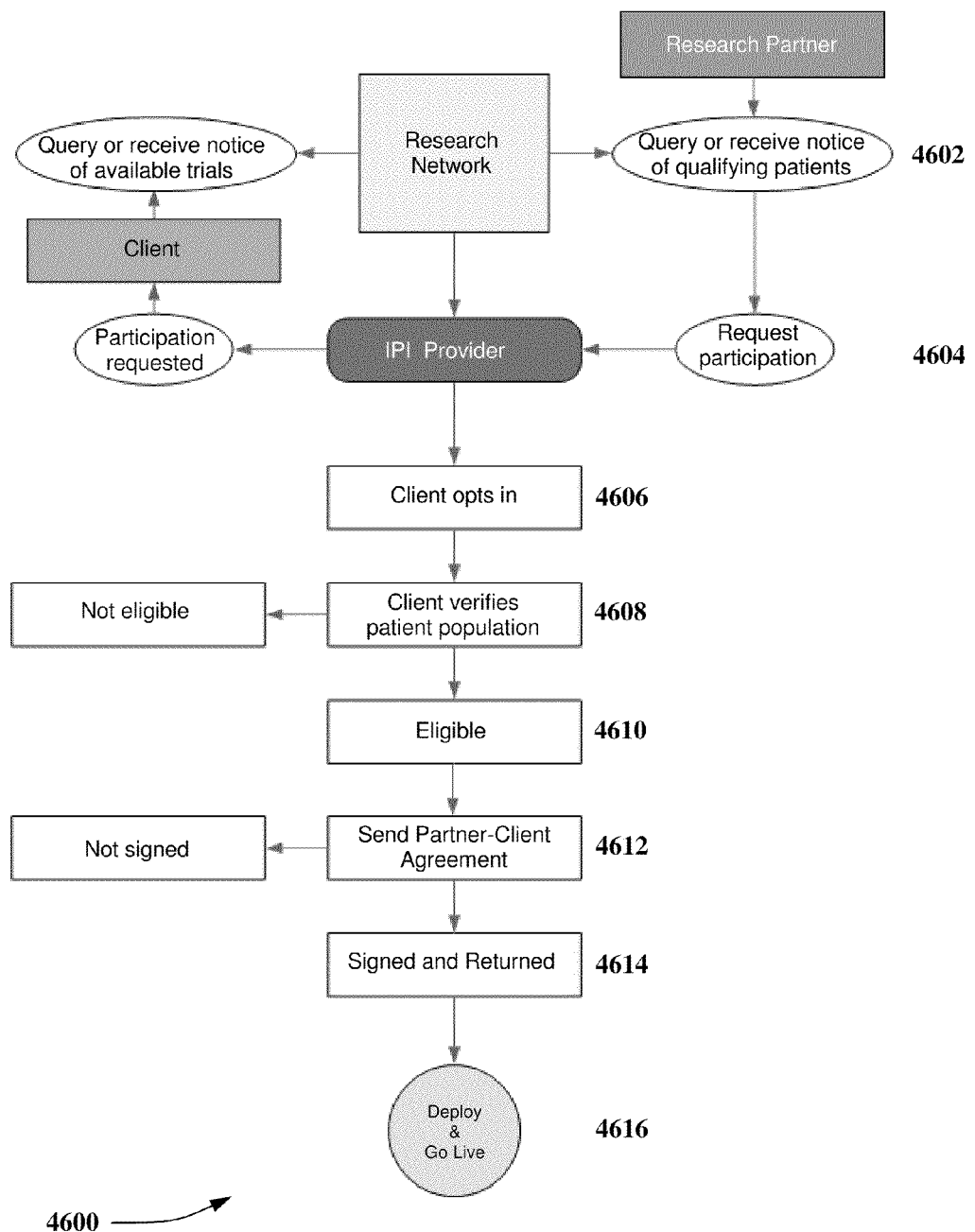
FIG. 46 is a schematic block diagram illustrating the functional steps of patient verification process according to a non-limiting embodiment of the present invention.

As FIG. 46 illustrates, the patient verification process 4600 includes several steps before the research client becomes active in a clinical trial. At step 4602 of the patient verification process 4600, a research client can query or receive a notification from the Research Network of the available clinical trials for which the research client qualifies. Or, in the alternative, the research partner may query or receive a notification from the Research Network at step 4602 of the patient verification process, identifying which research clients qualify for that research partner's clinical trial. Based on that query or notification, the research partner may contact the qualifying research client or the service IPI provider at step 4604 of the verification process 4600 to request that the qualifying research client participate in the research partner's clinical trial. Or, in yet another alternative, the IPI provider may automatically request that the qualifying research client participate in the research partner's clinical trial at step 4604 of the verification process 4600 based on its own query of the Research Network. Regardless of who generates the request for the qualifying research client to participate in the research partner's clinical trial, that request will go through the IPI provider so the IPI provider can facilitate verification of the qualifying patients 4410 and execution of a Partner-Client Agreement between the research client and the research partner before the research client begins participating in the clinical trial via the IPI 100.

At step 4606 of the verification process 4600, the qualifying research client can opt in to the research partner's clinical trial based on the research client's query or notification at step 4602 or based on the IPI provider's or research partner's request at step 4604. After opting in to the clinical trial, the research client must verify its population of qualifying patients 4410 at step 4608 of the verification process 4600. Verifying that a research client's qualifying patients 4410 are eligible for the clinical trial may include a screening process by which the research client schedules follow-up visits (e.g., preemptory evaluations) with its qualifying patients 4410 to run any other necessary tests to ensure that the qualifying patients 4410 satisfy the requisite criteria for the clinical trial. Verifying that a research client's qualifying patients 4410 are eligible for the clinical trial may also include having the qualifying patients 4410 sign a consent form, pre-populated with the required HIPAA-mandated language regarding the patients' protected information, authorizing their physician to place each patient's information on the Research Network.

If a research client's qualifying patients 4410 are verified as eligible to participate in the research partner's clinical trial at step 4610 of the verification process 4600, the IPI provider sends the research client and research partner a Partner-Client Agreement at step 4612 of the verification process 4600. The Partner-Client Agreement is between the research client and the research partner and sets forth all of the requirements and payments associated with performing the clinical trial. The Partner-Client Agreement also includes all language required to ensure both parties comply with the regulations of HIPAA. After both parties have executed the Partner-Client Agreement and returned it to the IPI provider at step 4614 of the verification process 4600, the research functionality of the present invention is deployed to the research partner and research client at step 4616 so they may go live and begin capturing clinical data in real time at the system of the IPI 100 utilized by the research client (e.g., an EHR systems).

As part of the research functionality deployed, the verified patients that are participating in the clinical trial are attached to the specific clinical trial so that the proper forms required for that clinical trial are automatically associated with and made available for those patients. In addition, triggering events are automatically associated with those forms according to the protocol established for the clinical trial so that the forms are made available only as certain events occur within the systems of the IPI 100. The manner in which the research functionality of the present invention can be used to complete and submit those forms is discussed in more detail below.

By simplifying and facilitating the interactions between research clients and research partners that are required to recruit research clients and get patients enrolled in clinical trials, the present invention provides for completing the enrollment process for a clinical trial in a matter of days instead of months. Accordingly, healthcare providers can quickly begin enrolling candidates, participating in the clinical trials, and receiving reimbursements form clinical trial sponsors or CROs via the functionality of the present invention. And, in addition to recruiting research clients and enrolling patients for clinical trials, similar methods can also be utilized for recruiting research clients and enrolling patients for other types of medical research, such as disease registries and quality of care initiatives. Thus, the functionality of the present invention eliminates many, if not all, of the hurdles put in place by HIPAA that otherwise deter healthcare providers from participating in medical research.

E. Completing a Clinical Research

In addition to the present invention's functionality for recruiting research clients and enrolling patients to participate in medical research, the present invention also provides functionality for carrying out that research. Depending on the type of research being carried out, the present invention provides different functionality. For example, a research partner can use the template builder component 1102 provided on one of the systems of the IPI 100 or Form Manager software to generate the case report forms (CRF) required to complete a clinical trial. The research functionality of the present invention can then be used to retrieve, complete, and submit that form using the RFD form management standard.

In that example, the research partner or the IPI provider uses the research functionality of the present invention to pre-populate much of the data in those forms using the data stored on the various systems of the IPI 100. Those pre-populated forms are then transferred to a clinical trial sponsor's or CRO's EDC system for completion via data capture at the point of care by an authorized physician, delegate, Principle Investigator (PI), and/or CRC conducting the clinical trial (i.e., the Form Filler). Rather than being retrieved, those documents may also be sent automatically to the EDC system based on a triggering event, such as a scheduled patient visit. Those forms may be completed using quick selections from lists or input and selections in control types, as discussed above with respect to the template builder component 1102. Those quick selections and input can be made manually with traditional user input devices (e.g., a mouse and/or a keyboard) or via the speech understanding functionality of the present invention. After the forms are completed at the EDC system, they are submitted back to the clinical trial sponsor or CRO (i.e., the Form Receiver and/or Form Archiver) at an external information system 142, or at their research system within the IPI 100, for analysis and archiving.

Accordingly, the research functionality of the present invention streamlines data entry and shortens the time required by the authorized physician, delegate, PI, and/or CRC to complete those forms by allowing them to retrieve, complete, and submit the required forms within a single application. And, where the EDC systems has been integrated with the systems of the IPI 100, data captured during the clinical trials using those EDC systems can be captured in real time within the IPI 100 for use by the other systems of the IPI 100. Even where the EDC system is not integrated with the other systems of the IPI 100, the IPI 100 can be configured to consume that data.

In addition, the IPI 100 can also be configured to consume data from a CTMS. For example, the present invention can utilize the Retrieve Protocol for Execution Profile (RPE) integration standard to retrieve the clinical trial instructions (i.e., the trial protocol) from the CTMS system and execute them at the systems of the IPI 100 that will be used to capture data for the clinical trial (e.g., EHR systems). Accordingly, the RPE integration standard can be utilized to integrate site-based clinical research work flow into the task managers of EHR systems within the IPI 100 to automate scheduling and consume trial protocol documents. Thus, the RPE integration standard can be used to expand upon the amount system integration facilitated by the RFD form management standard. The RPE integration standard is currently maintained by the IHE and its contents are hereby incorporated by reference.

The present invention can also use the RFD form management standard to retrieve Adverse Event (AE) forms from local Institutional Review Boards (IRBs), to pre-populate data into those forms, and to submit those forms back to the IRBs, to the clinical trial sponsor or CRO, and to all other sites participating in the same clinical trial. AE forms are used to report adverse changes in health or side-effects that occur in a patient participating in a clinical trial while the patient is receiving treatment (e.g., receiving test medication, using a test medical device, etc.) or within a pre-defined period of time after their treatment is completed. And, because of the integrated functionality of the present invention, the completed AE forms can be quickly and efficiently completed and submitted to all of the necessary parties, particularly the other research sites participating in the clinical trial.

The present invention can also use the RFD form management standard to submit forms to various safety/quality organizations (e.g., MGMA, AHRQ, NCQA, HEDIS, CMS, etc.) that track the performance of specific healthcare providers and determine whether those healthcare providers have satisfied certain quality measures and therefore qualify for specific certifications, accreditations, and/or incentives. For example, a healthcare provider can utilize that functionality to pre-populate the forms required by CMS to qualify for Pay for Performance (P4P) incentive pay under the Physician Quality Reporting Initiative (PQRI). The healthcare provider then completes any part of the form not pre-populated by the present invention and submits it to CMS.

Where the systems of the IPI 100 contain all of the information required to complete specific forms and an IPI user need not complete any part of that form, the present invention can also be configured to send the defined data elements for each specific form to a central router or registry in a batch or near real time feed. That feed effectively completes the forms without any action by the IPI user other than capturing the required data. Accordingly, IPI users can complete forms in real time as data is collected, which the associated IPI system will automatically submit without any additional IPI user interaction. That functionality is particularly useful for quality initiatives that require physicians to regularly complete and submit identical forms on quality measures for a variety of covered services.

The present invention can also use the RFD form management standard to submit forms to various public health organizations based on certain triggering events. For example, when a user of an EHR system within the IPI 100 indicates that a child was born to a patient, that event will automatically trigger the EHR system to retrieve the required registration form from the local Department of Public Health. The EHR system will also pre-populate the form with the parent's demographic data, the baby's date of birth, and any other information captured by the EHR system, such as the baby's weight as measured by an electronic scale connected to the EHR system. After the registration form is complete by the EHR system user, the EHR system will automatically submit the completed form back the local Department of Public Health in a format easily recognized and processed by that Department of Public Health.

V. Overview of Features

The integrated ambulatory suite 400 of the present invention is designed to be intuitive to the user and provide a secure environment that can be accessed at the clinician's office or at a remote site. The system also interfaces to email and the clinician's website and provides support for phone messaging, patient education materials, website, direct patient data entry via the web, email, and return on investment (ROI) studies.

The integrated ambulatory suite 400 eliminates the need for paper charts, thereby reducing the amount of office space allocated to storing patient records, and allowing electronic transfer of information between practices. All incoming paper documents and existing paper patient files, can be scanned or otherwise entered into the system and the paper files eliminated. The patient's EHR can be accessed at any time and from any location, thereby eliminating manual chart pulls and misplaced paper files. The number of chart pulls is reduced by about 50% within six months of implementing the present invention, and about 85% at twelve months.

After the integrated ambulatory suite 400 is fully implemented, transcription costs could be eliminated, malpractice premiums could be reduced by about 3-5% from insurance companies that offer physicians who use an EMR or EHR system a discount due to the increased detail of documentation generated by such systems, as opposed to dictation or handwriting, and staff savings of about 15%. Perhaps most importantly, clinician productivity gain increases by about 20% after only twelve months, resulting in a savings of about $7,000-15,000 per clinician each year.

The information provides rapid and concise malpractice proof to help the user defend against malpractice claims and HCFA audits. The system also offers the clinician prescription assistance with brand name and generic pricing and dosage, national drug codes, medication lists, allergy cross-checks (drug-drug, drug-food, drug-disease interactions), and side affects. The entry of charges is automated and the resulting documentation is checked for compliance with billing and claims filings.

Although the preferred embodiment of the invention is for use at a clinician's practice, the system can be implemented at the office of any service professional. The system is configurable at the user and practice levels so that a practice can assign specific duties and responsibilities to employees to maximize overall office productivity without restrictions imposed by existing practice management systems and EMR and EHR systems.

Data entry and capture is made easier through the use of embedded speech understanding functionality. Because that functionality is seamlessly integrated with the various modules and components of the integrated ambulatory suite 400, users do not have to learn how to use any new software to complete clinical documents, which increases the likelihood of its acceptance. Moreover, because healthcare is a dictation-intensive field, the speech understanding functionality of the present invention provides a mechanism for entering and capturing data that is familiar to most clinicians, which helps ease healthcare providers' transition into the electronic record-keeping medium of the integrated ambulatory suite 400.

Using all of the functionality discussed above and equivalents thereof, the present invention is able to further provide an integrated system 100 for quickly, accurately, and seamlessly collecting, tracking, and analyzing medical data across a vast patient population. It also provides functionality for managing and coordinating care across a community of healthcare providers in different settings, which can reduce the costs of unnecessary emergency room visits, repeated lab tests, and preventable hospitalizations. The system 100 is particularly suited for performing medical research because it provides infrastructure and functionality for utilizing that data to more effectively and efficiently perform medical research, maintain disease registries, track patient care for quality and safety initiatives, and perform composite clinical and financial analytics. Moreover, the infrastructure and functionality of the present invention facilitate the measurement and promotion of continued improvement in clinical care.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. Therefore, it is not desired to limit the invention to the specific examples disclosed or the exact construction and operation shown and disclosed. Rather, all suitable modifications and equivalents may be resorted to, falling within the scope of the invention.

What is claimed is:

1. An integrated medical software system with embedded transcription functionality comprising:
    a processor configured to implement:
        a clinical software module that is configured to be executed by the processor to create an electronic document and to capture clinical data for a patient in the electronic document during an encounter with the patient;
        a transcription software application that is configured to be executed by the processor to select predefined clinical data that will appear within the electronic document in response to speech commands and to automatically transcribe dictated clinical data that will appear within the electronic document in response to dictation, the predefined clinical data being previously linked to at least one of a diagnosis code and a procedure code and the dictated clinical data being automatically linked to at least one of a diagnosis code and a procedure code as it is transcribed; and
        an account management software module that is configured to be executed by the processor to automatically generate at least one of a bill, a claim, or a statement for the patient using the at least one of a diagnosis code and a procedure code linked to at least one of the predefined clinical data and the dictated clinical data;
    wherein the processor is further configured to link the dictated clinical data automatically in real time to a clinical flag by:
    (i) converting the dictated clinical data into text;
    (ii) parsing the text to determine a meaning; and
    (iii) providing a link from a portion of the text associated with the meaning to the clinical flag.

2. The integrated software system of claim 1, wherein the processor is further configured to implement:
    a registration software module that is configured to be executed by the processor to capture demographic data and associate it with the patient, the demographic data including at least one of a name, a digital photograph, an address, a date of birth, an age, a social security number, and a sex of the patient,
    wherein the transcription software application is configured to receive speech commands for selecting predefined demographic data that will be associated with the patient and to receive dictated demographic data that will be automatically transcribed and associated with the patient, and
    wherein the account management software module is configured to automatically generates at least one of a bill, a claim, or a statement for the patient using at least a portion of the demographic data.

3. The integrated software system of claim 2, wherein the processor is further configured to implement:
    a scheduling software module that is configured to be executed by the processor to schedule the patient and at least one of a clinician, a staff member, and equipment at a healthcare provider using scheduling data and the demographic data, the scheduling data including at least one of a time, a location, and a name for the patient and the at least one of a clinician, a staff member, and equipment,
    wherein the transcription software application is configured to receive speech commands for selecting predefined scheduling data for the patient and the at least one of a clinician, a staff member, and equipment and to receive dictated scheduling data that is automatically transcribed for the patient and the at least one of a clinician, a staff member, and equipment.

4. The integrated software system of claim 3, wherein the processor is further configured such that:
    at least a portion of the predefined scheduling data is previously linked to a section in the electronic document where it will be automatically populated when the electronic document is created by the clinical software module; and/or
    at least a portion of the dictated scheduling data is automatically linked to a section in the electronic document as it is transcribed where it will be automatically populated when the electronic document is created by the clinical software module.

5. The integrated software system of claim 3, wherein the processor is further configured to implement a framework software module that is integrated with the clinical software module, the account management software module, registration software module, and the scheduling software module using a common architecture and that is configured to be executed by the processor to support an exchange of the clinical data, the demographic data, and the scheduling data between those software modules in a normalized data format.

6. The integrated software system of claim 2, wherein the processor is configured such that:
    at least a portion of the predefined demographic data is previously linked to a section in the electronic document where it will be automatically populated when the electronic document is created by the clinical software module; and/or
    at least a portion of the dictated demographic data is automatically linked to a section in the electronic document as it is transcribed where it will be automatically populated when the electronic document is created by the clinical software module.

7. The integrated software system of claim 1, wherein the processor is further configured such that the transcription software application includes a learning function that is configured to associate an error in transcription to an associated correction so the error in transcription is not repeated by the transcription software application.

8. The integrated software system of claim 1, wherein the processor is further configured for the transcription software application to synthesize transcribed text into an XML document and to transform that XML document into an electronic document using predefined style sheets, the predefined style sheets being defined by a clinical document format according to at least one of a Continuity of Care Document (CCD) standard, Clinical Document Architecture (CDA) standard, and a Continuity of Care Record (CCR) standard.

9. The integrated software system of claim 1, wherein the processor is further configured for the transcription software application to receive speech commands for selecting at least a portion of transcribed text and to transcribe dictation to replace the selected portion of transcribed text.

10. A method of using an integrated medical software system with embedded transcription functionality comprising the steps of:
- executing a clinical software module with a processor to create an electronic document and to capture clinical data for a patient in the electronic document during an encounter with the patient;
- executing a transcription software application with the processor to perform at least one of the steps of:
  - selecting predefined clinical data that will appear within the electronic document in response to speech commands, the predefined clinical data being already linked to at least one of a diagnosis code and a procedure code; and
  - transcribing dictated clinical data that will appear within the electronic document in response to dictation, the dictated clinical data being automatically linked to at least one of a diagnosis code and a procedure code as it is transcribed; and
- executing an account management software module with the processor to automatically generate at least one of a bill, a claim, or a statement for the patient using the at least one of a diagnosis code and a procedure code linked to at least one of the predefined clinical data and the dictated clinical data, wherein:
- the dictated clinical data is automatically linked in real time to a clinical flag by:
- (i) converting the dictated clinical data into text;
- (ii) parsing the text to determine a meaning; and
- (iii) providing a link from a portion of the text associated with the meaning to the clinical flag.

11. The method of claim 10, further comprising the step of:
- executing a registration software module with the processor to capture demographic data and associate it with the patient, the demographic data including at least one of a name, a digital photograph, an address, a date of birth, an age, a social security number, and a sex of the patient,
- wherein the step of executing the transcription software application includes receiving at least one of:
  - speech commands for selecting predefined demographic data that will be associated with the patient, and
  - dictated demographic data that will be automatically transcribed and associated with the patient, and
- wherein the step of executing the account management software module includes automatically generating at least one of a bill, a claim, or a statement for the patient using the demographic data.

12. The method of claim 11, further comprising the step of:
- executing a scheduling software module with the processor to schedule the patient and at least one of a clinician, a staff member, and equipment at a healthcare provider using scheduling data and the demographic data, the scheduling data including at least one of a time, a location, and a name for the patient and the at least one of a clinician, a staff member, and equipment,
- wherein the step of executing the transcription software application includes at least one of:
  - receiving speech commands for selecting predefined scheduling data for the patient and the at least one of a clinician, a staff member, and equipment, and
  - receiving dictated scheduling data that is automatically transcribed for the patient and the at least one of a clinician, a staff member, and equipment.

13. The method of claim 12, wherein:
- at least a portion of the predefined scheduling data is previously linked to a section in the electronic document where it will be automatically populated when the electronic document is created by the clinical software module; and/or
- at least a portion of the dictated scheduling data is automatically linked to a section in the electronic document as it is transcribed where it will be automatically populated when the electronic document is created by the clinical software module.

14. The method of claim 12, further comprising the step of executing a framework software module with the processor to support an exchange of the clinical data, the demographic data, and the scheduling data between those software modules in a normalized data format, the framework software module being integrated with the clinical software module, the account management software module, registration software module, and the scheduling software module using a common architecture.

15. The method of claim 11, wherein:
- at least a portion of the predefined demographic data is previously linked to a section in the electronic document where it will be automatically populated when the electronic document is created by the clinical software module; and/or
- at least a portion of the dictated demographic data is automatically linked to a section in the electronic document as it is transcribed where it will be automatically populated when the electronic document is created by the clinical software module.

16. The method of claim 10, wherein step of executing the transcription software application includes performing a learning function that associates an error in transcription to an associated correction so the error in transcription is not repeated by the transcription software application.

17. The method of claim 10, wherein the step of executing the transcription software application includes:
- synthesizing transcribed text into an XML document; and
- transforming that XML document into an electronic document using predefined style sheets, the predefined style sheets being defined by a clinical document format according to at least one of a Continuity of Care Document (CCD) standard, Clinical Document Architecture (CDA) standard, and a Continuity of Care Record (CCR) standard.

18. The method of claim 10, wherein the step of executing the transcription software application includes:
- receiving speech commands for selecting at least a portion of transcribed text; and
- transcribing dictation to replace the selected portion of transcribed text.

* * * * *